(12) United States Patent
Katopodis et al.

(10) Patent No.: US 11,773,160 B1
(45) Date of Patent: Oct. 3, 2023

(54) IMMUNE-STIMULATING IL-2 FUSION PROTEINS

(71) Applicant: Anaveon AG, Basel (CH)

(72) Inventors: Andreas Katopodis, Basel (CH); Christoph Huber, Basel (CH); Patrizia Murer, Basel (CH)

(73) Assignee: Anaveon AG, Basel (CH)

( * ) Notice: Subject to any disclaimer, the term of this patent is extended or adjusted under 35 U.S.C. 154(b) by 0 days.

(21) Appl. No.: 17/817,886

(22) Filed: Aug. 5, 2022

(51) Int. Cl.
*C07K 14/55* (2006.01)
*C07K 16/24* (2006.01)
*A61K 39/00* (2006.01)
*A61K 38/00* (2006.01)

(52) U.S. Cl.
CPC ............ *C07K 16/246* (2013.01); *C07K 14/55* (2013.01); *A61K 38/00* (2013.01); *A61K 2039/505* (2013.01); *C07K 2317/24* (2013.01); *C07K 2317/565* (2013.01); *C07K 2317/92* (2013.01); *C07K 2319/00* (2013.01)

(58) Field of Classification Search
CPC .................................................. C07K 16/246
USPC ........................................................ 424/85.2
See application file for complete search history.

(56) References Cited

U.S. PATENT DOCUMENTS

| | | | |
|---|---|---|---|
| 4,618,486 A | 10/1986 | Lundblad | |
| 5,869,046 A | 2/1999 | Presta et al. | |
| 6,121,022 A | 9/2000 | Presta et al. | |
| 6,171,586 B1 | 1/2001 | Lam et al. | |
| 6,277,375 B1 | 8/2001 | Ward | |
| 2019/0016797 A1* | 1/2019 | Arenas-Ramirez | A61P 35/00 |

FOREIGN PATENT DOCUMENTS

| | | |
|---|---|---|
| EP | 0154316 B1 | 9/1989 |
| EP | 0401384 B1 | 3/1996 |
| EP | 0413622 B1 | 2/1998 |
| WO | 9315199 A1 | 8/1993 |
| WO | 9315200 A1 | 8/1993 |
| WO | 9734631 A1 | 9/1997 |
| WO | 9823289 A1 | 6/1998 |
| WO | 2004016286 A2 | 2/2004 |
| WO | 2006044908 A2 | 4/2006 |
| WO | 2007095337 A2 | 8/2007 |
| WO | 2012107417 A1 | 8/2012 |
| WO | 2016005950 A1 | 1/2016 |
| WO | 2017122130 A1 | 7/2017 |

OTHER PUBLICATIONS

Cleland, J.L., et al., "The Development of Stable Protein Formulations: A Close Look at Protein Aggregation, Deamidation, and Oxidation", Critical Reviews in Therapeutic Drug Carrier Systems, 10(4):307-377 (1993), 74 pages.
Colandene, J.D. et al., "Lyophilization Cycle Development for a High-Concentration Monoclonal Antibody Formulation Lacking a Crystalline Bulking Agent", Journal of Pharmaceutical Sciences, vol. 96, No. 6, Jun. 2007, pp. 1598-1608.
Daugherty, A.L. et al., "Formulation and delivery issues for monoclonal antibody therapeutics", Elsevier, ScienceDirect, Advanced Drug Delivery Reviews 58 (2006), pp. 686-706.
Schulman, E.S., "Development of a Monoclonal Anti-Immunoglobulin E Antibody (Omalizumab) for the Treatment of Allergic Respiratory Disorders", Am J Respir Crit Care Med, vol. 164, pp. S6-S11, 2001, 6 pages.
Wang, W., "Instability, stabilization, and formulation of liquid protein pharmaceuticals", Elsevier, International Journal of Pharmaceutics 185 (1999), pp. 129-188.
Rosalia, R.A., et al., "Use of enhanced intedeukin-2 formulations for improved immunotherapy against cancer", University of Zurich, 2014, 22 pages.
Murer, P., et al., "Antibody-cytokine fusion proteins: a novel class of biopharmaceuticals for the therapy of cancer and of chronic inflammation", Europe PMC Funders Group, N Biotechnol Sep. 25, 2019; 52: 42-53, 28 pages.
Arenas-Ramirez, N., et al., "Improved cancer immunotherapy by a CD25-mimobody conferring selectivity to human interleukin-2", Science Translational Medicine, Research Article, Nov. 30, 2016, 13 pages.
Krieg, C., et al., "Improved IL-2 immunotherapy by selective stimulation of IL-2 receptors on lymphocytes and endothelial cells", PNAS, vol. 107, No. 26, Jun. 29, 2010, 6 pages.
Sahin, D., et al., "An IL-2-grafted antibody immunotherapy with potent efficacy against metastatic cancer", Nature Communications, (2020) 11:6440, https://doi.org/10.1038/s41467-020-20220-1, www.nature.com/naturecommunications, 12 pages.
Overwijk, W.W., et al., "Engineering IL-2 to Give New Life to T Cell Immunotherapy", Annual Review of Medicine 2021, 72, Nov. 6, 2020, pp. 281-311.
Letourneau, S., et al., "IL-2/anti-IL-2 antibody complexes show strong biological activity by avoiding interaction with IL-2 receptor a subunit CD25", PNAS, Feb. 2, 2010, 107(5), 18 pages.

\* cited by examiner

*Primary Examiner* — Sean E Aeder

(74) *Attorney, Agent, or Firm* — Arrigo, Lee, Guttman & Mouta-Bellum, LLP

(57) ABSTRACT

The present invention relates to immune-stimulating IL-2 fusion proteins comprising antibodies joined to human interleukin-2 (hIL-2). The invention more specifically relates to humanized monoclonal antibodies or fragments thereof joined to hIL-2 or variants thereof and displaying a unique capability of preferentially stimulating cytotoxic T cells and NK cells compared to Treg cells. Furthermore, the invention relates to in vitro and in vivo therapeutic applications of the IL-2 fusion proteins, in particular as an immunotherapy in the treatment of cancer.

20 Claims, 5 Drawing Sheets

Specification includes a Sequence Listing.

SEQUENCE LISTING

```
Sequence total quantity: 101
SEQ ID NO: 1                moltype = AA  length = 153
FEATURE                     Location/Qualifiers
source                      1..153
                            mol_type = protein
                            organism = Homo sapiens
SEQUENCE: 1
MYRMQLLSCI ALSLALVTNS APTSSSTKKT QLQLEHLLLD LQMILNGINN YKNPKLTRML    60
TFKFYMPKKA TELKHLQCLE EELKPLEEVL NLAQSKNFHL RPRDLISNIN VIVLELKGSE   120
TTFMCEYADE TATIVEFLNR WITFCQSIIS TLT                                153

SEQ ID NO: 2                moltype = AA  length = 134
FEATURE                     Location/Qualifiers
source                      1..134
                            mol_type = protein
```

-continued

```
                          organism = synthetic construct
SEQUENCE: 2
MAPTSSSTKK  TQLQLEHLLL  DLQMILNGIN  NYKNPKLTRM  LTFKFYMPKK  ATELKHLQCL   60
EEEELKPLEEV LNLAQSKNFH  LRPRDLISNI  NVIVLELKGS  ETTFMCEYAD  ETATIVEFLN  120
RWITFSQSII  STLT                                                        134

SEQ ID NO: 3              moltype = AA  length = 132
FEATURE                   Location/Qualifiers
source                    1..132
                          mol_type = protein
                          organism = synthetic construct
SEQUENCE: 3
NFHLRPRDLI  SNINVIVLEL  KGSETTFMCE  YADETATIVE  FLNRWITFCQ  SIISTLTPTS   60
SSTKKTQLQL  EHLLLDLQMI  LNGINNYKNP  KLTRMLTFKF  YMPKKATELK  HLQCLEEELK  120
PLEEVLNLAQ  SK                                                          132

SEQ ID NO: 4              moltype = AA  length = 132
FEATURE                   Location/Qualifiers
source                    1..132
                          mol_type = protein
                          organism = synthetic construct
SEQUENCE: 4
NFHLRPRDLI  SNINVIVLEL  KGSETTFMCE  YADETATIVE  FLNRWITFSQ  SIISTLTPTS   60
SSTKKTQLQL  EHLLLDLQMI  LNGINNYKNP  KLTRMLTFKF  YMPKKATELK  HLQCLEEELK  120
PLEEVLNLAQ  SK                                                          132

SEQ ID NO: 5              moltype = AA  length = 451
FEATURE                   Location/Qualifiers
source                    1..451
                          mol_type = protein
                          organism = synthetic construct
SEQUENCE: 5
EVQLVQSGAE  VKKPGESLKI  SCKGSGYAFT  NYLIEWVRQM  PGKGLEWMGV  INPGSGGTNY   60
NEKFKGQVTI  SADKSISTAY  LQWSSLKASD  TAMYYCARWR  GEGYYAYFDV  WGQGTTVTVS  120
SASTKGPSVF  PLAPSSKSTS  GGTAALGCLV  KDYFPEPVTV  SWNSGALTSG  VHTFPAVLQS  180
SGLYSLSSVV  TVPSSSLGTQ  TYICNVNHKP  SNTKVDKRVE  PKSCDKTHTC  PPCPAPELLG  240
GPSVFLFPPK  PKDTLMISRT  PEVTCVVVDV  SHEDPEVKFN  WYVDGVEVHN  AKTKPREEQY  300
ASTYRVVSVL  TVLHQDWLNG  KEYKCKVSNK  ALPAPIEKTI  SKAKGQPREP  QVYTLPPSRE  360
EMTKNQVSLT  CLVKGFYPSD  IAVEWESNGQ  PENNYKTTPP  VLDSDGSFFL  YSKLTVDKSR  420
WQQGNVFSCS  VMHEALHNHY  TQKSLSLSPG  K                                   451

SEQ ID NO: 6              moltype = AA  length = 218
FEATURE                   Location/Qualifiers
source                    1..218
                          mol_type = protein
                          organism = synthetic construct
SEQUENCE: 6
AIRLTQSPSS  FSASTGDRVT  ITCKASQSVD  YQGDSYMNWY  QQKPGKAPKL  LIYAASNLES   60
GVPSRFSGSG  SGTDFTLTIS  SLQSEDFATY  YCQQSNEDPY  TFGGGTKVEI  KRTVAAPSVF  120
IFPPSDEQLK  SGTASVVCLL  NNFYPREAKV  QWKVDNALQS  GNSQESVTEQ  DSKDSTYSLS  180
STLTLSKADY  EKHKVYACEV  THQGLSSPVT  KSFNRGEC                            218

SEQ ID NO: 7              moltype = AA  length = 121
FEATURE                   Location/Qualifiers
source                    1..121
                          mol_type = protein
                          organism = synthetic construct
SEQUENCE: 7
EVQLVQSGAE  VKKPGESLKI  SCKGSGYAFT  NYLIEWVRQM  PGKGLEWMGV  INPGSGGTNY   60
NEKFKGQVTI  SADKSISTAY  LQWSSLKASD  TAMYYCARWR  GEGYYAYFDV  WGQGTTVTVS  120
S                                                                       121

SEQ ID NO: 8              moltype = DNA  length = 363
FEATURE                   Location/Qualifiers
source                    1..363
                          mol_type = other DNA
                          organism = synthetic construct
SEQUENCE: 8
gaagtgcagc  tggtgcagtc  tggcgctgaa  gtgaagaagc  ccggcgagtc  cctgaagatc   60
tcctgcaagg  gctccggcta  cgccttcacc  aactacctga  tcgagtgggt  ccgacagatg  120
cccggcaagg  gcctggagtg  gatgggcgtg  atcaaccccg  gctccggcgg  caccaactac  180
aacgagaagt  tcaagggcca  agtcacaatc  tccgccgaca  gtccatctc   caccgcctac  240
ctgcagtggt  cctccctgaa  ggcctccgac  accgccatgt  actactgcgc  cagatggcgg  300
ggagaaggct  actacgccta  cttcgacgtg  tggggccagg  gcaccaccgt  gaccgtgtcc  360
tct                                                                     363

SEQ ID NO: 9              moltype = AA  length = 111
FEATURE                   Location/Qualifiers
source                    1..111
```

```
                        mol_type = protein
                        organism = synthetic construct
SEQUENCE: 9
AIRLTQSPSS FSASTGDRVT ITCKASQSVD YQGDSYMNWY QQKPGKAPKL LIYAASNLES    60
GVPSRFSGSG SGTDFTLTIS SLQSEDFATY YCQQSNEDPY TFGGGTKVEI K            111

SEQ ID NO: 10           moltype = DNA   length = 333
FEATURE                 Location/Qualifiers
source                  1..333
                        mol_type = other DNA
                        organism = synthetic construct
SEQUENCE: 10
gccatcagac tgacccagag cccctccagc ttctccgcct ccaccggcga cagagtgacc    60
atcacatgca aggcctccca gtccgtggac taccaggcg actcctacat gaactggtat   120
cagcagaagc ccggcaaggc ccctaagctg ctgatctacg ccgcctccaa cctggaatcc   180
ggcgtgccct ccggttctc cggctctggc tctggcaccg acttcaccct gaccatctcc   240
agcctgcagt ccgaggactt cgccacctac tactgccagc agtccaacga ggaccctac    300
accttcggcg gaggcaccaa gtggaaatc aag                                 333

SEQ ID NO: 11           moltype = AA   length = 10
FEATURE                 Location/Qualifiers
source                  1..10
                        mol_type = protein
                        organism = synthetic construct
SEQUENCE: 11
GYAFTNYLIE                                                           10

SEQ ID NO: 12           moltype = AA   length = 17
FEATURE                 Location/Qualifiers
source                  1..17
                        mol_type = protein
                        organism = synthetic construct
SEQUENCE: 12
VINPGSGGTN YNEKFKG                                                   17

SEQ ID NO: 13           moltype = AA   length = 12
FEATURE                 Location/Qualifiers
source                  1..12
                        mol_type = protein
                        organism = synthetic construct
SEQUENCE: 13
WRGEGYYAYF DV                                                        12

SEQ ID NO: 14           moltype = AA   length = 15
FEATURE                 Location/Qualifiers
source                  1..15
                        mol_type = protein
                        organism = synthetic construct
SEQUENCE: 14
KASQSVDYQG DSYMN                                                     15

SEQ ID NO: 15           moltype = AA   length = 7
FEATURE                 Location/Qualifiers
source                  1..7
                        mol_type = protein
                        organism = synthetic construct
SEQUENCE: 15
AASNLES                                                              7

SEQ ID NO: 16           moltype = AA   length = 9
FEATURE                 Location/Qualifiers
source                  1..9
                        mol_type = protein
                        organism = synthetic construct
SEQUENCE: 16
QQSNEDPYT                                                            9

SEQ ID NO: 17           moltype = AA   length = 10
FEATURE                 Location/Qualifiers
VARIANT                 3
                        note = Alanine or Threonine
VARIANT                 5
                        note = Serine or Threonine
VARIANT                 6
                        note = Asparagine or Serine
source                  1..10
                        mol_type = protein
                        organism = synthetic construct
SEQUENCE: 17
```

```
GYXFXXYLIE                                                                10

SEQ ID NO: 18           moltype = AA  length = 17
FEATURE                 Location/Qualifiers
VARIANT                 12
                        note = Asparagine or Alanine
VARIANT                 13
                        note = Glutamic Acid or Aspartic Acid
VARIANT                 14
                        note = Lysine or Serine
VARIANT                 15
                        note = Phenylalanine or Valine
source                  1..17
                        mol_type = protein
                        organism = synthetic construct
SEQUENCE: 18
VINPGSGGTN YXXXXKG                                                        17

SEQ ID NO: 19           moltype = AA  length = 12
FEATURE                 Location/Qualifiers
VARIANT                 4
                        note = Glutamic Acid or Aspartic Acid
source                  1..12
                        mol_type = protein
                        organism = synthetic construct
SEQUENCE: 19
WRGXGYYAYF DV                                                             12

SEQ ID NO: 20           moltype = AA  length = 15
FEATURE                 Location/Qualifiers
VARIANT                 1
                        note = Arginine or Lysine
VARIANT                 7
                        note = Serine or Aspartic Acid
VARIANT                 9
                        note = Aspartic Acid or Glutamine
source                  1..15
                        mol_type = protein
                        organism = synthetic construct
SEQUENCE: 20
XASQSVXYXG DSYMN                                                          15

SEQ ID NO: 21           moltype = AA  length = 7
FEATURE                 Location/Qualifiers
VARIANT                 6
                        note = Glutamic Acid or Alanine
source                  1..7
                        mol_type = protein
                        organism = synthetic construct
SEQUENCE: 21
AASNLXS                                                                   7

SEQ ID NO: 22           moltype = AA  length = 15
FEATURE                 Location/Qualifiers
VARIANT                 9
                        note = Any amino acid
VARIANT                 10
                        note = Any amino acid
source                  1..15
                        mol_type = protein
                        organism = synthetic construct
SEQUENCE: 22
KASQSVDYXX DSYMN                                                          15

SEQ ID NO: 23           moltype = AA  length = 451
FEATURE                 Location/Qualifiers
source                  1..451
                        mol_type = protein
                        organism = synthetic construct
SEQUENCE: 23
QVQLVESGGG VVQPGRSLRL SCAASGYTFS SYLIEWVRQA PGKGLEWVAV INPGSGGTNY          60
ADSVKGRFTI SADKSKNTAY LQMNSLRAED TAVYYCARWR GDGYYAYFDV WGQGTTVTVS          120
SASTKGPSVF PLAPSSKSTS GGTAALGCLV KDYFPEPVTV SWNSGALTSG VHTFPAVLQS          180
SGLYSLSSVV TVPSSSLGTQ TYICNVNHKP SNTKVDKRVE PKSCDKTHTC PPCPAPELLG          240
GPSVFLFPPK PKDTLMISRT PEVTCVVVDV SHEDPEVKFN WYVDGVEVHN AKTKPREEQY          300
NSTYRVVSVL TVLHQDWLNG KEYKCKVSNK ALPAPIEKTI SKAKGQPREP QVYTLPPSRE          360
EMTKNQVSLT CLVKGFYPSD IAVEWESNGQ PENNYKTTPP VLDSDGSFFL YSKLTVDKSR          420
WQQGNVFSCS VMHEALHNHY TQKSLSLSPG K                                        451
```

```
SEQ ID NO: 24              moltype = AA  length = 218
FEATURE                    Location/Qualifiers
source                     1..218
                           mol_type = protein
                           organism = synthetic construct
SEQUENCE: 24
EIVLTQSPAT LSVSPGERAT LSCRASQSVS YDGDSYMNWY QQKPGQAPRL LIYAASNLAS    60
GIPARFSGSG SGTEFTLTIS SLQSEDAAVY YCQQSNEDPY TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 25              moltype = AA  length = 121
FEATURE                    Location/Qualifiers
source                     1..121
                           mol_type = protein
                           organism = synthetic construct
SEQUENCE: 25
QVQLVESGGG VVQPGRSLRL SCAASGYTFS SYLIEWVRQA PGKGLEWVAV INPGSGGTNY    60
ADSVKGRFTI SADKSKNTAY LQMNSLRAED TAVYYCARWR GDGYYAYFDV WGQGTTVTVS   120
S                                                                  121

SEQ ID NO: 26              moltype = AA  length = 111
FEATURE                    Location/Qualifiers
source                     1..111
                           mol_type = protein
                           organism = synthetic construct
SEQUENCE: 26
EIVLTQSPAT LSVSPGERAT LSCRASQSVS YDGDSYMNWY QQKPGQAPRL LIYAASNLAS    60
GIPARFSGSG SGTEFTLTIS SLQSEDAAVY YCQQSNEDPY TFGGGTKVEI K            111

SEQ ID NO: 27              moltype = AA  length = 10
FEATURE                    Location/Qualifiers
source                     1..10
                           mol_type = protein
                           organism = synthetic construct
SEQUENCE: 27
GYTFSSYLIE                                                          10

SEQ ID NO: 28              moltype = AA  length = 17
FEATURE                    Location/Qualifiers
source                     1..17
                           mol_type = protein
                           organism = synthetic construct
SEQUENCE: 28
VINPGSGGTN YADSVKG                                                  17

SEQ ID NO: 29              moltype = AA  length = 12
FEATURE                    Location/Qualifiers
source                     1..12
                           mol_type = protein
                           organism = synthetic construct
SEQUENCE: 29
WRGDGYYAYF DV                                                       12

SEQ ID NO: 30              moltype = AA  length = 15
FEATURE                    Location/Qualifiers
source                     1..15
                           mol_type = protein
                           organism = synthetic construct
SEQUENCE: 30
RASQSVSYDG DSYMN                                                    15

SEQ ID NO: 31              moltype = AA  length = 7
FEATURE                    Location/Qualifiers
source                     1..7
                           mol_type = protein
                           organism = synthetic construct
SEQUENCE: 31
AASNLAS                                                             7

SEQ ID NO: 32              moltype = AA  length = 9
FEATURE                    Location/Qualifiers
source                     1..9
                           mol_type = protein
                           organism = synthetic construct
SEQUENCE: 32
QQSNEDPYT                                                           9

SEQ ID NO: 33              moltype = AA  length = 15
```

```
FEATURE                 Location/Qualifiers
VARIANT                 9
                        note = Any amino acid
VARIANT                 10
                        note = Any amino acid
source                  1..15
                        mol_type = protein
                        organism = synthetic construct
SEQUENCE: 33
RASQSVSYXX DSYMN                                                         15

SEQ ID NO: 34           moltype = AA  length = 447
FEATURE                 Location/Qualifiers
source                  1..447
                        mol_type = protein
                        organism = synthetic construct
SEQUENCE: 34
EVQLVQSGAE VKKPGESLKI SCKGSGYSFT NFYIHWVRQA PGQRLEWMGS IYPNYGDTAY         60
NQKFKDRFVF SLDTSVSTAY LQISSLKAED TAVYYCARGY SYAMDYWGQG TTVTVSSAST         120
KGPSVFPLAP SSKSTSGGTA ALGCLVKDYF PEPVTVSWNS GALTSGVHTF PAVLQSSGLY         180
SLSSVVTVPS SSLGTQTYIC NVNHKPSNTK VDKKVEPKSC DKTHTCPPCP APELLGGPSV         240
FLFPPKPKDT LMISRTPEVT CVVVDVSHED PEVKFNWYVD GVEVHNAKTK PREEQYNSTY         300
RVVSVLTVLH QDWLNGKEYK CKVSNKALPA PIEKTISKAK GQPREPQVYT LPPSRDELTK         360
NQVSLTCLVK GFYPSDIAVE WESNGQPENN YKTTPPVLDS DGSFFLYSKL TVDKSRWQQG         420
NVFSCSVMHE ALHNHYTQKS LSLSPGK                                            447

SEQ ID NO: 35           moltype = AA  length = 214
FEATURE                 Location/Qualifiers
source                  1..214
                        mol_type = protein
                        organism = synthetic construct
SEQUENCE: 35
DIQMTQSPSS VSASVGDRVT ITCSASQGIS GDLNWYQQKP GKAPKLLIYH TSSLHSGVPS         60
RFSGSGSGTD FTLTISSLQP EDFATYYCQY YSKDLLEIKRTV AAPSVFIFPP                  120
SDEQLKSGTA SVVCLLNNFY PREAKVQWKV DNALQSGNSQ ESVTEQDSKD STYSLSSTLT         180
LSKADYEKHK VYACEVTHQG LSSPVTKSFN RGEC                                    214

SEQ ID NO: 36           moltype = AA  length = 117
FEATURE                 Location/Qualifiers
source                  1..117
                        mol_type = protein
                        organism = synthetic construct
SEQUENCE: 36
EVQLVQSGAE VKKPGESLKI SCKGSGYSFT NFYIHWVRQA PGQRLEWMGS IYPNYGDTAY         60
NQKFKDRFVF SLDTSVSTAY LQISSLKAED TAVYYCARGY SYAMDYWGQG TTVTVSS           117

SEQ ID NO: 37           moltype = AA  length = 107
FEATURE                 Location/Qualifiers
source                  1..107
                        mol_type = protein
                        organism = synthetic construct
SEQUENCE: 37
DIQMTQSPSS VSASVGDRVT ITCSASQGIS GDLNWYQQKP GKAPKLLIYH TSSLHSGVPS         60
RFSGSGSGTD FTLTISSLQP EDFATYYCQY YSKDLLTFGG GTKLEIK                      107

SEQ ID NO: 38           moltype = AA  length = 10
FEATURE                 Location/Qualifiers
source                  1..10
                        mol_type = protein
                        organism = synthetic construct
SEQUENCE: 38
GYSFTNFYIH                                                               10

SEQ ID NO: 39           moltype = AA  length = 17
FEATURE                 Location/Qualifiers
source                  1..17
                        mol_type = protein
                        organism = synthetic construct
SEQUENCE: 39
SIYPNYGDTA YNQKFKD                                                       17

SEQ ID NO: 40           moltype = AA  length = 8
FEATURE                 Location/Qualifiers
source                  1..8
                        mol_type = protein
                        organism = synthetic construct
SEQUENCE: 40
GYSYAMDY                                                                 8
```

-continued

```
SEQ ID NO: 41          moltype = AA  length = 15
FEATURE                Location/Qualifiers
source                 1..15
                       mol_type = protein
                       organism = synthetic construct
SEQUENCE: 41
VTITCSASQG ISGDL                                                    15

SEQ ID NO: 42          moltype = AA  length = 7
FEATURE                Location/Qualifiers
source                 1..7
                       mol_type = protein
                       organism = synthetic construct
SEQUENCE: 42
HTSSLHS                                                              7

SEQ ID NO: 43          moltype = AA  length = 9
FEATURE                Location/Qualifiers
source                 1..9
                       mol_type = protein
                       organism = synthetic construct
SEQUENCE: 43
QYYSKDLLT                                                            9

SEQ ID NO: 44          moltype = AA  length = 15
FEATURE                Location/Qualifiers
VARIANT                9
                       note = Any amino acid
VARIANT                10
                       note = Any amino acid
source                 1..15
                       mol_type = protein
                       organism = synthetic construct
SEQUENCE: 44
VTITCSASXX ISGDL                                                    15

SEQ ID NO: 45          moltype =     length =
SEQUENCE: 45
000

SEQ ID NO: 46          moltype =     length =
SEQUENCE: 46
000

SEQ ID NO: 47          moltype =     length =
SEQUENCE: 47
000

SEQ ID NO: 48          moltype = AA  length = 4
FEATURE                Location/Qualifiers
source                 1..4
                       mol_type = protein
                       organism = synthetic construct
SEQUENCE: 48
GGGG                                                                 4

SEQ ID NO: 49          moltype = AA  length = 5
FEATURE                Location/Qualifiers
source                 1..5
                       mol_type = protein
                       organism = synthetic construct
SEQUENCE: 49
GGGGS                                                                5

SEQ ID NO: 50          moltype = AA  length = 6
FEATURE                Location/Qualifiers
source                 1..6
                       mol_type = protein
                       organism = synthetic construct
SEQUENCE: 50
GGGGSG                                                               6

SEQ ID NO: 51          moltype = AA  length = 7
FEATURE                Location/Qualifiers
source                 1..7
                       mol_type = protein
                       organism = synthetic construct
SEQUENCE: 51
GGGGSGG                                                              7
```

```
SEQ ID NO: 52            moltype = AA   length = 13
FEATURE                  Location/Qualifiers
source                   1..13
                         mol_type = protein
                         organism = synthetic construct
SEQUENCE: 52
GGGGSGGGGS GGG                                                            13

SEQ ID NO: 53            moltype = AA   length = 14
FEATURE                  Location/Qualifiers
source                   1..14
                         mol_type = protein
                         organism = synthetic construct
SEQUENCE: 53
GGGGSGGGGS GGGG                                                           14

SEQ ID NO: 54            moltype = AA   length = 19
FEATURE                  Location/Qualifiers
source                   1..19
                         mol_type = protein
                         organism = synthetic construct
SEQUENCE: 54
GGGGSGGGGS GGGGSGGGG                                                      19

SEQ ID NO: 55            moltype = AA   length = 20
FEATURE                  Location/Qualifiers
source                   1..20
                         mol_type = protein
                         organism = synthetic construct
SEQUENCE: 55
GGGGSGGGGS GGGGSGGGGS                                                     20

SEQ ID NO: 56            moltype = AA   length = 349
FEATURE                  Location/Qualifiers
source                   1..349
                         mol_type = protein
                         organism = synthetic construct
SEQUENCE: 56
AIRLTQSPSS FSASTGDRVT ITCKASQSVD YNFHLRPRDL ISNINVIVLE LKGSETTFMC          60
EYADETATIV EFLNRWITFS QSIISTLTPT SSSTKKTQLQ LEHLLLDLQM ILNGINNYKN         120
PKLTRMLTFK FYMPKKATEL KHLQCLEEEL KPLEEVLNLA QSKGDSYMNW YQQKPGKAPK         180
LLIYAASNLE SGVPSRFSGS GSGTDFTLTI SSLQSEDFAT YYCQQSNEDP YTFGGGTKVE         240
IKRTVAAPSV FIFPPSDEQL KSGTASVVCL LNNFYPREAK VQWKVDNALQ SGNSQESVTE         300
QDSKDSTYSL SSTLTLSKAD YEKHKVYACE VTHQGLSSPV TKSFNRGEC                    349

SEQ ID NO: 57            moltype = AA   length = 353
FEATURE                  Location/Qualifiers
source                   1..353
                         mol_type = protein
                         organism = synthetic construct
SEQUENCE: 57
AIRLTQSPSS FSASTGDRVT ITCKASQSVD YGGNFHLRPR DLISNINVIV LELKGSETTF          60
MCEYADETAT IVEFLNRWIT FSQSIISTLT PTSSSTKKTQ LQLEHLLLDL QMILNGINNY         120
KNPKLTRMLT FKFYMPKKAT ELKHLQCLEE ELKPLEEVLN LAQSKGGGDS YMNWYQQKPG         180
KAPKLLIYAA SNLESGVPSR FSGSGSGTDF TLTISSLQSE DFATYYCQQS NEDPYTFGGG         240
TKVEIKRTVA APSVFIFPPS DEQLKSGTAS VVCLLNNFYP REAKVQWKVD NALQSGNSQE         300
SVTEQDSKDS TYSLSSTLTL SKADYEKHKV YACEVTHQGL SSPVTKSFNR GEC                353

SEQ ID NO: 58            moltype = AA   length = 355
FEATURE                  Location/Qualifiers
source                   1..355
                         mol_type = protein
                         organism = synthetic construct
SEQUENCE: 58
AIRLTQSPSS FSASTGDRVT ITCKASQSVD YGGGNFHLRP RDLISNINVI VLELKGSETT          60
FMCEYADETA TIVEFLNRWI TFSQSIISTL TPTSSSTKKT QLQLEHLLLD LQMILNGINN         120
YKNPKLTRML TFKFYMPKKA TELKHLQCLE EELKPLEEVL NLAQSKGGGD SYMNWYQQK          180
PGKAPKLLIY AASNLESGVP SRFSGSGSGT DFTLTISSLQ SEDFATYYCQ QSNEDPYTFG         240
GGTKVEIKRT VAAPSVFIFP PSDEQLKSGT ASVVCLLNNF YPREAKVQWK VDNALQSGNS         300
QESVTEQDSK DSTYSLSSTL TLSKADYEKH KVYACEVTHQ GLSSPVTKSF NRGEC              355

SEQ ID NO: 59            moltype = AA   length = 357
FEATURE                  Location/Qualifiers
source                   1..357
                         mol_type = protein
                         organism = synthetic construct
SEQUENCE: 59
AIRLTQSPSS FSASTGDRVT ITCKASQSVD YGGGGNFHLR PRDLISNINV IVLELKGSET          60
```

```
TFMCEYADET ATIVEFLNRW ITFSQSIIST LTPTSSSTKK TQLQLEHLLL DLQMILNGIN    120
NYKNPKLTRM LTFKFYMPKK ATELKHLQCL EEELKPLEEV LNLAQSKGGG GSDSYMNWYQ    180
QKPGKAPKLL IYAASNLESG VPSRFSGSGS GTDFTLTISS LQSEDFATYY CQQSNEDPYT    240
FGGGTKVEIK RTVAAPSVFI FPPSDEQLKS GTASVVCLLN NFYPREAKVQ WKVDNALQSG    300
NSQESVTEQD SKDSTYSLSS TLTLSKADYE KHKVYACEVT HQGLSSPVTK SFNRGEC       357

SEQ ID NO: 60           moltype = AA   length = 361
FEATURE                 Location/Qualifiers
source                  1..361
                        mol_type = protein
                        organism = synthetic construct
SEQUENCE: 60
AIRLTQSPSS FSASTGDRVT ITCKASQSVD YGGGGSGNFH LRPRDLISNI NVIVLELKGS     60
ETTFMCEYAD ETATIVEFLN RWITFSQSII STLTPTSSST KKTQLQLEHL LLDLQMILNG    120
INNYKNPKLT RMLTFKFYMP KKATELKHLQ CLEEELKPLE EVLNLAQSKG GGSGGDSYM     180
NWYQQKPGKA PKLLIYAASN LESGVPSRFS GSGSGTDFTL TISSLQSEDF ATYYCQQSNE    240
DPYTFGGGTK VEIKRTVAAP SVFIFPPSDE QLKSGTASVV CLLNNFYPRE AKVQWKVDNA    300
LQSGNSQESV TEQDSKDSTY SLSSTLTLSK ADYEKHKVYA CEVTHQGLSS PVTKSFNRGE    360
C                                                                   361

SEQ ID NO: 61           moltype = AA   length = 375
FEATURE                 Location/Qualifiers
source                  1..375
                        mol_type = protein
                        organism = synthetic construct
SEQUENCE: 61
AIRLTQSPSS FSASTGDRVT ITCKASQSVD YGGGGSGGGG SGGGNFHLRP RDLISNINVI     60
VLELKGSETT FMCEYADETA TIVEFLNRWI TFSQSIISTL TPTSSSTKKT QLQLEHLLLD    120
LQMILNGINN YKNPKLTRML TFKFYMPKKA TELKHLQCLE EELKPLEEVL NLAQSKGGGG    180
SGGGGSGGGG DSYMNWYQQK PGKAPKLLIY AASNLESGVP SRFSGSGSGT DFTLTISSLQ    240
SEDFATYYCQ QSNEDPYTFG GGTKVEIKRT VAAPSVFIFP PSDEQLKSGT ASVVCLLNNF    300
YPREAKVQWK VDNALQSGNS QESVTEQDSK DSTYSLSSTL TLSKADYEKH KVYACEVTHQ    360
GLSSPVTKSF NRGEC                                                    375

SEQ ID NO: 62           moltype = AA   length = 387
FEATURE                 Location/Qualifiers
source                  1..387
                        mol_type = protein
                        organism = synthetic construct
SEQUENCE: 62
AIRLTQSPSS FSASTGDRVT ITCKASQSVD YGGGGSGGGG SGGGGSGGGG NFHLRPRDLI     60
SNINVIVLEL KGSETTFMCE YADETATIVE FLNRWITFSQ SIISTLTPTS SSTKKTQLQL    120
EHLLLDLQMI LNGINNYKNP KLTRMLTFKF YMPKKATELK HLQCLEEELK PLEEVLNLAQ    180
SKGGGGSGGG GSGGGGSGGG GSDSYMNWYQ QKPGKAPKLL IYAASNLESG VPSRFSGSGS    240
GTDFTLTISS LQSEDFATYY CQQSNEDPYT FGGGTKVEIK RTVAAPSVFI FPPSDEQLKS    300
GTASVVCLLN NFYPREAKVQ WKVDNALQSG NSQESVTEQD SKDSTYSLSS TLTLSKADYE    360
KHKVYACEVT HQGLSSPVTK SFNRGEC                                        387

SEQ ID NO: 63           moltype = AA   length = 349
FEATURE                 Location/Qualifiers
source                  1..349
                        mol_type = protein
                        organism = synthetic construct
SEQUENCE: 63
EIVLTQSPAT LSVSPGERAT LSCRASQSVS YNFHLRPRDL ISNINVIVLE LKGSETTFMC     60
EYADETATIV EFLNRWITFS QSIISTLTPT SSSTKKTQLQ LEHLLLDLQM ILNGINNYKN    120
PKLTRMLTFK FYMPKKATEL KHLQCLEEEL KPLEEVLNLA QSKGDSYMNW YQQKPGAPR     180
LLIYAASNLA SGIPARFSGS GSGTEFTLTI SSLQSEDAAV YYCQQSNEDP YTFGGGTKVE    240
IKRTVAAPSV FIFPPSDEQL KSGTASVVCL LNNFYPREAK VQWKVDNALQ SGNSQESVTE    300
QDSKDSTYSL SSTLTLSKAD YEKHKVYACE VTHQGLSSPV TKSFNRGEC                349

SEQ ID NO: 64           moltype = AA   length = 353
FEATURE                 Location/Qualifiers
source                  1..353
                        mol_type = protein
                        organism = synthetic construct
SEQUENCE: 64
EIVLTQSPAT LSVSPGERAT LSCRASQSVS YGGNFHLRPR DLISNINVIV LELKGSETTF     60
MCEYADETAT IVEFLNRWIT FSQSIISTLT PTSSSTKKTQ LQLEHLLLDL QMILNGINNY    120
KNPKLTRMLT FKFYMPKKAT ELKHLQCLEE ELKPLEEVLN LAQSKGGGDS YMNWYQQKPG    180
QAPRLLIYAA SNLASGIPAR FSGSGSGTEF TLTISSLQSE DAAVYYCQQS NEDPYTFGGG    240
TKVEIKRTVA APSVFIFPPS DEQLKSGTAS VVCLLNNFYP REAKVQWKVD NALQSGNSQE    300
SVTEQDSKDS TYSLSSTLTL SKADYEKHKV YACEVTHQGL SSPVTKSFNR GEC           353

SEQ ID NO: 65           moltype = AA   length = 355
FEATURE                 Location/Qualifiers
source                  1..355
                        mol_type = protein
                        organism = synthetic construct
```

```
SEQUENCE: 65
EIVLTQSPAT LSVSPGERAT LSCRASQSVS YGGGNFHLRP RDLISNINVI VLELKGSETT    60
FMCEYADETA TIVEFLNRWI TFSQSIISTL TPTSSSTKKT QLQLEHLLLD LQMILNGINN   120
YKNPKLTRML TFKFYMPKKA TELKHLQCLE EELKPLEEVL NLAQSKGGGG DSYMNWYQQK   180
PGQAPRLLIY AASNLASGIP ARFSGSGSGT EFTLTISSLQ SEDAAVYYCQ QSNEDPYTFG   240
GGTKVEIKRT VAAPSVFIFP PSDEQLKSGT ASVVCLLNNF YPREAKVQWK VDNALQSGNS   300
QESVTEQDSK DSTYSLSSTL TLSKADYEKH KVYACEVTHQ GLSSPVTKSF NRGEC        355

SEQ ID NO: 66          moltype = AA   length = 361
FEATURE                Location/Qualifiers
source                 1..361
                       mol_type = protein
                       organism = synthetic construct
SEQUENCE: 66
EIVLTQSPAT LSVSPGERAT LSCRASQSVS YGGGGSGNFH LRPRDLISNI NVIVLELKGS    60
ETTFMCEYAD ETATIVEFLN RWITFSQSII STLTPTSSST KKTQLQLEHL LLDLQMILNG   120
INNYKNPKLT RMLTFKFYMP KKATELKHLQ CLEEELKPLE EVLNLAQSKG GGGSGGDSYM   180
NWYQQKPGQA PRLLIYAASN LASGIPARFS GSGSGTEFTL TISSLQSEDA AVYYCQQSNE   240
DPYTFGGGTK VEIKRTVAAP SVFIFPPSDE QLKSGTASVV CLLNNFYPRE AKVQWKVDNA   300
LQSGNSQESV TEQDSKDSTY SLSSTLTLSK ADYEKHKVYA CEVTHQGLSS PVTKSFNRGE   360
C                                                                  361

SEQ ID NO: 67          moltype = AA   length = 375
FEATURE                Location/Qualifiers
source                 1..375
                       mol_type = protein
                       organism = synthetic construct
SEQUENCE: 67
EIVLTQSPAT LSVSPGERAT LSCRASQSVS YGGGGSGGGG SGGGNFHLRP RDLISNINVI    60
VLELKGSETT FMCEYADETA TIVEFLNRWI TFSQSIISTL TPTSSSTKKT QLQLEHLLLD   120
LQMILNGINN YKNPKLTRML TFKFYMPKKA TELKHLQCLE EELKPLEEVL NLAQSKGGGG   180
SGGGGSGGGG DSYMNWYQQK PGQAPRLLIY AASNLASGIP ARFSGSGSGT EFTLTISSLQ   240
SEDAAVYYCQ QSNEDPYTFG GGTKVEIKRT VAAPSVFIFP PSDEQLKSGT ASVVCLLNNF   300
YPREAKVQWK VDNALQSGNS QESVTEQDSK DSTYSLSSTL TLSKADYEKH KVYACEVTHQ   360
GLSSPVTKSF NRGEC                                                   375

SEQ ID NO: 68          moltype = AA   length = 347
FEATURE                Location/Qualifiers
source                 1..347
                       mol_type = protein
                       organism = synthetic construct
SEQUENCE: 68
DIQMTQSPSS VSASVGDRVT ITCSASQGIS GNFHLRPRDL ISNINVIVLE LKGSETTFMC    60
EYADETATIV EFLNRWITFS QSIISTLTPT SSSTKKTQLQ LEHLLLDLQM ILNGINNYKN   120
PKLTRMLTFK FYMPKKATEL KHLQCLEEEL KPLEEVLNLA QSKGDLNWYQ QKPGKAPKLL   180
IYHTSSLHSG VPSRFSGSGS GTDFTLTISS LQPEDFATYY CQYYSKDLLT FGGGTKLEIK   240
RTVAAPSVFI FPPSDEQLKS GTASVVCLLN NFYPREAKVQ WKVDNALQSG NSQESVTEQD   300
SKDSTYSLSS TLTLSKADYE KHKVYACEVT HQGLSSPVTK SFNRGEC                 347

SEQ ID NO: 69          moltype = AA   length = 351
FEATURE                Location/Qualifiers
source                 1..351
                       mol_type = protein
                       organism = synthetic construct
SEQUENCE: 69
DIQMTQSPSS VSASVGDRVT ITCSASQGIS GGGNFHLRPR DLISNINVIV LELKGSETTF    60
MCEYADETAT IVEFLNRWIT FSQSIISTLT PTSSSTKKTQ LQLEHLLLDL QMILNGINNY   120
KNPKLTRMLT FKFYMPKKAT ELKHLQCLEE ELKPLEEVLN LAQSKGGGDL NWYQQKPGKA   180
PKLLIYHTSS LHSGVPSRFS GSGSGTDFTL TISSLQPEDF ATYYCQYYSK DLLTFGGGTK   240
LEIKRTVAAP SVFIFPPSDE QLKSGTASVV CLLNNFYPRE AKVQWKVDNA LQSGNSQESV   300
TEQDSKDSTY SLSSTLTLSK ADYEKHKVYA CEVTHQGLSS PVTKSFNRGE C            351

SEQ ID NO: 70          moltype = AA   length = 353
FEATURE                Location/Qualifiers
source                 1..353
                       mol_type = protein
                       organism = synthetic construct
SEQUENCE: 70
DIQMTQSPSS VSASVGDRVT ITCSASQGIS GGGGNFHLRP RDLISNINVI VLELKGSETT    60
FMCEYADETA TIVEFLNRWI TFSQSIISTL TPTSSSTKKT QLQLEHLLLD LQMILNGINN   120
YKNPKLTRML TFKFYMPKKA TELKHLQCLE EELKPLEEVL NLAQSKGGGG DLNWYQQKPG   180
KAPKLLIYHT SSLHSGVPSR FSGSGSGTDF TLTISSLQPE DFATYYCQYY SKDLLTFGGG   240
TKLEIKRTVA APSVFIFPPS DEQLKSGTAS VVCLLNNFYP REAKVQWKVD NALQSGNSQE   300
SVTEQDSKDS TYSLSSTLTL SKADYEKHKV YACEVTHQGL SSPVTKSFNR GEC          353

SEQ ID NO: 71          moltype = AA   length = 359
FEATURE                Location/Qualifiers
source                 1..359
                       mol_type = protein
```

```
                        organism = synthetic construct
SEQUENCE: 71
DIQMTQSPSS VSASVGDRVT ITCSASQGIS GGGGGSGNFH LRPRDLISNI NVIVLELKGS      60
ETTFMCEYAD ETATIVEFLN RWITFSQSII STLTPTSSST KKTQLQLEHL LLDLQMILNG     120
INNYKNPKLT RMLTFKFYMP KKATELKHLQ CLEEELKPLE EVLNLAQSKG GGGSGGDLNW     180
YQQKPGKAPK LLIYHTSSLH SGVPSRFSGS GSGTDFTLTI SSLQPEDFAT YYCQYYSKDL     240
LTFGGGTKLE IKRTVAAPSV FIFPPSDEQL KSGTASVVCL LNNFYPREAK VQWKVDNALQ     300
SGNSQESVTE QDSKDSTYSL SSTLTLSKAD YEKHKVYACE VTHQGLSSPV TKSFNRGEC      359

SEQ ID NO: 72           moltype = AA  length = 373
FEATURE                 Location/Qualifiers
source                  1..373
                        mol_type = protein
                        organism = synthetic construct
SEQUENCE: 72
DIQMTQSPSS VSASVGDRVT ITCSASQGIS GGGGGSGGGG SGGGNFHLRP RDLISNINVI      60
VLELKGSETT FMCEYADETA TIVEFLNRWI TFSQSIISTL TPTSSSTKKT QLQLEHLLLD     120
LQMILNGINN YKNPKLTRML TFKFYMPKKA TELKHLQCLE EELKPLEEVL NLAQSKGGGG     180
SGGGGSGGGG DLNWYQQKPG KAPKLLIYHT SSLHSGVPSR FSGSGSGTDF TLTISSLQPE     240
DFATYYCQYY SKDLLTFGGG TKLEIKRTVA APSVFIFPPS DEQLKSGTAS VVCLLNNFYP     300
REAKVQWKVD NALQSGNSQE SVTEQDSKDS TYSLSSTLTL SKADYEKHKV YACEVTHQGL     360
SSPVTKSFNR GEC                                                        373

SEQ ID NO: 73           moltype = AA  length = 330
FEATURE                 Location/Qualifiers
source                  1..330
                        mol_type = protein
                        organism = synthetic construct
SEQUENCE: 73
ASTKGPSVFP LAPSSKSTSG GTAALGCLVK DYFPEPVTVS WNSGALTSGV HTFPAVLQSS       60
GLYSLSSVVT VPSSSLGTQT YICNVNHKPS NTKVDKKVEP KSCDKTHTCP PCPAPELLGG     120
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSREE     240
MTKNQVSLTC LVKGFYPSDI AVEWESNGQP ENNYKTTPPV LDSDGSFFLY SKLTVDKSRW     300
QQGNVFSCSV MHEALHNHYT QKSLSLSPGK                                      330

SEQ ID NO: 74           moltype = DNA  length = 990
FEATURE                 Location/Qualifiers
source                  1..990
                        mol_type = other DNA
                        organism = synthetic construct
SEQUENCE: 74
gcgtcgacca agggcccag  cgtgttcccc ctggccccca gcagcaagag caccagcggc       60
ggcacagccg ccctgggctg cctggtgaag gactacttcc ccgagcccgt gaccgtgtcc     120
tggaacagcg gagccctgac ctccggcgtg cacaccttcc ccgccgtgct gcagagcagc     180
ggcctgtaca gcctgtccag cgtggtgaca gtgcccagca gcagcctggg cacccagacc     240
tacatctgca acgtgaacca caagcccagc aacaccaagg tggacaagaa agtggagccc     300
aagagctgcg acaagaccca cacctgcccc cctgcccag  ccccagagct gctgggcgga     360
ccctccgtgt tcctgttccc ccccaagccc aaggacaccc tgatgatcag caggaccccc     420
gaggtgacct gcgtggtggt ggacgtgagc cacgaggacc cagaggtgaa gttcaactgg     480
tacgtggacg gcgtggaggt gcacaacgcc aagaccaagc ccagagagga gcagtacaac     540
agcacctaca gggtggtgtc cgtgctgacc gtgctgcacc aggactggct gaacggcaag     600
gaatacaagt gcaaggtctc caacaaggcc ctgccagccc catcgaaaa  gaccatcagc     660
aaggccaagg gccagccacg ggagcccag  gtgtacaccc tgcccccctc ccgggaggag     720
atgaccaaga accaggtgtc cctgacctgt ctggtgaagg gcttctaccc cagcgacatc     780
gccgtggagt gggagagcaa cggccagccc gagaacaact acaagaccac cccccccagtg    840
ctggacagcg acggcagctt cttcctgtac agcaagctga ccgtggacaa gtccaggtgg     900
cagcagggca acgtgttcag ctgcagcgtg atgcacgagg ccctgcacaa ccactacacc     960
cagaagagcc tgagcctgtc ccccggcaag                                      990

SEQ ID NO: 75           moltype = AA  length = 326
FEATURE                 Location/Qualifiers
source                  1..326
                        mol_type = protein
                        organism = synthetic construct
SEQUENCE: 75
ASTKGPSVFP LAPCSRSTSE STAALGCLVK DYFPEPVTVS WNSGALTSGV HTFPAVLQSS       60
GLYSLSSVVT VPSSNFGTQT YTCNVDHKPS NTKVDKTVER KCCVECPPCP APPVAGPSVF     120
LFPPKPKDTL MISRTPEVTC VVVDVSHEDP EVQFNWYVDG VEVHNAKTKP REEQFNSTFR     180
VVSVLTVVHQ DWLNGKEYKC KVSNKGLPAP IEKTISKTKG QPREPQVYTL PPSREEMTKN     240
QVSLTCLVKG FYPSDIAVEW ESNGQPENNY KTTPPMLDSD GSFFLYSKLT VDKSRWQQGN     300
VFSCSVMHEA LHNHYTQKSL SLSPGK                                          326

SEQ ID NO: 76           moltype = DNA  length = 978
FEATURE                 Location/Qualifiers
source                  1..978
                        mol_type = other DNA
                        organism = synthetic construct
SEQUENCE: 76
```

```
gccagcacca agggcccag cgtgttcccc ctggcccct gcagcagaag caccagcgag    60
agcacagccg ccctgggctg cctggtgaag gactacttcc ccgagccagt gaccgtgtcc   120
tggaacagcg gagccctgac cagcggcgtg cacaccttcc ccgccgtgct gcagagcagc   180
ggcctgtaca gcctgtccag cgtggtgacc gtgcccagca gcaacttcgg cacccagacc   240
tacacctgca acgtggacca caagcccagc aacaccaagg tggacaagac cgtggagagg   300
aagtgctgcg tggagtgccc ccctgccca gccccccag tggccggacc ctccgtgttc     360
ctgttccccc ccaagcccaa ggacaccctg atgatcagca ggaccccga ggtgacctgc    420
gtggtggtgg acgtgagcca cgaggaccca gaggtgcagt tcaactggta cgtggacggc   480
gtggaggtgc acaacgccaa gaccaagccc agagaggaac agtttaacag caccttcagg   540
gtggtgtccg tgctgaccgt ggtgcaccag gactggctga acggcaaaga gtacaagtgc   600
aaggtctcca acaagggcct gccagccccc atcgagaaaa ccatcagcaa gaccaagggc   660
cagccacggg agcccaggt gtacaccctg ccccccagcc gggaggaaat gaccaagaac    720
caggtgtccc tgacctgtct ggtgaaggc ttctacccca gcgacatcgc cgtggagtgg    780
gagagcaacg gccagcccga gaacaactac aagacccccc ccatgctgga cagcgac      840
ggcagcttct tcctgtacag caagctgaca gtggacaaga gcaggtggca gcagggcaac   900
gtgttcagct gcagcgtgat gcacgaggcc ctgcacaacc actacaccca gaagagcctg   960
agcctgtccc ccggcaag                                                  978

SEQ ID NO: 77          moltype = AA   length = 377
FEATURE                Location/Qualifiers
source                 1..377
                       mol_type = protein
                       organism = synthetic construct
SEQUENCE: 77
ASTKGPSVFP LAPCSRSTSG GTAALGCLVK DYFPEPVTVS WNSGALTSGV HTFPAVLQSS    60
GLYSLSSVVT VPSSSLGTQT YTCNVNHKPS NTKVDKRVEL KTPLGDTTHT CPRCPEPKSC   120
DTPPPCPRCP EPKSCDTPPP CPRCPEPKSC DTPPPCPRCP APELLGGPSV FLFPPKPKDT   180
LMISRTPEVT CVVVDVSHED PEVQFKWYVD GVEVHNAKTK PREEQYNSTF RVVSVLTVLH   240
QDWLNGKEYK CKVSNKALPA PIEKTISKTK GQPREPQVYT LPPSREEMTK NQVSLTCLVK   300
GFYPSDIAVE WESSGQPENN YNTTPPMLDS DGSFFLYSKL TVDKSRWQQG NIFSCSVMHE   360
ALHNRFTQKS LSLSPGK                                                   377

SEQ ID NO: 78          moltype = DNA  length = 1131
FEATURE                Location/Qualifiers
source                 1..1131
                       mol_type = other DNA
                       organism = synthetic construct
SEQUENCE: 78
gccagcacca agggcccag cgtgttcccc ctggcccct gcagccggag caccagcggc     60
ggcaccgccg ccctgggctg cctggtgaag gactacttcc ccgagccgt gaccgtgagc   120
tggaacagcg gcgccctgac cagcggcgtg cacaccttcc ccgccgtgct gcagagcagc   180
ggcctgtaca gcctgagcag cgtggtgacc gtgcccagca gcagcctggg cacccagacc   240
tacacctgca acgtgaacca caagcccagc aacaccaagg tggacaagac ggtggagctg   300
aagaccccc tgggcgacac cacccacacc tgccccggt gccccgagcc caagagctgc    360
gacacccccc cccctgccc ccggtgcccc gagcccaaga gctgcgacac ccccccccc    420
tgccccggt gccccgagcc caagagctgc gacaccccc cccctgccc ccggtgcccc     480
gccccgagc tgctgggcgg ccccagcgtg ttcctgttcc ccccaagcc caaggacacc   540
ctgatgatca gccggacccc cgaggtgacc tgcgtggtgg tggacgtgag ccacgaggac   600
cccgaggtgc agttcaagtg gtacgtggac ggcgtggagg tgcacaacgc caagaccaag   660
ccccgggagg agcagtacaa cagcaccttc cgggtggtga gcgtgctgac cgtgctgcac   720
caggactggc tgaacggcaa ggagtacaag tgcaaggtga acaacaagc cctgccggcc    780
cccatcgaga agaccatcag caagaccaag ggccagcccc gggagcccca ggtgtacacc   840
ctgcccccca gccgggagga gatgaccaag aaccaggtga gcctgacctg cctggtgaag   900
ggcttctacc ccagcgacat cgccgtggag tgggagagca cgcgcagcc cgagaacaac   960
tacaacacca ccccccccat gctggacagc gacggcagct tcttcctgta cagcaagctg   1020
accgtggaca agagccggtg gcagcagggc aacatcttca gctgcagcgt gatgcacgag   1080
gccctgcaca accactcac ccagaagagc ctgagcctga gcccggcaa g              1131

SEQ ID NO: 79          moltype = AA   length = 327
FEATURE                Location/Qualifiers
source                 1..327
                       mol_type = protein
                       organism = synthetic construct
SEQUENCE: 79
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                        327

SEQ ID NO: 80          moltype = DNA  length = 981
FEATURE                Location/Qualifiers
source                 1..981
                       mol_type = other DNA
                       organism = synthetic construct
SEQUENCE: 80
gcctctacca agggcccag cgtgttcccc ctggcccct gcagcagaag caccagcgag     60
agcacagccg ccctgggctg cctggtgaag gactacttcc ccgagccagt gaccgtgtcc   120
```

```
tggaacagcg gagccctgac cagcggcgtg cacaccttcc ccgcgtgct gcagagcagc    180
ggcctgtaca gcctgtccag cgtggtgacc gtgcccagca gcagcctggg caccaagacc    240
tacacctgca acgtggacca caagcccagc aacaccaagg tggacaagag ggtggagagc    300
aagtacggcc accctgccc ctcttgccca gcccccgagt tcctgggcgg accctccgtg    360
ttcctgttcc ccccaagcc caaggacacc ctgatgatca gcaggacccc cgaggtgacc    420
tgcgtggtgg tggacgtgag ccaggaagat ccagaggtcc agttcaactg gtacgtggac    480
ggcgtggagg tgcacaacgc caagaccaag cccagagagg aacagtttaa cagcacctac    540
agggtggtgt ccgtgctgac cgtgctgcac caggactggc tgaacggcaa agagtacaag    600
tgcaaggtct ccaacaaggg cctgcccagc tccatcgaga aaaccatcag caaggccaag    660
ggccagccac gggagcccca ggtgtacacc ctgccaccct cccaggaaga gatgaccaag    720
aaccaggtgt ccctgacctg tctggtgaag ggcttctacc ccagcgacat cgccgtggag    780
tgggagagca cgccagcc cgagaacaac tacaagacca ccccccagt gctggacagc    840
gacggcagct tcttcctgta cagcaggctg accgtggaca agtccaggtg caggaaggc    900
aacgtctta gctgcagcgt gatgcacgag gccctgcaca ccactacac ccagaagagc    960
ctgagcctgt ccctgggcaa g                                            981

SEQ ID NO: 81              moltype = AA   length = 330
FEATURE                    Location/Qualifiers
source                     1..330
                           mol_type = protein
                           organism = synthetic construct
SEQUENCE: 81
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                   330

SEQ ID NO: 82              moltype = DNA  length = 990
FEATURE                    Location/Qualifiers
source                     1..990
                           mol_type = other DNA
                           organism = synthetic construct
SEQUENCE: 82
gcctccacca aggtccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagag agttgagccc    300
aaatcttgtg acaaaactca cacatgccca ccgtgcccag cacctgaagc agcgggggga    360
ccgtcagtct tcctcttccc cccaaaaccc aaggacaccc tcatgatctc ccggaccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gggtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                   990

SEQ ID NO: 83              moltype = AA   length = 330
FEATURE                    Location/Qualifiers
source                     1..330
                           mol_type = protein
                           organism = synthetic construct
SEQUENCE: 83
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                   330

SEQ ID NO: 84              moltype = DNA  length = 990
FEATURE                    Location/Qualifiers
source                     1..990
                           mol_type = other DNA
                           organism = synthetic construct
SEQUENCE: 84
gctagcacca agggcccctc cgtgttccct ctggcccct ccagcaagtc cacctctggc     60
ggcaccgccg ctctgggctg cctggtgaaa gactacttcc ccgagccgt gaccgtgtcc    120
tggaactctg gcgccctgac ctccggcgtg cacacctttc cagccgtgct gcagtcctca    180
ggcctgtact ccctgtcctc cgtggtgacc gtgccctcta gctctctggg cacccagacc    240
tacatctgca acgtgaacca caagcccctc aacaccaagg tggacaagcg ggtggaaccc    300
aagtcctgcg acaagaccca cacctgtccc cctgccctg ccctgaact gctgggcgga    360
ccttccgtgt tcctgttccc cccaaagccc aaggacaccc tgatgatctc ccggaccccc    420
```

```
gaagtgacct gcgtggtggt ggacgtgtcc cacgaggacc ctgaagtgaa gttcaattgg    480
tacgtggacg gcgtggaagt gcacaacgcc aagaccaagc ccagagagga acagtacgcc    540
tccacctacc gggtggtgtc tgtgctgacc gtgctgcacc aggactggct gaacggcaaa    600
gagtacaagt gcaaggtctc caacaaggcc ctgcctgccc catcgaaaa gaccatctcc     660
aaggccaagg gccagccccg cgagccacag gtgtacacac tgccccccag ccgggaagag    720
atgaccaagg accaggtgtc cctgacctgt ctggtcaaag gcttctaccc ctccgatatc    780
gccgtggagt gggagtccaa cggacagccc gagaacaact acaagaccac ccccctgtg    840
ctggactccg acggctcatt cttcctgtac tccaagctga ccgtggacaa gtcccggtgg    900
cagcagggca acgtgttctc ctgctccgtg atgcacgagg ccctgcacaa ccactacacc    960
cagaagtccc tgtccctgag ccccggcaag                                     990
```

SEQ ID NO: 85          moltype = AA  length = 330
FEATURE                Location/Qualifiers
source                 1..330
                       mol_type = protein
                       organism = synthetic construct
SEQUENCE: 85
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG    120
PSVFLFPPKP KDTLMISRTP EVTCVVVAVS HEDPEVKFNW YVDGVEVHNA KTKPREEQYN    180
STYRVVSVLT VLHQDWLNGK EYKCKVSNKA LAAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                     330

SEQ ID NO: 86          moltype = DNA  length = 990
FEATURE                Location/Qualifiers
source                 1..990
                       mol_type = other DNA
                       organism = synthetic construct
SEQUENCE: 86
```
gctagcacca agggcccag cgtgttcccc ctggcccca gcagcaagag caccagcggc    60
ggcacagccg ccctgggctg cctggtgaag gactacttcc ccgagcccgt gaccgtgtcc    120
tggaacagcg gagccctgac ctccggcgtg cacaccttcc ccgccgtgct gcagagcagc    180
ggcctgtaca gcctgtccag cgtggtgaca gtgcccagca gcgcctgggg cacccagacc    240
tacatctgca acgtgaacca caagcccagc aacaccaagg tggacaagaa agtggagccc    300
aagagctgcg acaagaccca cacctgcccc cctgcccag cccagagct gctgggcgga    360
ccctccgtgt tcctgttccc ccccaagccc aaggacaccc tgatgatcag caggaccccc    420
gaggtgacct gcgtggtggt ggccgtgagc cacgaggacc cagaggtgaa gttcaactgg    480
tacgtggacg gcgtggaggt gcacaacgcc aagaccaagc ccagagagga gcagtacaac    540
agcacctaca gggtggtgtc cgtgctgacc gtgctgcacc aggactggct gaacggcaag    600
gaatacaagt gcaaggtctc caacaaggcc ctgcagcccc catcgaaaa gaccatcagc    660
aaggccaaga gccagccacg ggagcccag gtgtacaccc tgcccccctc ccggaggag    720
atgaccaagg accaggtgtc cctgacctgt ctggtgaaag gcttctaccc cagcgacatc    780
gccgtggagt gggagagcaa cggccagccc gagaacaact acaagaccac ccccccagtg    840
ctggacagcg acggcagctt cttcctgtac agcaagctga ccgtggacaa gtccaggtgg    900
cagcagggca acgtgttcag ctgcagcgtg atgcacgagg ccctgcacaa ccactacacc    960
cagaagagcc tgagcctgtc ccccggcaag                                     990
```

SEQ ID NO: 87          moltype = AA  length = 9
FEATURE                Location/Qualifiers
source                 1..9
                       mol_type = protein
                       organism = synthetic construct
SEQUENCE: 87
AEAAAKALE                                                            9

SEQ ID NO: 88          moltype = AA  length = 5
FEATURE                Location/Qualifiers
source                 1..5
                       mol_type = protein
                       organism = synthetic construct
SEQUENCE: 88
DGSAK                                                                5

SEQ ID NO: 89          moltype = AA  length = 10
FEATURE                Location/Qualifiers
source                 1..10
                       mol_type = protein
                       organism = synthetic construct
SEQUENCE: 89
GSADGGSSAG                                                           10

SEQ ID NO: 90          moltype = AA  length = 14
FEATURE                Location/Qualifiers
source                 1..14
                       mol_type = protein
                       organism = synthetic construct
SEQUENCE: 90
GGGAKGGGGK GGGS                                                      14

```
SEQ ID NO: 91           moltype = AA  length = 25
FEATURE                 Location/Qualifiers
VARIANT                 1..25
                        note = This sequence may encompass 1-5 GGGGS repeating units
source                  1..25
                        mol_type = protein
                        organism = synthetic construct
SEQUENCE: 91
GGGGSGGGGS GGGGSGGGGS GGGGS                                              25

SEQ ID NO: 92           moltype = AA  length = 25
FEATURE                 Location/Qualifiers
VARIANT                 1..25
                        note = This sequence may encompass 1-5 SSSSG repeating units
source                  1..25
                        mol_type = protein
                        organism = synthetic construct
SEQUENCE: 92
SSSSGSSSSG SSSSGSSSSG SSSSG                                              25

SEQ ID NO: 93           moltype = AA  length = 25
FEATURE                 Location/Qualifiers
VARIANT                 1..25
                        note = This sequence may encompass 1-5 GSSGG repeating units
source                  1..25
                        mol_type = protein
                        organism = synthetic construct
SEQUENCE: 93
GSSGGGSSGG GSSGGGSSGG GSSGG                                              25

SEQ ID NO: 94           moltype = AA  length = 25
FEATURE                 Location/Qualifiers
VARIANT                 1..25
                        note = This sequence may encompass 1-5 GGSGG repeating units
source                  1..25
                        mol_type = protein
                        organism = synthetic construct
SEQUENCE: 94
GGSGGGGSGG GGSGGGGSGG GGSGG                                              25

SEQ ID NO: 95           moltype = AA  length = 6
FEATURE                 Location/Qualifiers
source                  1..6
                        mol_type = protein
                        organism = synthetic construct
SEQUENCE: 95
TVAAPS                                                                   6

SEQ ID NO: 96           moltype = AA  length = 7
FEATURE                 Location/Qualifiers
source                  1..7
                        mol_type = protein
                        organism = synthetic construct
SEQUENCE: 96
ASTSGPS                                                                  7

SEQ ID NO: 97           moltype = AA  length = 18
FEATURE                 Location/Qualifiers
source                  1..18
                        mol_type = protein
                        organism = synthetic construct
SEQUENCE: 97
KESGSVSSEQ LAQFRSLD                                                      18

SEQ ID NO: 98           moltype = AA  length = 14
FEATURE                 Location/Qualifiers
source                  1..14
                        mol_type = protein
                        organism = synthetic construct
SEQUENCE: 98
EGKSSGSGSE SKST                                                          14

SEQ ID NO: 99           moltype = AA  length = 6
FEATURE                 Location/Qualifiers
source                  1..6
                        mol_type = protein
                        organism = synthetic construct
SEQUENCE: 99
```

```
GGGGGG                                                                       6

SEQ ID NO: 100       moltype = AA  length = 8
FEATURE              Location/Qualifiers
source               1..8
                     mol_type = protein
                     organism = synthetic construct
SEQUENCE: 100
GGGGGGGG                                                                     8

SEQ ID NO: 101       moltype = AA  length = 12
FEATURE              Location/Qualifiers
source               1..12
                     mol_type = protein
                     organism = synthetic construct
SEQUENCE: 101
GSAGSAAGSG EF                                                               12
```

IMMUNE-STIMULATING IL-2 FUSION PROTEINS

The instant application contains a Sequence Listing which has been submitted electronically in XML file format and is hereby incorporated by reference in its entirety. Said XML copy, created on Jul. 27, 2022, is named P33550US1_SL.xml and is 113,646 bytes in size.

TECHNICAL FIELD

The present invention relates to immune-stimulating IL-2 fusion proteins comprising antibodies joined to human interleukin-2 (hIL-2). The invention more specifically relates to humanized monoclonal antibodies or fragments thereof joined to hIL-2 or variants thereof and displaying a unique capability of preferentially stimulating cytotoxic T cells and NK cells compared to Treg cells. Furthermore, the invention relates to in vitro and in vivo therapeutic applications of the IL-2 fusion proteins, in particular as an immunotherapy in the treatment of cancer.

BACKGROUND

Malignant melanoma is a frequent cancer type in men and women. Once melanoma becomes metastatic and spreads to distant sites, the 5-year survival rate is quite poor, calculated at about 15%. Currently available treatment strategies for metastatic melanoma barely improve this survival rate.

Interleukin-2 (IL-2) is a cytokine able to potently stimulate cytotoxic lymphocytes against metastatic tumors. However, IL-2 is also able to stimulate so-called $CD25^+CD4^+$ regulatory T cells (Treg cells) that are crucial for prevention of autoimmune disease. Importantly, immunosuppressive Treg cells can significantly dampen anti-tumor responses by cytotoxic lymphocytes, thus somewhat antagonizing the beneficial anti-tumor effects of IL-2. Moreover, at doses required to achieve a clinical anti-tumor response, IL-2 can exert toxic adverse effects.

Treg cells play a pivotal role in tumor-induced immune suppression and have been shown to be inversely related to the outcome of several human malignancies. IL-2 promotes immune responses by inducing $CD4^+T$ cell proliferation and differentiation into helper T cells, and increasing the number and activity of $CD8^+T$ cells and NK cells. However, IL-2 also simultaneously dampens immune responses by promoting the development and maintenance of immunosuppressive $CD25^+CD4^+$ and $CD25^+CD4^+Foxp^{3+}$ Tregs. Low concentrations of IL-2 induce signaling through the high-affinity IL-2 receptor (IL-2R) comprised of IL-2Rα(also called CD25), IL-2Rβ also called (CD122), and common γ chain (γc, also called CD132), preferentially expressed on Tregs. Higher concentrations of IL-2 are necessary to induce signaling through the intermediate-affinity IL-2R, composed of IL-2Rβ and γc, expressed on memory $CD8^+T$ cells and NK cells. Immunotherapy using IL-2 has been used since the early 1980's for the immunotherapy of metastatic melanoma and metastatic renal cell carcinoma, leading to the approval by the FDA for these indications in 1996 and 1992, respectively. While IL-2 given at high doses has shown objective response rates in about 17% and complete regression in about 6-9% of patients suffering from these deadly metastatic cancers, IL-2 given at these doses frequently led to toxic adverse effects, such as hypotension, pulmonary edema, liver cell damage, gastrointestinal toxicity, vascular leakage syndrome (VLS) and general edema. Moreover, as mentioned above, IL-2 is able to stimulate immunosuppressive Treg cells, which in turn are able to dampen the activity of anti-tumor $CD8^+T$ cells and NK cells.

Several variants of human IL-2 exist, and different strategies have been employed to find IL-2 based compounds with improved in vivo properties, such as described in Rosalia et al. Current Opinion in Chemical Biology 2014, 23:39-46.

The development of antibody-cytokine fusion proteins, also called immunocytokines, is described in Murer et al. N Biotechnol. 2019 Sep. 25; 52: 42-53, the contents of which are herein incorporated by reference in their entirety.

The combination of IL-2 with a particular anti-IL-2 monoclonal antibody (mAb) has been shown to improve IL-2 therapy in experimental murine models of cancer immunotherapy by (1) directing IL-2 preferentially to cytotoxic lymphocytes, but not Treg cells, and by (2) rendering IL-2 more potent but less toxic, as described in Arenas-Ramirez M, et al. Science Translational Medicine 8,367ra 166 (2016) and Krieg C, et al. Proceedings of the National Academy of Sciences USA (2010) 107:11906-11911. See also WO2016/005950 and WO2017/122130. The contents of all of which are incorporated in their entireties.

This approach has the advantage that unmutated, natural IL-2 is delivered via anti-IL-2 mAb to $CD8^+T$ cells and NK cells, which subsequently exert potent anti-tumour properties, while IL-2 complexed to this kind of anti-IL-2 mAb barely activates Treg cells. Moreover, IL-2 complexed to this kind of anti-IL-2 mAb is much less toxic than standard IL-2 immunotherapy in mice.

SUMMARY OF THE INVENTION

The present disclosure relates generally to IL-2 fusion proteins comprising antibodies joined to human IL-2 (hIL-2), methods for their preparation and use, including methods for treating disorders. The IL-2 fusion proteins disclosed herein comprise human monoclonal antibodies joined to hIL-2 or a variant thereof, preferably by means of a linker, thereby favouring the stimulation of cytotoxic T cells and NK cells compared to Treg cells, for use in in vitro and in vivo therapeutic applications. The IL-2 fusion proteins disclosed herein can be used (alone or in combination with other agents or therapeutic modalities) to treat, prevent and/or diagnose disorders, such as cancerous disorders (for example solid and soft-tissue tumors, and hematological tumors) and cell proliferative disorders (for example hyperplasia, neoplasia, metaplasia, and various autoimmune disorders). In particular, the IL-2 fusion proteins disclosed hereing can be used to treat, prevent and/or diagnose metastatic cancer, also called stage IV cancer. Thus, methods for treating cancer and cell proliferative disorders using the IL-2 fusion protein are disclosed herein.

According to a first aspect of the invention, an IL-2 fusion protein is provided comprising an anti-IL-2 isolated humanized antibody or an IL-2-binding fragment thereof comprising a light chain variable region (VL) comprising a LCDR1, a LCDR2 and a LCDR3 and a heavy chain variable region (VH) comprising a HCDR1, a HCDR2 and a HCDR3; wherein the LCDR1 comprises SEQ ID NO: 14 or SEQ ID NO: 30 wherein the LCDR2 comprises SEQ ID NO: 15 or SEQ ID NO: 31; wherein the LCDR3 comprises SEQ ID NO: 16 or SEQ ID NO: 32; wherein the HCDR1 comprises SEQ ID NO: 11 or SEQ ID NO: 27; wherein the HCDR2 comprises SEQ ID NO: 12 or SEQ ID NO: 28; and wherein the HCDR3 comprises SEQ ID NO: 13 or SEQ ID NO: 29; joined to a circularly permuted human interleukin 2 (hIL-2) polypeptide or variant thereof.

According to a second aspect of the invention, an IL-2 fusion protein is provided comprising an anti-IL2 isolated humanized antibody or an IL-2-binding fragment thereof comprising, an LCDR1 comprising SEQ ID NO: 14; an LCDR2 comprising SEQ ID NO: 15; an LCDR3 comprising SEQ ID NO: 16; an HCDR1 comprising SEQ ID NO: 11; an HCDR2 comprising SEQ ID NO: 12; and an HCDR3 comprising SEQ ID NO: 13; or an LCDR1 comprising SEQ ID NO: 30; an LCDR2 comprising SEQ ID NO: 31; an LCDR3 comprising SEQ ID NO: 32; an HCDR1 comprising SEQ ID NO: 27; an HCDR2 comprising SEQ ID NO: 28; and an HCDR3 comprising SEQ ID NO: 29; joined to a circularly permuted human interleukin 2 (hIL-2) polypeptide or variant thereof.

In an embodiment the IL-2 fusion protein comprises:
a) the hIL-2 polypeptide or variant thereof joined or fused to the LCDR1 of the light chain variable region to produce a single polypeptide chain; and/or
b) the hIL-2 polypeptide or variant thereof joined, fused or linked to the LCDR1 of the light chain variable region by one or two amino acid linker sequences.

In a further embodiment the IL-2 fusion protein comprises the hIL-2 polypeptide or variant thereof joined to the LCDR1 of the light chain variable region by one or two amino acid linker sequences, wherein the amino acid linker sequences comprise glycine (G) or glycine-serine (GxS) linkers of 1 to 50 amino acids.

In one embodiment, two amino acids from LCDR1 are removed when joined to the hIL-2 polypeptide or variants thereof such that the LCDR1 comprises SEQ ID NO: 22 or SEQ ID NO: 33.

In one embodiment the IL-2 fusion protein comprises the hIL-2 polypeptide or variant thereof joined to the LCDR1 by a first linker at residue Y8 of the LCDR1 and a second linker at residue D11 according to the Kabat definition.

In one embodiment the IL-2 fusion protein comprises the light chain variable (VL) and heavy chain variable (VH) regions of the antibody or fragment thereof used to prepare the fusion protein and within each LCDR1 the hIL-2 polypeptide or variant thereof is inserted having at least 80%, 85%, 90%, 95%, 96%, 97%, 98% of 99% identity to the amino acid sequences:
VL, SEQ ID NO: 9; VH, SEQ ID NO: 7, or
VL, SEQ ID NO: 26; VH, SEQ ID NO: 25.

In one embodiment the IL-2 fusion protein comprises the light chain variable (VL) and heavy chain variable (VH) regions of the antibody or fragment thereof joined to the hIL-2 polypeptide or variant thereof having at least 80%, 85%, 90%, 95% 96%, 97%, 98% or 99% identity to the amino acid sequences:
VL, SEQ ID NO: 56; SEQ ID NO: 57; SEQ ID NO: 58; SEQ ID NO: 59; SEQ ID NO: 60; SEQ ID NO: 61 or SEQ ID NO: 62; and VH, SEQ ID NO: 7, or
VL, SEQ ID NO: 63; SEQ ID NO: 64; SEQ ID NO: 65; SEQ ID NO: 66; SEQ ID NO: 67; and VH, SEQ ID NO: 25.

In one embodiment the IL-2 fusion protein comprises the hIL-2 polypeptide or variant thereof joined to the LCDR1 of the antibody or fragment thereof by a first linker at residue Y31 of the variable light chain (VL) and a second linker at residue D34 according to the Kabat definition.

In one embodiment the IL-2 fusion protein comprises the first and second linkers both selected from the group consisting of no linker, a G linker, a GG linker, a GGG linker, a linker according to SEQ ID NO: 48, a linker according to SEQ ID NO: 49, a linker according to SEQ ID NO: 50, a linker according to SEQ ID NO: 51, a linker according to SEQ ID NO: 52, a linker according to SEQ ID NO: 53, a linker according to SEQ ID NO: 54 and a linker according to SEQ ID NO: 55. Preferably, the first linker and second linkers are respectively, no linker and a G linker, a G linker and a GG linker, a GG linker and a GGG linker, a GGG linker and SEQ ID NO: 48, SEQ ID NO: 48 and SEQ ID NO: 49, SEQ ID NO: 49 and SEQ ID NO: 50, SEQ ID NO: 50 and SEQ ID NO: 51, SEQ ID NO: 51 and SEQ ID NO: 52, SEQ ID NO: 52 and SEQ ID NO: 53, SEQ ID NO: 53 and SEQ ID NO: 54, and SEQ ID NO: 54 and SEQ ID NO: 55.

In one embodiment the IL-2 fusion protein comprises a circularly permuted hIL-2 polypeptide according to SEQ ID NO: 3 or a circularly permuted variant of Proleukin® according to SEQ ID NO: 4.

In one embodiment the IL-2 fusion protein comprises residue Y31 joined to residue N1 of the circularly permuted hIL-2 polypeptide or variant thereof with a GGG linker, and wherein residue D34 is joined to residue K132 of the circularly permuted hIL-2 polypeptide or variant thereof according to SEQ ID NO: 4 with a GGGG linker according to SEQ ID NO: 48.

In one embodiment the IL-2 fusion protein comprises a heavy chain (VH-CH$_{1,2,3}$) and a light chain (VL-CL) comprising or consisting of the amino acid sequences:
VH-CH1,2,3, SEQ ID NO:5 and VL-CL, SEQ ID NO:56,
VH-CH1,2,3, SEQ ID NO:5 and VL-CL, SEQ ID NO:57,
VH-CH1,2,3, SEQ ID NO:5 and VL-CL, SEQ ID NO:58,
VH-CH1,2,3, SEQ ID NO:5 and VL-CL, SEQ ID NO:59,
VH-CH1,2,3, SEQ ID NO:5 and VL-CL, SEQ ID NO:60,
VH-CH1,2,3, SEQ ID NO:5 and VL-CL, SEQ ID NO:61,
VH-CH1,2,3, SEQ ID NO:5 and VL-CL, SEQ ID NO:62,
VH-CH1,2,3, SEQ ID NO:23 and VL-CL, SEQ ID NO:63,
VH-CH1,2,3, SEQ ID NO:23 and VL-CL, SEQ ID NO:64,
VH-CH1,2,3, SEQ ID NO:23 and VL-CL, SEQ ID NO:65,
VH-CH1,2,3, SEQ ID NO:23 and VL-CL, SEQ ID NO:66, or
VH-CH1,2,3, SEQ ID NO:23 and VL-CL, SEQ ID NO:67; or sequences having at least 80%, 85%, 90%, 95%, 96%, 97%, 98% or 99% identity thereto.

In one aspect the IL-2 fusion protein comprises:
a) an anti-IL-2 humanized antibody comprising a heavy chain (VH-CH$_{1,2,3}$) and a light chain (VL-CL) wherein the heavy chain comprises or consists of an amino acid sequence according to SEQ ID NO:5 and the light chain comprises or consists of an amino acid sequence according to SEQ ID NO:6; or wherein the heavy chain comprises or consists of an amino acid sequence according to SEQ ID NO:23 and the light chain comprises or consists of an amino acid sequence according to SEQ ID NO:24; joined to
b) a circularly permuted human interleukin (hIL-2) polypeptide or variant thereof.

In one embodiment the IL-2 fusion protein comprises an Fc portion (CH2,3) comprising a human IgG1 Fc.

According to a third aspect of the invention, a pharmaceutical composition comprising the IL-2 fusion protein according to the first or second aspect of the invention and a pharmaceutically acceptable carrier is provided.

According to a fourth aspect an isolated nucleic acid molecule encoding the IL-2 fusion protein according to the first or second aspect of the invention is provided.

According to a fifth aspect an expression vector comprising the isolated nucleic acid molecule according to the fourth aspect of the invention is provided.

According to a sixth aspect a host cell comprising the nucleic acid molecule according to the fourth aspect of the invention is provided.

According to a seventh aspect a method of treating a cell proliferative disorder or cancer by (1) selecting a patient having a cell proliferative disorder or cancer and (2) administering a therapeutically effective amount of the IL-2 fusion protein according to the first or second aspect of the invention is provided.

In one embodiment according to the seventh aspect of the invention, the therapeutically effective amount of the IL-2 fusion protein is administered in a dosage amount of about 0.01 to 1 mg/kg.

In a further embodiment according to the seventh aspect of the invention, multiple doses are administered to the patient, preferably once every week, every 2 weeks or every 3 weeks.

According to an eighth aspect of the invention a method of stimulating the immune system of an individual having cancer to prevent or destroy cancer cell growth, comprising administering to said individual an effective amount of a composition comprising the IL-2 fusion protein according to the first or second aspect of the invention and a pharmaceutically acceptable carrier is provided, whereby the immune system of the individual is stimulated, thereby preventing or destroying cancer cell growth.

According to a ninth aspect there is provided a composition comprising the IL-2 fusion protein according to the first or second aspects.

According to a tenth aspect of the invention an IL-2 fusion protein or a composition for use as a medicament, preferably for use in the treatment of a cell proliferative disorder or cancer is provided.

The IL-2 fusion proteins according to aspects of the invention are advantageous, e.g. because they possess one or more of the following properties. The antibody to be fused, joined or linked to hIL-2 demonstrates an affinity for h-IL-2. The IL-2 specifically joined to the antibody cannot efficiently bind human IL-2 receptor alpha (also known as CD25) anymore, effectively reducing the binding of human CD25 to the IL-2 fusion protein to background levels as compared to the binding of human CD25 to free (non-complexed) hIL-2 when measured by surface plasmon resonance. This effectively reduces the ability of IL-2 to simultaneously dampen immune responses by avoiding its promotion of the development and maintenance of immunosuppressive $CD25^+CD4^+$ and $CD25^+CD4^+Foxp3^+$ Tregs. Furthermore, the IL-2 fusion proteins may display no measurable cross-reactivity to murine IL-2, which is advantageous for preclinical studies which usually involve mouse models.

BRIEF DESCRIPTION OF THE DRAWINGS

FIG. 3 discloses a GGG linker and a GGGG linker (according to SEQ ID NO: 48), respectively, in order of appearance.

BRIEF DESCRIPTION OF THE TABLES

Figure 1:
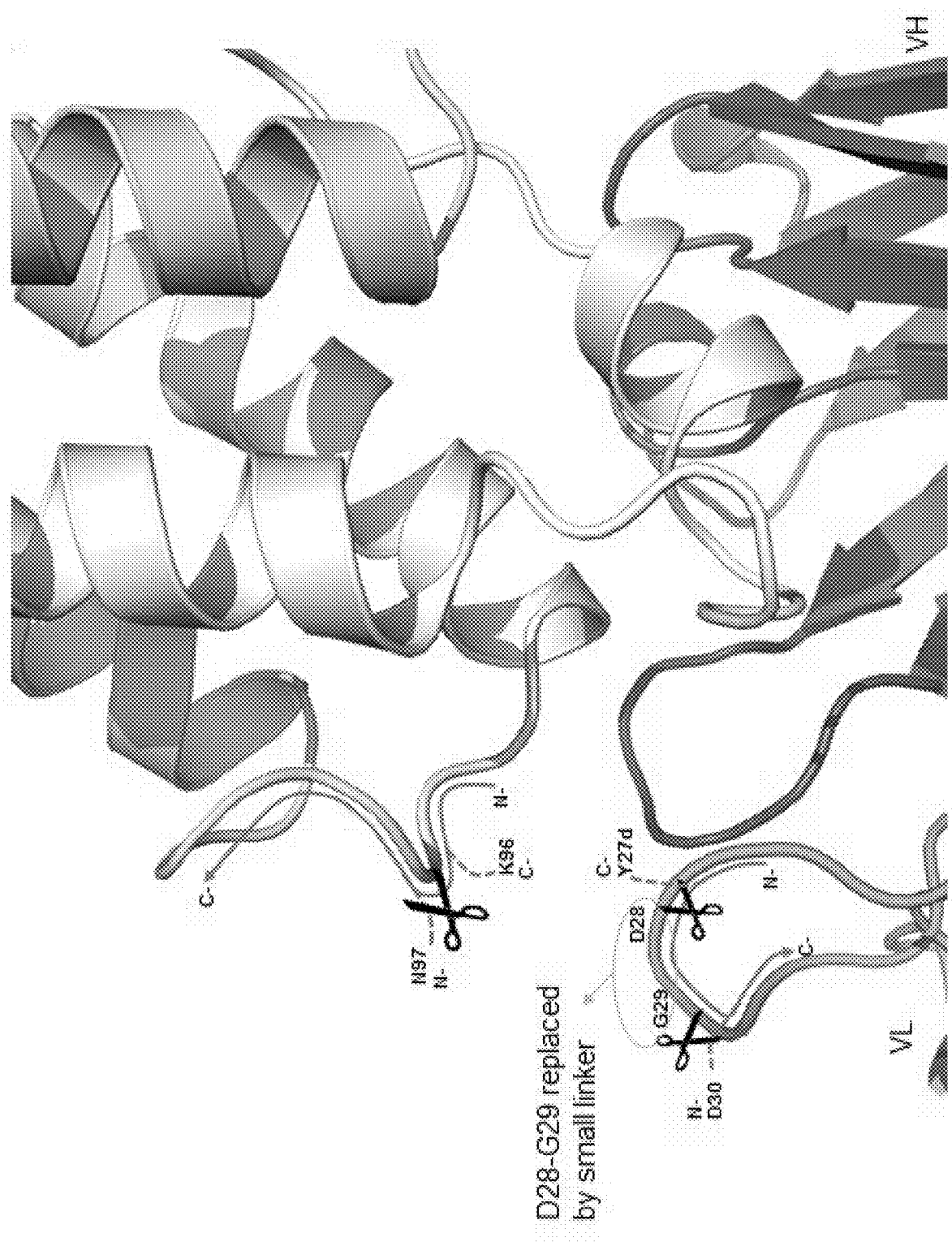
FIG. 1 is a schematic illustrating a fusion protein according to an embodiment.
Figure 2:
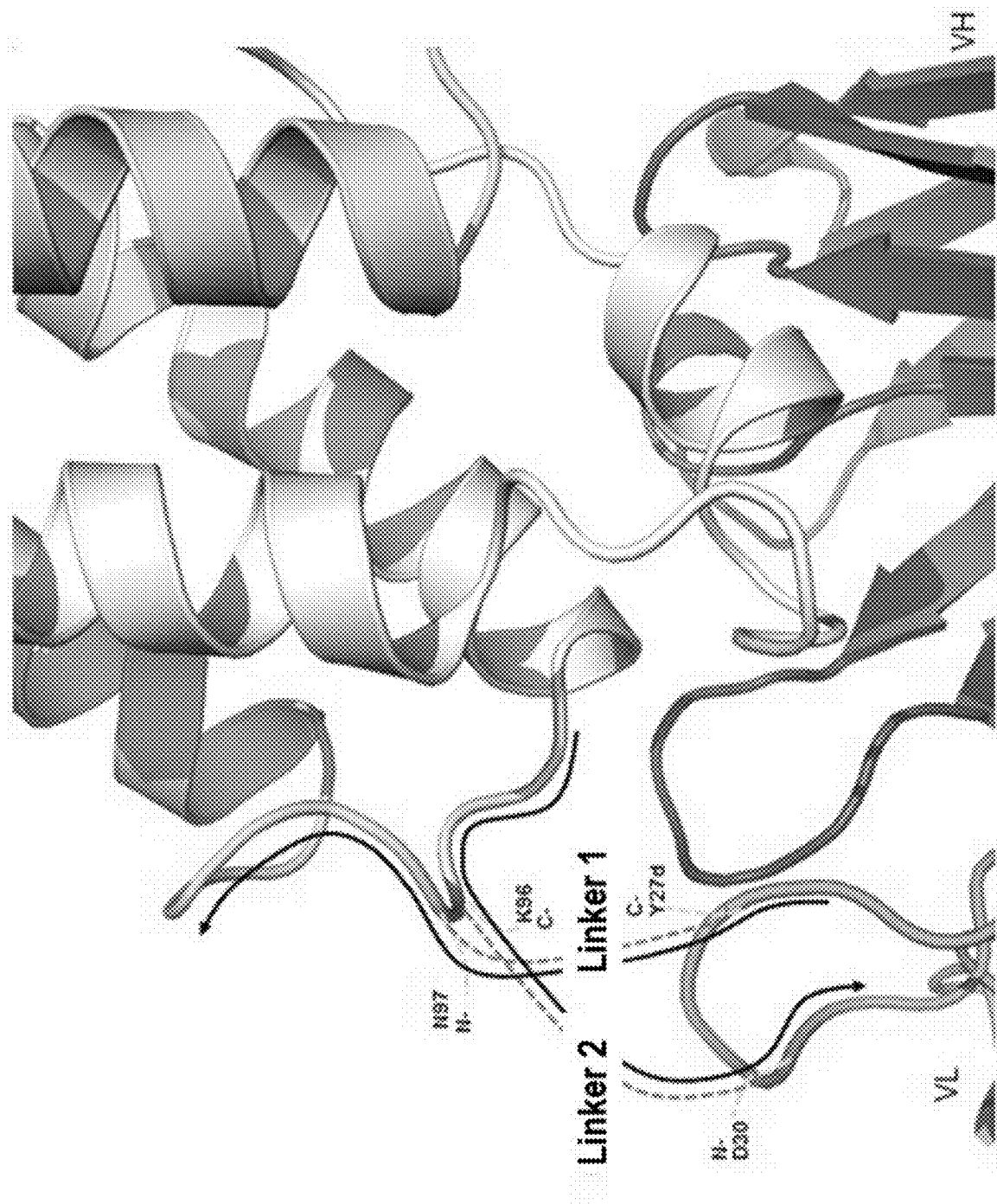
FIG. 2 is a schematic illustrating a fusion protein according to an embodiment.
Figure 3:
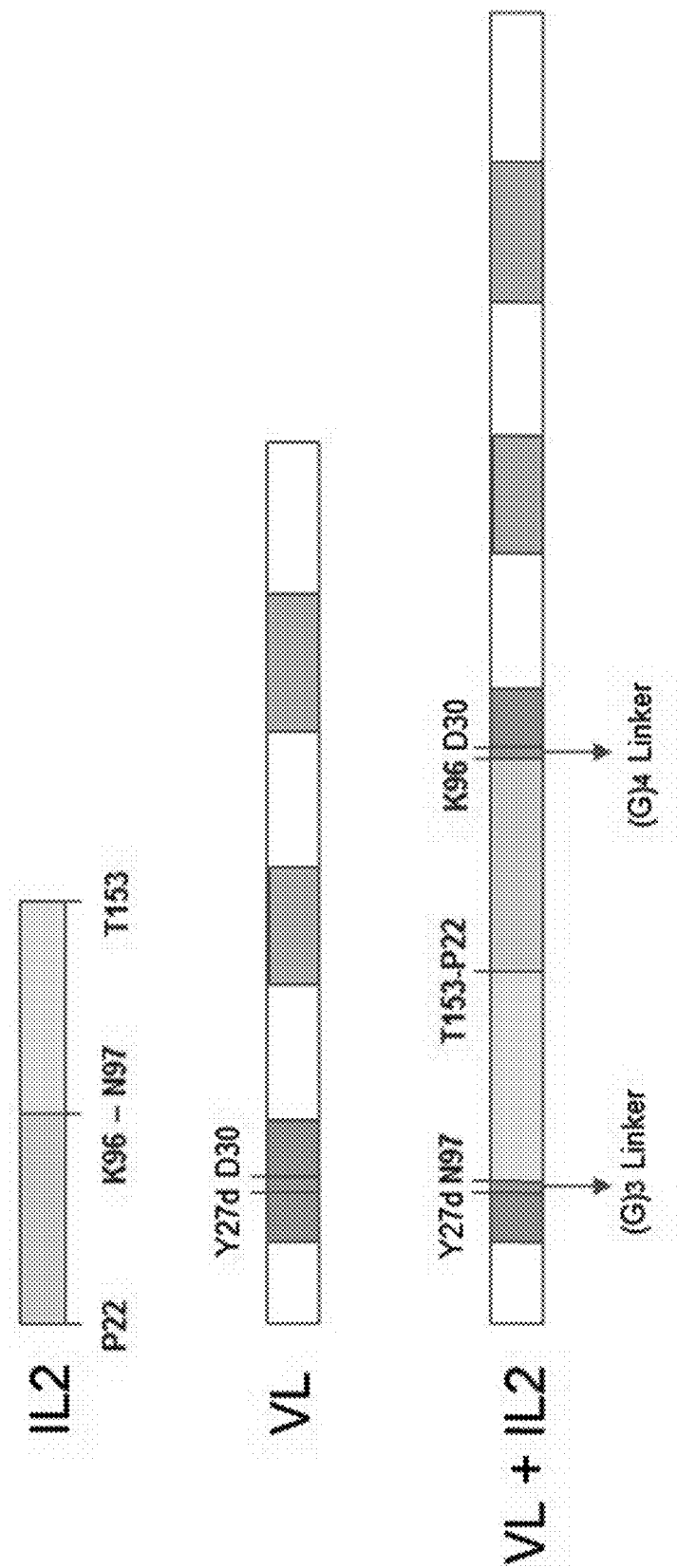
FIG. 3 illustrates alignment of a fusion protein according to an embodiment.
Figure 4:
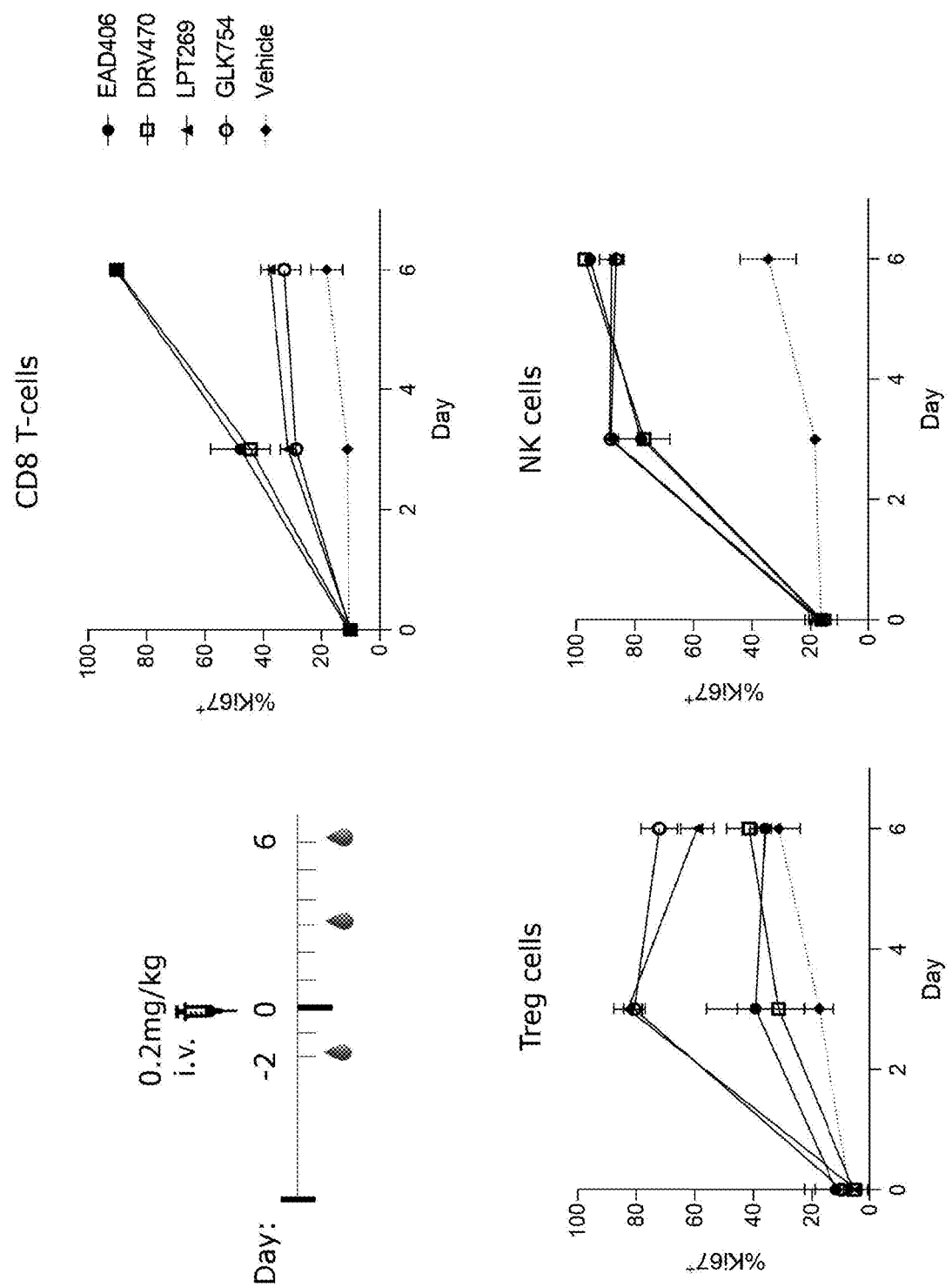
FIG. 4 indicates NK-cells, Treg cells and CD8 T-cells proliferation (%Ki67+) in blood of mice injected i.v. with compounds of the invention over time.

Table 1 is an overview of IL-2 variants according to embodiments of the invention.

Table 2 comprises light chain CDRs according to embodiments of the invention.

Table 3 comprises heavy chain CDRs according to embodiments of the invention.

Table 4 is an overview of IL-2 fusion proteins according to embodiments of the invention.

Table 5 provides binding affinities of Antibodies A, B and C according to some embodiments.

Table 6 provides an assessment of functionality of the IL-2 fusion proteins according to embodiments of the invention.

Table 7 provides EC50 values on IL-2 fusion proteins according to embodiments of the invention.

Table 8 provides information on the binding ability of the IL-2 fusion proteins according to embodiments of the invention.

Table 9 comprises EC50 data of IL-2 fusion proteins according to some embodiments.

Tables 10 comprises % of Ki67+ fold over at day 3 from blood according to embodiments of the invention.

Table 11 comprises % of Ki67+ fold over at day 6 from blood according to embodiments of the invention.

Table 12 comprises % of Ki67+ fold over at day 6 from splenocytes according to embodiments of the invention.

Table 13 provides tumor growth inhibition (TGI) in mice treated with IL-2 fusion protein compared to mice treated with vehicle.

Table 14 is a sequence listing comprising sequences useful for practicing the invention.

DETAILED DESCRIPTION

In order for the present disclosure to be more readily understood, certain terms are first defined below. Additional definitions for the following terms and other terms are set forth throughout the specification.

Unless specifically stated or obvious from context, as used herein, the term "or" is understood to be inclusive and covers both "or" and "and".

As used in the specification and claims, the singular form "a", "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely examples and that equivalents of such are known in the art.

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided. The term "consisting of" excludes any element, step, or ingredient not specified in the claim. In re Gray, 53 F.2d 520, 11 USPQ 255 (CCPA 1931); Ex parte Davis, 80 USPQ 448, 450 (Bd. App. 1948) ("consisting of" defined as "closing the claim to the inclusion of materials other than those recited except for impurities ordinarily associated therewith"). The term "consisting essentially of" limits the scope of a claim to the specified materials or steps "and those that do not materially affect the basic and novel characteristic(s)" of the claimed invention.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" may mean within one or more than one standard deviation per the practice in the art. "About" or "approximately" may mean a range of up to 10% (i.e., ±10%). Thus, "about" may be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg may include any amount between 4.5 mg and 5.5 mg. Furthermore, particularly with respect to biological systems or processes, the terms may mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", 5th ed., (2013), Academic Press; and "The Oxford Dictionary Of Biochemistry And Molecular Biology", Cammack et al. eds., 2nd ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the compounds and additional therapeutic agents of the disclosure include intravenous, intramuscular, subcutaneous, intraperitoneal, spinal or other parenteral routes of administration, for example by injection or infusion. Exemplary routes of administration for the compounds and additional therapeutic agents of the disclosure include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the compounds and additional therapeutic agents of the disclosure are administered via a non-parenteral route, e.g., orally. Other non-parenteral routes include a topical, epidermal or mucosal route of administration, for example, intranasally, vaginally, rectally, sublingually or topically. Administering may also be performed, for example, once, a plurality of times, and/or over one or more extended periods. In one embodiment, the IL-2 fusion proteins treatment is administered via an "infusion product" comprising the IL-2 fusion proteins.

Antibodies may include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain- antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments of any of the above. In some embodiments, antibodies described herein refer to polyclonal antibody populations.

An "antigen binding molecule," "antigen binding portion," or "antibody fragment" refers to any molecule that comprises the antigen binding parts (e.g., CDRs) of the antibody from which the molecule is derived. An antigen binding molecule may include the antigenic complementarity determining regions (CDRs). Examples of antibody fragments include, but are not limited to, Fab, Fab', F(ab), F(ab'), F(ab')2, and Fv fragments, dAb, linear antibodies, scFv antibodies, multispecific antibodies and/or nanobodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In some embodiments, the antigen binding molecule binds to CD19. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, may serve as an antigen. An antigen may be endogenously expressed, i.e. expressed by genomic DNA, or may be recombinantly expressed. An antigen may be specific to a certain tissue, such as a cancer cell, or it may be broadly expressed. In addition, fragments of larger molecules may act as antigens. In some embodiments, antigens are tumor antigens.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" may include a tumor. In this application, the term cancer is synonymous with malignancy.

An "anti-tumor effect" as used herein, refers to a biological effect that may present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect may also refer to the prevention of the occurrence of a tumor, e.g., a vaccine.

A "therapeutically effective amount," "effective dose," "effective amount," or "therapeutically effective dosage" of a therapeutic agent, e.g., engineered CAR T cells, small molecules, "agents" described in the specification, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. Such terms may be used interchangeably. The ability of a therapeutic agent to promote disease regression may be evaluated using a variety of methods known to the skilled practitioner, such as in human subjects during clinical trials, in animal model systems predictive of efficacy in humans, or by assaying the activity of the agent in in vitro assays. Therapeutically effective amounts and dosage regimens can be determined empirically by testing in known in vitro or in vivo (e.g. animal model) systems.

The term "combination" refers to either a fixed combination in one dosage unit form, or a combined administration where a compound of the present invention and a combination partner (e.g. another drug as explained below, also referred to as "therapeutic agent" or "agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time.

The present invention relates to IL-2 fusion proteins comprising antibodies joined, preferably by means of a linker, to human IL-2 or a variant thereof, that affect the in vivo function of this cytokine. A key advantage of fusion proteins is the ability to present IL-2 in a specific manner which can agonize receptors in selected immune cell populations such as CD8+T cells and NK cells while at the same time excluding other cell types (regulatory T cells). This can be achieved because the CDR domains can bind to the IL-2 portion of the fusion protein and sterically exclude binding to the IL-2R alpha. Another key advantage of fusion proteins according to the present invention is the ability to extend the half-life of the molecule due to their high molecular weight.

By "human interleukin-2" or "hIL-2" as used herein is meant human IL-2 (wildtype or wt) with UniProt ID number P60568, reproduced herein as SEQ ID NO: 1. IL-2 is also known as T cell growth factor (TCGF) and lymphokine. In various embodiments of the invention, variants, isoforms, and species homologs of human wildtype IL-2 are also included. Accordingly, antibodies of this disclosure may, in certain cases, cross-react with IL-2 from species other than human. In certain embodiments, the antibodies may be completely specific for one or more human IL-2 proteins and may not exhibit species or other types of non-human cross-reactivity.

Variants of hIL-2 include "IL-2 mutein", the term "mutein" means a polypeptide wherein specific substitutions to the interleukin-2 protein have been made. As used in reference to administrative modalities and treatments, the term "IL-2 mutein" means 1, 2, 3, 4, or 5 or more IL-2 muteins. For example, treatment using an IL-2 mutein may refer to treatment with a single IL-2 mutein, or a combination of multiple IL-2 muteins. Examples of variants of human IL-2 are the IL-2 muteins disclosed in WO2012/107417A1, having 3 mutations compared to wt hIL-2, and IL-2 mutein "Superkine".

Proleukin® (aldesleukin) is another example of a variant of human wt IL-2, well known to a person skilled in the art, and represented herein by SEQ ID NO: 2.

The term "circularly permuted" means a polypeptide wherein the sequence of amino acids has been cut and rejoined, so that the sequence is reordered and results in a protein structure with different connectivity, but overall similar three-dimensional shape. Circular permutation can occur due to posttranslational modifications or artificially engineered mutations. Examples of variants of hIL-2 include circular permutations of hIL-2, represented herein by SEQ ID NO: 3, in which the h-IL2 sequence has been cut at K96-N97, the sequence has been truncated by removal of M1 to S21 and rejoined at T153-P22. Circularly permuted Proleukin® is represented by SEQ ID NO: 4, in which the sequence of Proleukin® represented by SEQ ID NO: 2 is cut at K76-N77, the sequence is truncated by removal of the signal peptide M1 and A2, and rejoined at T134-P3. Further circular permutations are encompassed where 2, 3, 4, 5 or more sections of the hIL-2 are rejoined in alternate arrangements, for example, a CDAB arrangement of hIL-2 where section A comprises P22 to K63, section B comprises F64 to K96, section C comprises N97 to E126 and section D comprises Y127 to T153 as shown in SEQ ID NO: 3. Preferably, each domain comprises an alpha-helix and may comprise connecting amino acids. Circular permutation allows the IL-2 to retain its native three-dimensional structure while enabling direct fusion or joining to the variable chain, preferably with a short linker.

The term "antibody" is used in its meaning known in the art of cell biology and immunology; it refers to whole antibodies, any fragment or single chains thereof and related or derived constructs. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FRs). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes for example, monoclonal antibodies, human antibodies, humanized antibodies, camelid antibodies, or chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminus is a variable region and at the C-terminus is a constant region; the CH3 and CL domains actually comprise the carboxy-terminus of the heavy and light chain, respectively. In particular, the term "antibody" specifically includes an IgG-scFv format.

The "Complementarity Determining Regions" ("CDRs") are amino acid sequences with boundaries determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme) and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align.

Examples of antibody fragments include, but are not limited to, an scFv, a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR). The term single-chain variable fragment (scFv) refers to a fusion protein of the VH and VL chains of immunoglobulins, connected with a short linker peptide of ten to about 25 amino acids. The scFv retains the specificity of the original immunoglobulin, despite removal of the constant regions and the introduction of the linker. Such single chain antibodies are also intended to be encompassed within the terms "antibody" and "antibody fragment". These fragments are obtained using conventional techniques known to those of skill in the art, and the fragments are screened for utility in the same manner as are intact antibodies.

The phrase "monoclonal antibody" as used herein refers to polypeptides, including antibodies, that have substantially identical amino acid sequence or are derived from the same genetic source. This term also includes preparations of antibody molecules of single molecular composition. A monoclonal antibody composition displays a single binding specificity and affinity for a particular epitope.

The term "humanized antibody" is used in its meaning known in the art of cell biology and biochemistry; it refers to antibodies originally produced by immune cells of a non-human species, whose protein sequences have been modified to increase their similarity to antibody variants produced naturally in humans. For example, CDR sequences derived from the germline of another mammalian species, such as a mouse, have been grafted onto human framework sequences. Additional framework region modifications may be made within the human framework sequences as well as within the CDR sequences derived from the germline of another mammalian species.

The humanized antibodies of the invention may include amino acid residues not encoded by human sequences (e.g., mutations introduced by random or site-specific mutagenesis in vitro or by somatic mutation in vivo, or a conservative substitution to promote stability or manufacturing).

The phrase "recombinant humanized antibody" as used herein, includes all human antibodies that are prepared, expressed, created or isolated by recombinant means, such as antibodies isolated from a host cell transformed to express the humanized antibody, e.g., from a transfectoma, and antibodies prepared, expressed, created or isolated by any other means that involve splicing of all or a portion of a human immunoglobulin gene, sequences to other DNA sequences.

The term "Fc region" as used herein refers to a polypeptide comprising the CH3, CH2 and at least a portion of the hinge region of a constant domain of an antibody. Optionally, an Fc region may include a CH4 domain, present in some antibody classes. An Fc region, may comprise the entire hinge region of a constant domain of an antibody. In one embodiment, the invention comprises an Fc region and a CH1 region of an antibody. In one embodiment, the invention comprises an Fc region CH3 region of an antibody. In another embodiment, the invention comprises an Fc region, a CH1 region and a Ckappa/lambda region from the constant domain of an antibody. In one embodiment, a binding molecule of the invention comprises a constant region, e.g., a heavy chain constant region. In one embodiment, such a constant region is modified compared to a wild-type constant region. That is, the polypeptides of the invention disclosed herein may comprise alterations or modifications to one or more of the three heavy chain constant domains (CH1, CH2 or CH3) and/or to the light chain constant region domain (CL). Example modifications include additions, deletions or substitutions of one or more amino acids in one or more domains. Such changes may be included to optimize effector function, for example, to remove ability to bind to Fc gamma receptors on leukocytes to mediate undesired activation of white blood cells, optimize half-life, etc.

The term "fusion protein" refers to the fusion, joining or linking of two separate proteins, with or without an additional linker sequence. A fusion protein typically comprise a single polypeptide chain were two separate proteins/polypeptide sequences are linked in frame directly or via a peptide linker amino acid sequence.

The term "linker" or "linker sequence" is an amino acid sequence used to fuse, link or join two proteins. The linker sequence is preferably a glycine (G) or glycine-serine (GxS) linker, in particular comprising GGGGS (G4S) units. Additional linkers which may be used include alanine (A)—proline (P) linkers (AP)n , alanine-glutamine (E), lysine (K)-based linkers (e.g., A(EAAAK)n ALE) (SEQ ID NO: 87), asparagine (D)-G-S-A-K linkers (SEQ ID NO: 88) (e.g. GSADGGSSAG (SEQ ID NO: 89), GGGAKGGGGKGGGS (SEQ ID NO: 90) in various combinations to generate flexible or rigid peptide linkers.

The characteristics of linkers and their suitability for particular purposes are known in the art. See, e.g., Chen et al. Adv Drug Deliv Rev. Oct. 15; 65(10): 1357-1369 (2013) (disclosing various types of linkers, their properties, and associated linker designing tools and databases), which is incorporated herein by reference. In some embodiments, the linker is flexible, rigid, or in vivo cleavable. In some embodiments, the linker is flexible. Flexible linkers typically comprise small non-polar amino acids (e.g. Gly) or polar amino acids (e.g., Ser or Thr). Examples of flexible linkers that can be used in the present disclosure are sequences consisting primarily of stretches of Gly and Ser residues ("GS" linker). In some embodiments, flexible linkers comprise repeats of 4 Gly and Ser residues. In some embodiments, the flexible linker comprises 1-5 repeats of five Gly and Ser residues. Non-limiting examples of flexible linker include (Gly-Gly-Gly-Gly-Ser)n (SEQ ID NO: 91), (Ser-Ser-Ser-Ser-Gly)n (SEQ ID NO: 92) , Gly-Ser-Ser-Gly-Gly)n (SEQ ID NO: 93), and Gly-Gly-Ser-Gly-Gly)n (SEQ ID NO: 94), where n may be any integer between 1 and 5. In some embodiments, the linker is between 5 and 25 amino acid residues long. In some embodiments, the flexible linker comprises 5, 10, 15, 20, or 25 residues. Other suitable linkers may be selected from the group consisting of AS, AST, TVAAPS (SEQ ID NO: 95), TVA, ASTSGPS (SEQ ID NO: 96), KESGSVSSEQLAQFRSLD (SEQ ID NO: 97), EGKSSGSGSESKST (SEQ ID NO: 98), (Gly)6 (SEQ ID NO: 99), (Gly)8 (SEQ ID NO: 100), and GSAGSAAGSGEF (SEQ ID NO: 101). In general, a flexible linker provides good flexibility and solubility and may serve as a passive linker to keep a distance between functional domains. The length of the flexible linkers can be adjusted to allow for proper folding or to achieve optimal biological activity of the fusion proteins. In some embodiments, the linker comprises the sequence (Gly-Gly-Gly-Gly-Ser) (SEQ ID NO: 49). In some embodiments, the fusion protein comprises more than one linker. In some embodiments, the fusion protein has a first and a second linker, comprise different sequences. In some embodiments, the first and second linker comprise the same sequence. In some embodiments, the linker is G, GG, GGG, or is selected from SEQ ID NOs: 48 through 55, or is selected from SEQ ID Nos: 87 through 101. In some embodiments, the amino acid linkers comprise G or GxS linkers. In some embodiments, preferred G linkers are G, GG, GGG and GGGG according to SEQ ID NO: 48. Preferred GxS linkers are according to SEQ ID NO: 49, SEQ ID NO: 50, SEQ ID NO: 51, SEQ ID NO: 52, SEQ ID NO: 53, SEQ ID NO: 54 and SEQ ID NO: 55. The first linker and second linker are preferably not the same and can be selected from any combination of the linkers as set out above. More preferably, the first linker is of shorter length than the second linker.

The term "epitope" refers to any determinant capable of binding with high affinity to an immunoglobulin, specifically to the antigen binding portion of an antibody. An epitope as used herein is a region of an antigen that is bound by an antibody that specifically targets that antigen, and when the antigen is a protein, includes specific amino acids that directly contact the antibody. Most often, epitopes reside on proteins, but in some instances, may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics.

The term "affinity" refers to the characteristics of a binding interaction between a binding moiety (e.g., an antigen binding moiety (e.g., variable domain described herein) and/or Fc receptor binding moiety (e.g., FcRn binding moiety described herein)) and a target (e.g., an antigen (e.g., IL-2) and/or FcR (e.g., FcRn)) and that indicates the strength of the binding interaction. In some embodiments, the measure of affinity is expressed as a dissociation constant ($K_D$). In some embodiments, a binding moiety has a high affinity for a target (e.g., a $K_D$ of less than about $10^7$ M, less than about $10^8$ M, or less than about $10^9$ M). In some embodiments, a binding moiety has a low affinity for a target (e.g., a $K_D$ of higher than about $10^7$ M, higher than about $10^6$ M, higher than about $10^5$ M, or higher than about $10^4$ M). In some embodiments, a binding moiety has high affinity for a target at a first pH, has low affinity for the target at a second pH, and has an intermediate affinity for the target at a pH level between the first pH and the second pH.

As used herein, "$K_D$" refers to a dissociation constant, which is obtained from the ratio of $K_d$ to $K_a$ (i.e., $K_d/K_a$) and is expressed as a molar concentration (M). $K_D$ values can be determined using methods well established in the art, e.g., by using surface plasmon resonance, or using a biosensor system such as a Biacore® system.

As used herein, "$K_a$" refers to an association rate of a particular binding moiety and a target to form a binding moiety/target complex.

As used herein, "$K_d$" refers to a dissociation rate of a particular binding moiety/target complex.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids such as by, e.g., x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. Mol. Biol. 157:105-132; for hydropathy plots.

The terms "biomarker" or "marker" are used interchangeably herein. A biomarker is a nucleic acid or polypeptide and the presence or absence of a mutation or differential expression of the polypeptide is used to determine sensitivity to any treatment comprising an IL-2 fusion protein according to the invention. For example, a protein is a biomarker for a cancer cell when it is deficient, mutated, deleted, or decreased in post-translational modification, production, expression, level, stability and/or activity, as compared to the same protein in a normal (non-cancerous) cell or control cell.

The term "cell proliferative disorders" shall include dysregulation of normal physiological function characterized by abnormal cell growth and/or division or loss of function. Examples of "cell proliferative disorders" include, but are not limited to, hyperplasia, neoplasia, metaplasia, and various autoimmune disorders, e.g., those characterized by the dysregulation of T cell apoptosis.

"Combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the present invention and a combination partner, are both administered to a patient simultaneously in the form of a single entity or dosage. The term "non-fixed combination" means that the active ingredients, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

A "gene" refers to a polynucleotide containing at least one open reading frame (ORF) that is capable of encoding a particular polypeptide or protein after being transcribed and translated. A polynucleotide sequence can be used to identify larger fragments or full-length coding sequences of the gene with which they are associated. Methods of isolating larger fragment sequences are known to those of skill in the art.

"Gene expression" or alternatively a "gene product" refers to the nucleic acids or amino acids (e.g., peptide or polypeptide) generated when a gene is transcribed and translated.

As used herein, "expression" refers to the process by which DNA is transcribed into mRNA and/or the process by which the transcribed mRNA is subsequently translated into peptides, polypeptides or proteins. If the polynucleotide is derived from genomic DNA, expression may include splicing of the mRNA in a eukaryotic cell.

"Differentially expressed" as applied to a gene, refers to the differential production of the mRNA transcribed and/or translated from the gene or the protein product encoded by the gene. A differentially expressed gene may be overexpressed or under expressed as compared to the expression level of a normal or control cell. However, as used herein, overexpression is an increase in gene expression and generally is at least 1.25 fold or, alternatively, at least 1.5 fold or, alternatively, at least 2 fold, or alternatively, at least 3 fold or alternatively, at least 4 fold expression over that detected in a normal or control counterpart cell or tissue. As used herein, under expression, is a reduction of gene expression and generally is at least 1.25 fold, or alternatively, at least 1.5 fold, or alternatively, at least 2 fold or alternatively, at least 3 fold or alternatively, at least 4 fold expression under that detected in a normal or control counterpart cell or tissue. The term "differentially expressed" also refers to where expression in a cancer cell or cancerous tissue is detected but expression in a control cell or normal tissue (e.g. non-cancerous cell or tissue) is undetectable.

A high expression level of the gene can occur because of over expression of the gene or an increase in gene copy number. The gene can also be translated into increased protein levels because of deregulation or absence of a negative regulator. Lastly, high expression of the gene can occur due to increased stabilization or reduced degradation of the protein, resulting in accumulation of the protein.

As used herein, the term "inhibit", "inhibiting", or "inhibit the growth" or "inhibiting the proliferation" of a cancer cell refers to slowing, interrupting, arresting or stopping the growth of the cancer cell, and does not necessarily indicate a total elimination of the cancer cell growth. The terms "inhibit" and "inhibiting", or the like, denote quantitative differences between two states; refer to at least statistically significant differences between the two states. For example, "an amount effective to inhibit growth of cancer cells" means that the rate of growth of the cells will be at least statistically significantly different from the untreated cells. Such terms are applied herein to, for example, rates of cell proliferation.

The term "isolated" means separated from constituents, cellular and otherwise, in which the polynucleotide, peptide, polypeptide, protein, antibody or fragment(s) thereof, are normally associated with in nature. For example, an isolated polynucleotide is separated from the 3' and 5' contiguous nucleotides with which it is normally associated within its native or natural environment, e.g., on the chromosome. As is apparent to those of skill in the art, a non-naturally occurring polynucleotide, peptide, polypeptide, protein, antibody, or fragment(s) thereof, does not require "isolation" to distinguish it from its naturally occurring counterpart. In addition, a "concentrated," "separated" or "diluted" polynucleotide, peptide, polypeptide, protein, antibody or fragment(s) thereof, is distinguishable from its naturally occurring counterpart in that the concentration or number of molecules per volume is greater in a "concentrated" version or less than in a "separated" version than that of its naturally occurring counterpart.

The phrase "isolated antibody", as used herein, refers to antibody that is substantially free of other antibodies having different antigenic specificities or binding regions. Moreover, an isolated antibody may be substantially free of other cellular material and/or chemicals.

As used herein, the terms "neoplastic cells," "neoplastic disease," "neoplasia," "tumor," "tumor cells," "cancer," and "cancer cells," (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign. A "metastatic cell or tissue" means that the cell can invade and destroy neighboring body structures.

The terms "nucleic acid" and "polynucleotide" are used interchangeably and refer to a polymeric form of nucleotides of any length, either deoxyribonucleotides or ribonucleotides or analogs thereof. Polynucleotides can have any three-dimensional structure and can perform any function. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, siRNAs, shRNAs, RNAi agents, and primers. A polynucleotide can be modified or substituted at one or more base, sugar and/or phosphate, with any of various modifications or substitutions described herein or known in the art. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. The nucleotide sequence of the disclosure may be chemically modified or artificial. Nucleic acids include peptide nucleic acids (PNA), morpholinos and locked nucleic acids (LNA), as well as glycol nucleic acids (GNA) and threose nucleic acid (TNA). Each of these sequences is distinguished from naturally-occurring DNA or RNA by changes to the backbone of the molecule. Also, phosphorothioate (PS) linkage may be used. 2'-modified nucleotide (O-methyl, -O-methoxyethyl, and others) may be used. Other deoxynucleotide analogs include methylphosphonates, phosphoramidates, phosphorodithioates, N3'P5'-phosphoramidates and oligoribonucleotide phosphorothioates and their 2'-0-allyl analogs and 2'-0-methylribonucleotide methylphosphonates which may be used in a nucleotide of the disclosure.

In one embodiment, the nucleic acid is a modified RNA or based-modified RNA encoding one or more of the fusion proteins and/or antibodies/fragments the of the disclosure. Nucleic acids are usually synthesized using any of a variety of well-known enzymatic, recombinant DNA or chemical methods. In one embodiment, the nucleic acid comprises a codon optimized sequence encoding any one of the fusion proteins and antibodies/fragments thereof of the disclosure. The term "codon optimized" means that a codon that expresses a bias for human (i.e. is common in human genes but uncommon in other mammalian genes or non-mammalian genes) is changed to a synonymous codon (a codon that codes for the same amino acid) that does not express a bias for human. Thus, the change in codon does not result in any amino acid change in the encoded protein. In certain embodiments, a nucleic acid according to the present disclosure is codon optimized for expression in a non-human host cell. In other embodiments, the nucleic acid is codon optimized for the polypeptide's producer cells. Unless otherwise specified or required, any embodiment of this invention that is a polynucleotide encompasses both the double-stranded form and each of two complementary single-stranded forms known or predicted to make up the double-stranded form.

The term "polypeptide" is used interchangeably with the term "protein" and in its broadest sense refers to a compound of two or more subunit amino acids, amino acid analogs, or peptidomimetics. The subunits can be linked by peptide bonds. In another embodiment, the subunit may be linked by other bonds, e.g., ester, ether, etc.

A polynucleotide or polynucleotide region (or a polypeptide or polypeptide region) has a certain percentage (for example, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Current Protocols in Molecular Biology, Ausubel et al., eds., (1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cut-off=60; expect=10; Matrix=BLOSUM62; Descriptions=50 sequences; sort by=HIGH SCORE; Databases=non-redundant.

"Suppressing" or "suppression" of tumor growth indicates a reduction in tumor cell growth when contacted with an IL-2 fusion protein according to the invention compared to tumor growth without contact with an IL-2 fusion protein according to the invention compound. Tumor cell growth can be assessed by any means known in the art, including, but not limited to, measuring tumor size, determining whether tumor cells are proliferating using a 3H-thymidine incorporation assay, measuring glucose uptake by FDG-PET (fluorodeoxyglucose positron emission tomography) imaging, or counting tumor cells. "Suppressing" tumor cell growth means any or all of the following states: slowing, delaying and stopping tumor growth, as well as tumor shrinkage. A "subject," "individual" or "patient" is used interchangeably herein, which refers to a vertebrate, preferably a mammal, more preferably a human. Mammals include, but are not limited to, mice, simians, humans, farm animals, sport animals, and pets.

IL-2 variants

In certain embodiments of the invention, human IL-2 of wildtype (wt) is used. It has UniProt ID number P60568 and is reproduced as SEQ ID NO: 1. Another embodiment of human IL-2 is the IL-2 mutein disclosed in WO2012/107417A1, having 3 mutations compared to wt hIL-2. Aldesleukin (trade name Proleukin®) is another embodiment of a variant of human IL-2, well known to a person skilled in the art, and represented herein by SEQ ID NO: 2. One embodiment of circularly permuted hIL-2 is represented herein by SEQ ID NO: 3 and one embodiment of circularly permuted Proleukin® is represented herein by SEQ ID NO: 4. The method of circularly permuting the IL-2 could be applied to other IL-2 variants. Other embodiments of IL-2 variants are no-alpha mutein and IL-2 superkine, as shown in Table 1.

TABLE 1

Exemplary IL-2 variants

| | Variant/Mutein | substitution at position x relative to full length wt IL-2 | substitution at position x relative to mature wt IL-2 |
|---|---|---|---|
| 1 | Proleukin ® (Aldesleukin) | C145S | C126S |
| 2 | no-alpha mutein | R58A, F62A, Y65A, E82A | R38A, F42A, Y45A, E62A |
| 3 | WO2012/107417A1 | F62A, Y65A, L92G | F42A, Y45A, L72G |
| 4 | IL-2 superkine | L100F, R101D, L105V, I106V, I112F | L80F, R81D, L85V, I86V, I92F |
| 5 | Circularly permuted hIL-2 | Cut at K96-N97, truncation of M1-A21, rejoin T153-P22 | |
| 6 | Circularly permuted Proleukin ® | C145S; cut at K96-N97, truncation of M1-A21, rejoin T153-P22 | C126S, |
| 7 | Circularly permuted Proleukin variant | C145S; cut at K96-N97, truncation of M1-A21 and N97, rejoin T153-P22 | C126S, |

IL-2 Fusion Protein

In a first embodiment the present invention provides an IL-2 fusion protein comprising an isolated humanized antibody or fragment thereof joined to human IL-2 or a variant thereof, preferably by means of a linker. In a preferred embodiment, the IL-2 portion of the fusion protein is inserted into one of the CDRs of the antibody directly or through a linker. In a preferred embodiment, the IL-2 portion is inserted with the LCDR1 of the antibody. In some embodiments, the fusion protein has the sequence of the IL-2 fusion proteins described in Table 4.

In some embodiments, said antibody comprises a light chain variable region comprising one or more of LCDR1, a LCDR2 and a LCDR3 according to Table 2 and a heavy chain variable region comprising one or more of a HCDR1, a HCDR2 and a HCDR3 according to Table 3. In one embodiment, the antibody comprises all 3 light chain CDRs. In one embodiment, the antibody comprises all 3 heavy chain CDRs. In one embodiment, the antibody comprises all said 6 CDRs. In one embodiment, the present invention provides an IL-2 fusion protein as described in the Examples section. In one embodiment, the disclosure provides a compound which comprises only said antibodies, without the IL-2 portion.

In another embodiment the present invention provides variants of an antibody or fragment thereof, including antigen-binding fragments, joined to human IL-2.

In one embodiment, the present invention provides antibodies or fragments thereof that have an amino acid sequence of the non-CDR regions of the heavy and/or light chain variable region sequence which is at least 80% identical (having at least 80% amino acid sequence identity) to the amino acid sequence of the non-CDR regions of the heavy and/or light chain variable region sequence of the parent antibodies e.g. Antibody A or Antibody B, of either the heavy of the light chain. As well, antibodies or fragments thereof that have an amino acid sequence of the non-extended CDR regions of the heavy and/or light chain variable region sequence which is at least 80% identical to the amino acid sequence of the non-extended CDR regions of the heavy and/or light chain variable region sequence of the parent antibodies of either the heavy or the light chain are provided by the present invention. Preferably the amino acid sequence identity of the non-CDR regions or of the non-extended CDR regions of the heavy and/or light chain variable region sequence is at least 85%, more preferably at least 90%, and most preferably at least 95%, in particular 96%, more particular 97%, even more particular 98%, most particular 99%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%.

The present disclosure also provides an IL-2 fusion protein comprising an antibody or fragment thereof joined to human IL-2 which further comprises a heavy and/or light constant region, in particular a human heavy and/or a human light constant region. Human heavy constant regions may be selected from the group of human immunoglobulins consisting of IgG 1 (IGHG 1), IgG2 (IGHG2), IgG3 (IGHG3), IgG4 (IGHG4), IgA1 (IGHAI), IgA2 (IGHA2), IgM (IGHM), IgD (IGHD), or IgE (IGHE), whereas the human heavy constant region IgG, in particular IgG 1 (IGHG 1) is preferred. Human light constant region may be selected from the group of human immunoglobulins consisting of kappa or lambda constant regions, whereas human kappa constant region is preferred. In a preferred embodiment the antibody or fragment thereof that binds to human IL-2 comprises a human IgG 1 (IGHG 1) heavy constant domain and a human light kappa constant domain. In one embodiment, the present invention provides an IL-2 fusion protein as described in the Examples section which further comprises a heavy chain and/or light chain constant region. In one embodiment, the disclosure provides a compound which comprises only said antibodies, without the IL-2 portion.

In one embodiment, the disclosure provides variants of the IL-2 fusion proteins described herein, particularly those in the Examples, that include deletions, insertions, inversions, repeats, duplications, extensions, and substitutions (e.g., conservative substitutions and/or substitutions with nonstandard amino acids) selected according to general rules well known in the art so as have little effect on activity or improve activity. Positional libraries may be used in such methods. Variants may be selected from either chemical or DNA-encoded platforms.

In addition or alternative to modifications made within the framework regions or CDR regions, IL-2 fusion proteins of the invention may be engineered to include modifications within the Fc region, typically to alter one or more functional properties of the antibody, such as serum half-life, complement fixation, Fc receptor binding, and/or antigen-dependent cellular cytotoxicity.

Furthermore, an IL-2 fusion protein of the invention may be chemically modified (e.g., one or more chemical moieties can be attached to the antibody) or be modified to alter its glycosylation. In various embodiments, the IL-2 fusion protein provided herein may be modified to improve deliverability, stability (e.g., cyclization, secondary structure formation, oxidation, hydrolysis, sequence deletions, lipidation) and/or potency, and to reduce degradation (e.g., cyclization, acetylation, amidation, D-amino acid replacement, hydrocarbon stapling).

The present invention provides for IL-2 fusion proteins which result in altered half-life in vivo. Many factors may affect a protein's half-life in vivo. For examples, kidney filtration, metabolism in the liver, degradation by proteolytic enzymes (proteases), and immunogenic responses (e.g., protein neutralization by antibodies and uptake by macrophages and dentritic cells). A variety of strategies can be used to extend the half-life of the IL-2 fusion proteins of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nanocarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, antibody fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10)alkoxy- or aryloxy-polyethylene glycol or polyethylene glycol-maleimide. In one embodiment, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies and antibody fragments thereof of the invention. See for example, EP 0 154 316 by Nishimura et al. and EP 0 401 384 by Ishikawa et al., each of which is incorporated by reference.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a normative amino acid any place an amber codon is positioned, converting the amber from a stop codon to one that signals incorporation of the chemically specified amino acid.

Recombinant pegylation technology (rPEG) can also be used for serum half-life extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum half-life of the protein is greatly increased. In contrast to traditional PEGylation, which requires chemical conjugation and repurification, the manufacturing process is greatly simplified and the product is homogeneous.

Polysialylation is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated by introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375, each of which is incorporated by reference. Further modifications to increase the biological half-life of antibodies includes the introduction of one or more of the following mutations:: T252L, T254S, T256F, as described in U.S. Pat. No. 6,277,375 to Ward, which is incorporated by reference. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al, which is incorporated by reference.

Further, antibodies can be conjugated to albumin in order to make the antibody or antibody fragment more stable in vivo or have a longer half-life in vivo. The techniques are well-known in the art, see, e.g., International Publication Nos. WO 93/15199, WO 93/15200, and WO 01/77137; and European Patent No. EP 413,622, each of which is incorporated by reference.

Nucleic acids, Vectors and Host Cells

In one embodiment, the present invention provides nucleic acids that encode any one or more of the IL-2 fusion proteins and their parts (e.g., the antibody part) of the disclosure. The invention also provides vectors comprising said nucleic acids, and cells comprising the same. In one embodiment, the nucleic acids comprise a sequence from those in Table 13. In one embodiment, the nucleic acids comprise a sequence selected from SEQ ID NOS. 74, 76, 78, 80, 82, 84, and 86. In one embodiment, the nucleic acids comprise a codon-optimized version of the nucleic acid sequences from table 13. In one embodiment, the nucleic acids comprise a codon-optimized version of a nucleic acid sequence selected from SEQ ID NOS. 74, 76, 78, 80, 82, 84, and 86.

In one embodiment, the present invention is directed to cell lines that express an IL-2 fusion protein or antibody of embodiments of the invention. Creation and isolation of cell lines producing an IL-2 fusion protein or antibody of the invention can be accomplished using standard techniques known in the art. The CHO cell line is preferred (available from public repositories such as ATCC, American Type Culture Collection, Manassas, Va.).

A wide variety of host expression systems can be used to express an IL-2 fusion protein or antibody of the present invention including prokaryotic and eukaryotic expression systems (such as yeast, baculovirus, plant, mammalian and other animal cells, transgenic animals, and hybridoma cells), as well as phage display expression systems. One example of a suitable bacterial expression vector is pUC119 and a suitable eukaryotic expression vector is a modified pcDNA3.1 vector with a weakened dhfr selection system. Other antibody/fusion protein expression systems are also known in the art.

An IL-2 fusion protein or antibody of the invention can be prepared by recombinant expression of immunoglobulin light and heavy chain genes in a host cell, as is well known to a person skilled in the art. To express an antibody or fusion protein recombinantly, a host cell is transformed, transduced, infected or the like with one or more recombinant expression vectors carrying DNA fragments encoding the immunoglobulin light and/or heavy chains of the antibody such that the light and/or heavy chains are expressed in the host cell. The heavy chain and light chain may be expressed in the same or different host cells. Preferably, the fusion proteins or recombinant antibodies are secreted into the medium in which the host cells are cultured, from which the products can be recovered or purified.

Standard recombinant DNA methodologies are used to obtain fusion protein or antibody heavy and light chain genes, incorporate these genes into recombinant expression vectors, and introduce the vectors into host cells. Such standard recombinant DNA technologies are described, for example, in Green and Sambrook (Eds.), Molecular Cloning; A Laboratory Manual, Fourth Edition, Cold Spring Harbor, N.Y., 2012.

In one embodiment, the invention provides a vector, preferably (but not limited to) a plasmid, a recombinant expression vector, a yeast expression vector, or a retroviral expression vector comprising a polynucleotide encoding an IL-2 fusion protein of the invention. The coding region(s) in the vector may be separated by a linker sequence of any size or content, preferably such linker, when present, is a polynucleotide encoding an internal ribosome entry site.

To express an IL-2 fusion protein or antibody of the invention, a DNA encoding a partial amino acid chain, as described in Table 13 are inserted into an expression vector such that the gene is operably linked to transcriptional and translational control sequences. The expression vector and expression control sequences are chosen to be compatible with the expression host cell used. Additionally, the recombinant expression vector can encode a signal peptide that facilitates secretion of the fusion protein or antibody light and/or heavy chain from a host cell. The fusion protein or antibody light and/or heavy chain gene can be cloned into the vector such that the signal peptide is operably linked in-frame to the amino terminus of the antibody chain gene. The signal peptide can be an immunoglobulin signal peptide or a heterologous signal peptide.

For expression of the light and/or heavy chains, the expression vector(s) encoding the heavy and/or light chains is introduced into a host cell by standard techniques e.g., electroporation, calcium phosphate precipitation, DEAE-dextran transfection, transduction, infection and the like. Although it is theoretically possible to express the fusion proteins or antibodies of the invention in either prokaryotic or eukaryotic host cells, eukaryotic cells are preferred and most preferably mammalian host cells, because such cells are more likely to assemble and secrete a properly folded and immunologically active fusion protein or antibody.

Preferred mammalian host cells for expressing the fusion proteins or recombinant antibodies of the invention include Chinese Hamster Ovary (CHO cells), e.g. as described in Urlaub and Chasin, Proc. Natl. Acad. Sci. USA 77:4216-20, 1980. When recombinant expression vectors encoding fusion protein or antibody genes are introduced into mammalian host cells, the fusion proteins or antibodies are produced by culturing the host cells for a period of time sufficient to allow for expression of the antibody in the host cells or, more preferably, secretion of the fusion protein or antibody into the culture medium in which the host cells are grown under appropriate conditions known in the art. Fusion proteins or antibodies can be recovered from the host cell and/or the culture medium using standard purification methods.

Pharmaceutical Compositions

In one embodiment, the invention provides pharmaceutical compositions comprising one or more of the fusion proteins and/or antibody and antibody fragments thereof of the disclosure and a pharmaceutical acceptable carrier. In one embodiment, the invention provides pharmaceutical compositions comprising one or more of the nuclei acids and/or vectors of the disclosure and a pharmaceutical acceptable carrier. In one embodiment, the invention provides pharmaceutical compositions comprising one or more of the cells of the disclosure and a pharmaceutical acceptable carrier. In one embodiment, these pharmaceutical compositions may comprise additional therapeutic agents.

Pharmaceutical compositions of the disclosure may be administered alone or may be administered in combination therapy, i.e., combined with other agents. For example, the combination therapy may include an IL-2 fusion protein according to the present disclosure combined with at least one other immune stimulatory or another cell therapy. Examples of therapeutic agents that can be used in combination therapy include CAR-T cells, T-cells, tumor infiltrating lymphocytes (TILs), NK cell therapies, checkpoint inhibitors (such as PD-1, TIM-3, LAG-3, CTLA-4 inhibitors or others), innate immunity stimulators (such as STING agonists or others), depleting antibodies (such as anti-HER2, anti-EGFR, anti-CD20, anti-CD38 or other anti-tumour antibodies).

In some embodiments, compositions comprising the proteins, nucleic acids, and/or cells disclosed herein may be administered in conjunction (before, after, and/or concurrently with said compositions) with other recombinant or engineered cytokines, such as IL-15, IL-7, IL-12 or IL-21.

In some embodiments, compositions comprising the proteins, nucleic acids, and/or cells disclosed herein may be administered in conjunction (before, after, and/or concurrently with said compositions) with strategies to block or deplete regulatory T cells (such as, but not limited to, anti-CD25 antibodies) or strategies to block or deplete monocyte derived suppressor cells (MDSC) or macrophages (such as, but not limited to, anti-CD47 antibodies).

In some embodiments, compositions comprising the proteins, nucleic acids, and/or cells disclosed herein may be administered in conjunction (before, after, and/or concurrently with said compositions) with radiotherapy.

In some embodiments, compositions comprising the proteins, nucleic acids, and/or cells disclosed herein may be administered in conjunction (before, after, and/or concurrently with said compositions) with anti-tumor vaccine strategies.

In some embodiments, compositions comprising the proteins, nucleic acids, and/or cells disclosed herein may be administered in conjunction (before, after, and/or concurrently with said compositions) with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylol melamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; Polysaccharide K (PSK); razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™(bexarotene), Panretin™, (alitretinoin); ONTAK™(denileukin diftitox); esperamicins; capecitabine; and pharmaceutically acceptable salts, acids or derivatives of any of the above. In some embodiments, compositions comprising CAR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone, R-CHOP (CHOP plus Rituximab), and G-CHOP (CHOP plus obinutuzumab).

In one embodiment, the additional therapeutic agents include PD-1 inhibitors such as nivolumab (OPDIVO®), pembrolizumab (KEYTRUDA®), Cemiplimab (Libtayo), pidilizumab (CureTech), and atezolizumab (Roche), and PD-L1 inhibitors such as atezolizumab, durvalumab, and avelumab.

In one embodiment, the additional therapeutic agents suitable for use in combination (before, after, and/or concurrently) with the proteins, nucleic acids, and/or cells of the and methods disclosed herein include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept,adipotide, denileukin diftitox, mTOR inhibitors such as Everolimus and Temsirolimus, hedgehog inhibitors such as sonidegib and vismodegib, CDK inhibitors such as CDK inhibitor (palbociclib), inhibitors of GM-CSF, CSF1, GM-CSFR, or CSF1R, in addition to anti-thymocyte globulin, lenzilumab and mavrilimumab.

In one embodiment, the GM-CSF inhibitor is selected from lenzilumab; namilumab (AMG203); GSK3196165/MOR103/otilimab (GSK/MorphoSys); KB002 and KB003 (KaloBios); MT203 (Micromet and Nycomed); MORAb-022/gimsilumab (Morphotek); or a biosimilar of any one of the same; E21R; and a small molecule. In one embodiment, the CSF1 inhibitor is selected from RG7155, PD-0360324, MCS110/lacnotuzumab), or a biosimilar version of any one of the same; and a small molecule. In one embodiment, the GM-CSFR inhibitor and the CSF1R inhibitor is/are selected from Mavrilimumab (formerly CAM-3001; MedImmune, Inc.); cabiralizumab (Five Prime Therapeutics); LY3022855 (IMC-CS4)(Eli Lilly), Emactuzumab, also known as RG7155 or RO5509554; FPA008 (Five Prime/BMS); AMG820 (Amgen); ARRY-382 (Array Biopharma); MCS110 (Novartis); PLX3397 (Plexxikon); ELB041/AFS98/TG3003 (ElsaLys Bio, Transgene), SNDX-6352 (Syndax); a biosimilar version of any one of the same; and a small molecule.

In some embodiments, the fusion proteins and antibodies of the disclosure are administered with an anti-inflammatory agent (before, after, and/or concurrently with T cell administration). Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), non-steroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In some embodiments, the fusion proteins and antibodies of the disclosure are administered before, together, or after the administration of another immunotherapy. In some embodiments, the immunotherapy comprises T-cells, CAR-T cells, tumor infiltrating lymphocytes and others). In some embodiments, the fusion proteins and antibodies of the disclosure are administered before, during, or after administration of a chimeric receptor therapy CAR-T (e.g., YES-CARTA™ axicabtagene ciloleucel (axi-cel), TECARTUS™-brexucabtagene autoleucel/KTE-X19, KYMRIAH™(tisagenlecleucel), brexucabtagene autoleucel/KTE-X19, KYMRIAH™(tisagenlecleucel), lisocabtagene maraleucel, Idecabtagene vicleucel/bb2121, TCR, TIL, immune check point inhibitors, among others. In one embodiment, the immunotherapy product comprises autologous or allogeneic CAR T cells. In one embodiment, the immunotherapy comprises T-Cell Receptor-modified T cells. In one embodiment, the immunotherapy comprises tumor infiltrating lymphocytes (TILs). In one embodiment, the immunotherapy product comprises Induced Pluripotent Stem Cells (iPSCs).

The term "combination" refers to either a fixed combination in one dosage unit form, or a combined administration where a compound of the present invention and a combination partner (e.g. another drug as explained below, also referred to as "therapeutic agent" or "agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). In one embodiment, the carrier should be suitable for subcutaneous route. Depending on the route of administration, the active compound, i.e., antibody, IL-2 fusion protein, immunoconjugate, or bispecific molecule, may be coated in a material to protect the compound from the action of acids and other natural conditions that may inactivate the compound.

The pharmaceutical compositions of the disclosure may include one or more pharmaceutically acceptable salts. A "pharmaceutically acceptable salt" refers to a salt that retains the desired biological activity of the parent compound and does not impart any undesired toxicological effects (see e.g., Berge, S.M., et al. 1977, J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine, histidine and the like.

A pharmaceutical composition of the disclosure also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), non-ionic surfactants (such as polysorbate) and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sucrose or other sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Reviews on the development of stable protein (e.g. antibody) formulations may be found in Cleland et al. 1993, Crit. Reviews. Ther. Drug Carrier Systems 10(4):307-377 and Wei Wang 1999, Int. J. Pharmaceutcs 185:129-88. Additional formulation discussions for antibodies may be found, e.g., in Daugherty and Mrsny 2006, Advanced Drug Delivery Reviews 58: 686-706; US Pat. Nos 6,171,586, 4,618,486, US Publication No. 20060286103, PCT Publication WO 06/044908, WO 07/095337, WO 04/016286, Colandene et al. 2007, J. Pharm. Sci 96: 1598-1608; Schulman 2001, Am. J. Respir. Crit. Care Med. 164:S6-S11 and other known references, each of which is incorporated by reference.

Solutions or suspensions used for intradermal or subcutaneous application typically include one or more of the following components: a sterile diluent such as water for injection, saline solution, fixed oils, polyethylene glycols, glycerine, propylene glycol or other synthetic solvents, antibacterial agents such as benzyl alcohol or methyl parabens, antioxidants such as ascorbic acid or sodium bisulfite, chelating agents such ethylenediaminetetraacetic acid, buffers such as acetates, citrates or phosphates, and agents for the adjustment of tonicity such as sodium chloride or dextrose. The pH can be adjusted with acids or bases, such as hydrochloric acid or sodium hydroxide. Such preparations may be enclosed in ampoules, disposables syringes or multiple dose vials made of glass or plastic.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the antibodies or proteins of the disclosure into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

In one specific embodiment, the IL-2 fusion proteins according to the disclosure were administered as a liquid formulation in a vial. The amount of drug per vial was 150 mg. The liquid contained 150 mg/mL fusion protein, 4.8 mM L-Histidine, 15.2 mM L-Histidine-HCl 220 mM Sucrose and 0.04% Polysorbate 20, at pH 6.0 ±0.5. A 20% overfill was added to permit complete removal of the intended dose.

In some embodiments, the administration of the fusion proteins and antibodies and additional therapeutic agents of the disclosure and compositions of the disclosure and the administration of the additional therapeutic agent are carried out on the same day, are carried out no more than 36 hours apart, no more than 24 hours apart, no more than 12 hours apart, no more than 6 hours apart, no more than 4 hours apart, no more than 2 hours apart, or no more than 1 hour apart or no more than 30 minutes apart. In some embodiments, the administration of the compounds and compositions of the disclosure and the administration of the additional therapeutic agent are carried out between at or about 0 and at or about 48 hours, between at or about 0 and at or about 36 hours, between at or about 0 and at or about 24 hours, between at or about 0 and at or about 12 hours, between at or about 0 and at or about 6 hours, between at or about 0 and at or about 2 hours, between at or about 0 and at or about 1 hours, between at or about 0 and at or about 30 minutes, between at or about 30 minutes and at or about 48 hours, between at or about 30 minutes and at or about 36 hours, between at or about 30 minutes and at or about 24 hours, between at or about 30 minutes and at or about 12 hours, between at or about 30 minutes and at or about 6 hours, between at or about 30 minutes and at or about 4 hours, between at or about 30 minutes and at or about 2 hours, between at or about 30 minutes and at or about 1 hour, between at or about 1 hours and at or about 48 hours, between at or about 1 hour and at or about 36 hours, between at or about 1 hour and at or about 24 hours, between at or about 1 hour and at or about 12 hours, between at or about 1 hour and at or about 6 hours, between at or about 1 hour and at or about 4 hours, between at or about 1 hour and at or about 2 hours, between at or about 2 hours and at or about 48 hours, between at or about 2 hours and at or about 36 hours, between at or about 2 hours and at or about 24 hours, between at or about 2 hours and at or about 12 hours, between at or about 2 hours and at or about 6 hours, between at or about 2 hours and at or about 4 hours, between at or about 4 hours and at or about 48 hours, between at or about 4 hours and at or about 36 hours, between at or about 4 hours and at or about 24 hours, between at or about 4 hours and at or about 12 hours, between at or about 4 hours and at or about 6 hours, between at or about 6 hours and at or about 48 hours, between at or about 6 hours and at or about 36 hours, between at or about 6 hours and at or about 24 hours, between at or about 6 hours and at or about 12 hours, between at or about 12 hours and at or about 48 hours, between at or about 12 hours and at or about 36 hours, between at or about 12 hours and at or about 24 hours, between at or about 24 hours and at or about 48 hours, between at or about 24 hours and at or about 36 hours or between at or about 36 hours and at or about 48 hours. In some embodiments, the compounds and compositions of the disclosure and the additional therapeutic agent are administered at the same time.

In some embodiments, the fusion proteins and antibodies and additional therapeutic agents of the disclosure are administered in a dosage amount of from or from about 0.01 mg to 500 mg, such as 0.01 mg to 100 mg, 0.01 mg to 50 mg, 0.01 mg to 5 mg, 0.01 mg to 1 mg, 0.01 mg to 0.5 mg, 0.01 mg to 0.1 mg, 0.02 mg to 5 mg, 0.02 mg to 1 mg, 0.02 mg to 0.5 mg or 0.02 mg to 0.1 mg.

In some embodiments, the fusion protein or therapeutic agent of the invention is administered in a dosage amount from 0.01 mg/kg to 500 mg/kg, 0.01 mg kg/to 100 mg/kg, 0.01 mg/kg to 50 mg/kg, 0.01 mg/kg to 5 mg/kg, 0.01 mg/kg to 1 mg/kg, 0.01 mg kg/to 0.5 mg/kg, 0.01 mg/kg to 0.2 mg/kg, 0.02 mg/kg to 1 mg/kg, 0.02 mg kg/to 0.5 mg/kg, or 0.02 mg/kg to 0.1 mg/kg each. In some aspects, the agent is administered in a dosage amount of at least 0.01 mg/kg, 0.02 mg/kg, 0.05 mg/kg, 0.1 mg/kg, 0.2 mg/kg, 0.3 mg/kg, 0.5 mg/kg, 1 mg/kg, 5 mg/kg or more.

In certain embodiments, the fusion proteins and antibodies and additional therapeutic agents of the disclosure are administered by injection (e.g., subcutaneously or intravenously) at a dose of about 0.01 to 5 mg/kg, e.g., about 0.01 to 1 mg/kg; about 0.01 to 0.5 mg/kg; about 0.02 to 0.5 mg/kg, about 0.02 to 1 mg/kg, about 0.02 to 2 mg/kg, about 0.1 to 0.5 mg/kg, or about 0.4 mg/kg. In some embodiments, the fusion protein is administered at a dose of about 0.01 mg/kg, about 0.1 mg/kg, about 0.2 mg/kg, about 0.5 mg/kg, about 1 mg/kg, about 2 mg/kg, or about 10 mg/kg. In some embodiments, the fusion protein is administered at a dose of about 0.01-3 mg/kg, or about 0.01-1 mg/kg, or about 0.2-0.5 mg/kg. In some embodiments, the fusion protein is administered at a dose of about 0.01-0.5, 0.02-0.5, 0.02-0.05, 0.05-1, 0.5-1, 1-2, 2-4, 2-5, 5-15, or 5-20 mg/kg. The dosing schedule can vary from e.g., once a week to once every 2, 3, or 4 weeks. In some embodiments, the fusion protein is administered at a dose from about 0.01 to 10 mg/kg every other week. In another embodiment, the fusion protein is administered at a dose of about 0.01 to 1 mg/kg or 0.02 to 0.5 mg/kg once every week, once every two weeks, once every three weeks, or once every four weeks.

In other embodiments, the fusion proteins and antibodies and additional therapeutic agents of the disclosure can be administered by injection (e.g., subcutaneously or intravenously). The dosing schedule can vary from e.g., once a week to once every 2, 3, 4, 5, or 6 weeks The fusion proteins and antibodies and additional therapeutic agents of the disclosure can be administered together or at least 1 days, e.g., about 1, 2, 3, 4, 5, 6, 7, 8, 9, 10, 11, 12, 13, 14, 20, 25, 30, 35, or 40 days after other immunotherapy administration (e.g., CAR-T cells, tumor infiltrating lymphocytes, T cells).

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed inventions.

Therapeutic and other uses

The IL-2 fusion proteins of the present invention have numerous in vitro and in vivo diagnostic and therapeutic utilities involving the diagnosis and treatment of disorders with IL-2-dependent pathophysiology. For example, these molecules can be administered to cells in culture, in vitro or ex vivo, or to human subjects, e.g., in vivo, to treat, prevent and to diagnose a variety of disorders with IL-2-dependent pathophysiology.

Accordingly, in one embodiment, the invention provides a method of inhibiting growth of tumor cells in a subject, comprising administering to the subject a therapeutically effective amount of an IL-2 fusion protein as disclosed herein. In one embodiment, the methods are suitable for the treatment of cancer in vivo.

In a further embodiment, the invention provides a method of stimulating the immune system of an individual having cancer to prevent, slow or destroy cancer cell growth, in particular by preferentially stimulating $CD8^+$ T cells and NK cells which eliminate tumor or cancer cells, thereby preventing or destroying cancer cell growth. Advantageously, the method also reduces activation of $CD25^+$ T regulatory cells (Treg) which suppress antitumor immune responses.

When IL-2 fusion proteins are administered in combination with one or more agents, the combination can be administered in either order or simultaneously. The fusion proteins and antibodies of the disclosure may be administered more than once to the same subject.

In another aspect, a method of treating a subject, e.g., reducing or ameliorating, a proliferative condition or disorder (e.g., a cancer), e.g., solid tumor, a soft tissue tumor, or a metastatic lesion, in a subject is provided.

The term cancer is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma.). In one embodiment, the cancer is an advanced or unresectable melanoma that does not respond to other therapies. In other embodiments, the cancer is a melanoma with a BRAF mutation (e.g., a BRAF V600 mutation). Metastatic lesions of the aforementioned cancers can also be treated or prevented using the methods and compositions of the invention.

Exemplary cancers whose growth can be inhibited using the IL-2 fusion proteins disclosed herein include cancers typically responsive to immunotherapy. Non-limiting examples of preferred cancers for treatment include melanoma (e.g., metastatic malignant melanoma), renal cancer (e.g., clear cell carcinoma), prostate cancer (e.g., hormone refractory prostate adenocarcinoma), leukemia's, lymphomas, breast cancer, colon cancer and lung cancer (e.g., non-small cell lung cancer). Additionally, refractory or recurrent malignancies can be treated using the IL-2 fusion proteins described herein.

Examples of other cancers that can be treated include bone cancer, pancreatic cancer, skin cancer, cancer of the head or neck, cutaneous or intraocular malignant melanoma, uterine cancer, ovarian cancer, rectal cancer, anal cancer, gastro-esophageal, stomach cancer, testicular cancer, uterine cancer, carcinoma of the fallopian tubes, carcinoma of the endometrium, carcinoma of the cervix, carcinoma of the vagina, carcinoma of the vulva, Hodgkin Disease, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In other embodiments, the cancer is a hematological malignancy or cancer including but is not limited to a leukemia or a lymphoma. For example, the IL-2 fusion protein therapy can be used to treat cancers and malignancies including, but not limited to, e.g., acute leukemia's including but not limited to, e.g., B-cell acute lymphoid leukemia ("BALL"), T-cell acute lymphoid leukemia ("TALL"), acute lymphoid leukemia (ALL); one or more chronic leukemia's including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia)

of myeloid blood cells, and the like. In some embodiments, the lymphoma (e.g., an anaplastic large-cell lymphoma or non-Hodgkin lymphoma) has, or is identified as having, an ALK translocation, e.g., an EML4-ALK fusion.

In one embodiment, the cancer is chosen from a lung cancer (e.g., a non-small cell lung cancer (NSCLC) (e.g., a NSCLC with squamous and/or non-squamous histology)), a melanoma (e.g., an advanced melanoma), a renal cancer (e.g., a renal cell carcinoma, e.g., clear cell renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastro-esophageal cancer, thyroid cancer, cervical cancer, a lymphoproliferative disease (e.g., a post-transplant lymphoproliferative disease) or a hematological cancer, T-cell lymphoma, a non-Hodgkin's lymphoma, or a leukemia (e.g., a myeloid leukemia).

In another embodiment, the cancer is chosen form a carcinoma (e.g., advanced or metastatic carcinoma), melanoma or a lung carcinoma, e.g., a non-small cell lung carcinoma.

In one embodiment, the cancer is a lung cancer, e.g., a non-small cell lung cancer (NSCLC). In certain embodiments, the lung cancer, e.g., the non-small cell lung cancer, has, or is identified as having, an ALK rearrangement or translocation, e.g., an ALK fusion, e.g., an EML4-ALK fusion.

In another embodiment, the cancer is an inflammatory myofibroblastic tumor (IMT). In certain embodiments, the inflammatory myofibroblastic tumor has, or is identified as having, an ALK rearrangement or translocation, e.g., an ALK fusion, e.g., an EML4-ALK fusion.

In other embodiments, the cancer is NSCLC wherein the NSCLC is characterized by one or more of: aberrant activation, amplification, or a mutation of epidermal growth factor receptor (EGFR). In certain embodiments the cancer is NSCLC wherein the NSCLC is characterized by harbouring an EGFR exon 20 insertion, an EGFR exon 19 deletion, EGFR L858R mutation, EGFR T790M, or any combination thereof. In some embodiments, the NSCLC is characterized by harboring L858R and T790M mutations of EGFR. In some embodiments, the NSCLC is characterized by harboring an EGFR exon 20 insertion and T790M mutations of EGFR. In some embodiments, the NSCLC is characterized by harboring an EGFR exon 19 deletion and T790M mutations of EGFR. In some embodiments, the NSCLC is characterized by harboring EGFR mutation selected from the group consisting of an exon 20 insertion, an exon 19 deletion, L858R mutation, T790M mutation, and any combination thereof.

In yet another embodiment, the cancer is a neuroblastoma. In certain embodiments, the neuroblastoma has, or is identified as having, an ALK rearrangement or translocation, e.g., an ALK fusion, e.g., an EML4-ALK fusion.

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC or clear cell renal cell carcinoma Methods and compositions disclosed herein are useful for treating metastatic lesions associated with the aforementioned cancers.

EXAMPLES

Antibodies of the invention include the Antibody A and Antibody B which were derived, isolated and structurally characterized according to methods well known to a person skilled in the art. Antibody A is a high-affinity anti-IL-2 antibody and Antibody B is a low-affinity anti-IL-2 antibody. Antibody C has no IL-2 affinity and has been included as a control. Affinity of the antibody to the permuted IL-2 is required in order to present IL-2 in the correct manner and also to efficiently provide steric hinderance and thereby exclude the IL-2R alpha from the signaling complex.

Antibody A is a high-affinity anti-IL-2 antibody characterized by its full length heavy chain amino acid sequence according to SEQ ID NO: 5 and its full length light chain amino acid sequence according to SEQ ID NO: 6. The corresponding variable regions, VH and VL amino acid sequences of Antibody A are SEQ ID NO: 7 (variable heavy) and SEQ ID NO: 9 (variable light). Variable light and heavy chains nucleotide coding sequences of Antibody A are SEQ ID NO: 8 (variable heavy coding sequence) and SEQ ID NO: 10 (variable light coding sequence).

The CDR regions of the antibodies are delineated using the Kabat system (Kabat, E. A., et al. 1991, Sequences of Proteins of Immunological Interest, Fifth Edition, U.S. Department of Health and Human Services, NIH Publication No. 91-3242, see also Zhao&Lu 2009, Molecular Immunology 47:694-700). For the ease of reading, when CDR regions are delineated according to Kabat definition, they are called hereafter HCDR1, HCDR2, HCDR3, LCDR1, LCDR2, LCDR3 respectively. The CDRs of Antibodies A, B, and C are described in Table 13. The CDR regions of Antibody A are: HCDR1 according to SEQ ID NO: 11 and SEQ ID NO: 17 (consensus sequence), HCDR2 according to SEQ ID NO: 12 and SEQ ID NO: 19 (consensus sequence), HCDR3 according to SEQ ID NO: 13 and SEQ ID NO: 19 (consensus sequence), LCDR1 according to SEQ ID NO: 14 and SEQ ID NO: 20 (consensus sequence), LCDR2 according to SEQ ID NO: 15 and SEQ ID NO: 21 (consensus sequence), LCDR3 according to SEQ ID NO: 16. In the fusion protein LCDR1 is according to SEQ ID NO: 22 (X indicates amino acids removed when joined to the hIL-2 polypeptide or variants thereof). The actual CDRs (i.e., not the consensus) are described in Tables 2, 3, and 13.

Antibody B is a low-affinity anti-IL-2 antibody characterized by its full length heavy chain amino acid sequence according to SEQ ID NO: 23 and its full length light chain amino acid sequence according to SEQ ID NO: 24. The corresponding variable regions, VH and VL amino acid sequences of Antibody B are SEQ ID NO: 25 (variable heavy) and SEQ ID NO: 26 (variable light).

The CDR regions of Antibody B are: HCDR1 according to SEQ ID NO: 27 and SEQ ID NO: 17 (consensus sequence), HCDR2 according to SEQ ID NO: 28 and SEQ ID NO: 18 (consensus sequence), HCDR3 according to SEQ ID NO: 29 and SEQ ID NO: 19 (consensus sequence) , LCDR1 according to SEQ ID NO: 30 and SEQ ID NO: 20 (consensus sequence), LCDR2 according to SEQ ID NO: 31 and SEQ ID NO: 21 (consensus sequence), LCDR3 according to SEQ ID NO: 32 and SEQ ID NO: 16. In the fusion protein LCDR1 is according to SEQ ID NO: 33 (X indicates amino acids removed). The actual CDRs (i.e., not the consensus) are described in Tables 2, 3, and 13.

Antibody C has no IL-2 affinity and was characterized by its full length heavy chain amino acid sequence according to SEQ ID NO: 34 and its full length light chain amino acid sequence according to SEQ ID NO: 35. The corresponding variable regions, VH and VL amino acid sequences of Antibody C are SEQ ID NO: 36 (variable heavy) and SEQ ID NO: 37 (variable light).

The CDR regions of Antibody C are: HCDR1 according to SEQ ID NO: 38, HCDR2 according to SEQ ID NO: 39, HCDR3 according to SEQ ID NO: 40, LCDR1 according to SEQ ID NO: 41, LCDR2 according to SEQ ID NO: 42, and LCDR3 according to SEQ ID NO: 43. In the fusion protein LCDR1 is according to SEQ ID NO: 44 (X indicates amino acids removed).

IL-2 fusion protein were designed according to some embodiments of the present invention comprising Antibodies A, B or C joined to IL-2 either directly or by means of linkers of amino acids as set out in Table 4. The CDRs of those antibodies are described in Table 2. The different IL-2 fusion proteins described in Table 4 are the result of the use of different linkers utilized to join the IL-2 protein to the LCDR1 of Antibodies A, B or C. The light chain (kappa) CDRs that were used to make each of the fusion proteins according to the Kabat definition are found in Table 2.

TABLE 2

Light chain CDRs

| IL-2 Fusion Protein | LCDR1 | LCDR2 | LCDR3 |
|---|---|---|---|
| EAD406 | SEQ ID NO: 14 | SEQ ID NO: 15 | SEQ ID NO: 16 |
| XFO227 | SEQ ID NO: 14 | SEQ ID NO: 15 | SEQ ID NO: 16 |
| QTY065 | SEQ ID NO: 14 | SEQ ID NO: 15 | SEQ ID NO: 16 |
| FJC828 | SEQ ID NO: 14 | SEQ ID NO: 15 | SEQ ID NO: 16 |
| PGO345 | SEQ ID NO: 14 | SEQ ID NO: 15 | SEQ ID NO: 16 |
| DRV470 | SEQ ID NO: 14 | SEQ ID NO: 15 | SEQ ID NO: 16 |
| XUB802 | SEQ ID NO: 14 | SEQ ID NO: 15 | SEQ ID NO: 16 |
| EPK959 | SEQ ID NO: 30 | SEQ ID NO: 31 | SEQ ID NO: 32 |
| GYG794 | SEQ ID NO: 30 | SEQ ID NO: 31 | SEQ ID NO: 32 |
| DRO069 | SEQ ID NO: 30 | SEQ ID NO: 31 | SEQ ID NO: 32 |
| ECV200 | SEQ ID NO: 30 | SEQ ID NO: 31 | SEQ ID NO: 32 |
| BFC885 | SEQ ID NO: 30 | SEQ ID NO: 31 | SEQ ID NO: 32 |
| Consensus | SEQ ID NO: 20 | SEQ ID NO: 21 | SEQ ID NO: 22 |

The resulting heavy chain CDRs according to the Kabat definition are found in Table 3.

TABLE 3

Heavy chain CDRs

| IL-2 Fusion Protein | HCDR1 | HCDR2 | HCDR3 |
|---|---|---|---|
| EAD406 | SEQ ID NO: 11 | SEQ ID NO: 12 | SEQ ID NO: 13 |
| XFO227 | SEQ ID NO: 11 | SEQ ID NO: 12 | SEQ ID NO: 13 |
| QTY065 | SEQ ID NO: 11 | SEQ ID NO: 12 | SEQ ID NO: 13 |
| FJC828 | SEQ ID NO: 11 | SEQ ID NO: 12 | SEQ ID NO: 13 |
| PGO345 | SEQ ID NO: 11 | SEQ ID NO: 12 | SEQ ID NO: 13 |
| DRV470 | SEQ ID NO: 11 | SEQ ID NO: 12 | SEQ ID NO: 13 |
| XUB802 | SEQ ID NO: 11 | SEQ ID NO: 12 | SEQ ID NO: 13 |
| EPK959 | SEQ ID NO: 27 | SEQ ID NO: 28 | SEQ ID NO: 29 |
| GYG794 | SEQ ID NO: 27 | SEQ ID NO: 28 | SEQ ID NO: 29 |
| DRO069 | SEQ ID NO: 27 | SEQ ID NO: 28 | SEQ ID NO: 29 |
| ECV200 | SEQ ID NO: 27 | SEQ ID NO: 28 | SEQ ID NO: 29 |
| BFC885 | SEQ ID NO: 27 | SEQ ID NO: 28 | SEQ ID NO: 29 |
| Consensus | SEQ ID NO: 17 | SEQ ID NO: 18 | SEQ ID NO: 19 |

Based on these optimized variable heavy and light regions, twelve optimized antibodies were generated using a human IgG1 Fc domain either with a wild type Fc or one carrying the N297A (EU numbering system) point mutation, and variable light and heavy regions according to Tables 2 and 3.

Any Fc domain may be used to generate further antibodies, as known to a person skilled in the art. Particularly contemplated Fc domains are non Fc modified human IgG1 according to SEQ ID NO: 73, human IgG2 according to SEQ ID NO: 75, human IgG3 according to SEQ ID NO: 77, human IgG4 according to SEQ ID NO: 79, human IgG1 Fc modified with LALA mutation according to SEQ ID NO: 81, human IgG1 Fc modified with N297A mutation according to SEQ ID NO: 83, human IgG1 Fc modified with DAPA mutation according to SEQ ID NO: 85.

According to a preferred embodiment, the Fc domain is a human IgG1 according to SEQ ID NO: 73, and according to an even more preferred embodiment, the Fc domain is a human IgG1 Fc modified with N297A mutation according to SEQ ID NO: 83.

IL-2 fusion proteins are provided according to some embodiments of the present invention comprising Antibodies A, B or C joined to IL-2 either directly or by means of linkers of amino acids as set out in Table 4:

TABLE 4

IL-2 Fusion Proteins

| IL-2 Fusion Protein | Parent Antibody | IL-2 | Linker 1 (amino acids) | Linker 2 (amino acids) | Light Chain (VL-linker 1-IL2-linker 2-VL) |
|---|---|---|---|---|---|
| EAD406 | A | SEQ ID NO: 4 | 0 | 1 G linker | SEQ ID NO: 56 |
| XFO227 | A | SEQ ID NO: 4 | 2 GG linker | 3 GGG linker | SEQ ID NO: 57 |
| QTY065 | A | SEQ ID NO: 4 | 3 GGG linker | 4 SEQ ID NO: 48 | SEQ ID NO: 58 |
| FJC828 | A | SEQ ID NO: 4 | 4 SEQ ID NO: 48 | 5 SEQ ID NO: 49 | SEQ ID NO: 59 |
| PGO345 | A | SEQ ID NO: 4 | 6 SEQ ID NO: 50 | 7 SEQ ID NO: 51 | SEQ ID NO: 60 |
| DRV470 | A | SEQ ID NO: 4 | 13 SEQ ID NO: 52 | 14 SEQ ID NO: 53 | SEQ ID NO: 61 |
| XUB802 | A | SEQ ID NO: 4 | 19 SEQ ID NO: 54 | 20 SEQ ID NO: 55 | SEQ ID NO: 62 |

TABLE 4-continued

IL-2 Fusion Proteins

| IL-2 Fusion Protein | Parent Antibody | IL-2 | Linker 1 (amino acids) | Linker 2 (amino acids) | Light Chain (VL-linker 1-IL2-linker 2-VL) |
|---|---|---|---|---|---|
| EPK959 | B | SEQ ID NO: 4 | 0 | 1<br>G linker | SEQ ID NO: 63 |
| GYG794 | B | SEQ ID NO: 4 | 2<br>GG linker | 3<br>GGG linker | SEQ ID NO: 64 |
| DRO069 | B | SEQ ID NO: 4 | 3<br>GGG linker | 4<br>SEQ ID NO: 48 | SEQ ID NO: 65 |
| ECV200 | B | SEQ ID NO: 4 | 6<br>SEQ ID NO: 50 | 7<br>SEQ ID NO: 51 | SEQ ID NO: 66 |
| BFC885 | B | SEQ ID NO: 4 | 13<br>SEQ ID NO: 52 | 14<br>SEQ ID NO: 53 | SEQ ID NO: 67 |
| LPT269 | C | SEQ ID NO: 4 | 0 | 1<br>G linker | SEQ ID NO: 68 |
| DXM339 | C | SEQ ID NO: 4 | 2<br>GG linker | 3<br>GGG linker | SEQ ID NO: 69 |
| FUE443 | C | SEQ ID NO: 4 | 3<br>GGG linker | 4<br>SEQ ID NO: 48 | SEQ ID NO: 70 |
| LQM346 | C | SEQ ID NO: 4 | 6<br>SEQ ID NO: 50 | 7<br>SEQ ID NO: 51 | SEQ ID NO: 71 |
| GLK754 | C | SEQ ID NO: 4 | 13<br>SEQ ID NO: 52 | 14<br>SEQ ID NO: 53 | SEQ ID NO: 72 |

The IL-2 fusion proteins according to the present invention comprise an antibody or antibody fragment thereof joined to hIL-2, preferably the circularly permuted Proleukin® variant of hIL-2 according to SEQ ID NO: 4. The amino acid linkers comprise G or GxS linkers. Preferred G linkers are G, GG, GGG or according to SEQ ID NO: 48. Preferred GxS linkers are according to SEQ ID NO: 49, SEQ ID NO: 50, SEQ ID NO: 51, SEQ ID NO: 52, SEQ ID NO: 53, SEQ ID NO: 54 and SEQ ID NO: 55.

Example 1. Anti-IL2 antibodies and control antibody production and characterization Expression and characterization of antibodies A, B and C The genes encoding for VL-CL (light chain) and VH-CH1-CH2-CH3 (heavy chain) were cloned into the mammalian expression vector pcDNA3.4 into separate plasmids. Signal peptide of human kappa light chain was fused at the N-terminal of the antibody or protein for secretory expression. The antibodies were produced using transient gene expression in Expi293 cells (Gibco, A14527) following standard protocols provided by the vendor. Plasmid DNA (HC/LC ratio 1:2 w/w) was transfected using Expi-Fectamine™ 293 Reagent. The cells were maintained at 37° C., 8% CO2 in an orbital shaker (150 rpm) for six days. The antibodies were purified to homogeneity from the supernatant by Protein A Chromatography (MabSelect™ SuRe™, GE17-5438-01).

Quality control of the proteins was performed by SDS-PAGE (NuPAGE™ 4-12% Bis-Tris Protein Gels, ThermoFisher) and analytic size exclusion chromatography (SEC) (GE lifesciences, Superdex 200 increase 10/300).

Results

Antibodies A, B and C were expressed in Expi293 cells. Yields and purity are reported in Table 5.

All antibodies were obtained as pure protein product, eluting as single peak in SEC-HPLC analysis.

$EC_{50}$ binding to IL-2 by ELISA

Recombinant human IL-2 was coated on Maxisorp ELISA plates (Invitrogen, 44-2404-21) at 5 µg/ml, 4° C. over night. After 2 hours blocking, antibodies A, B and C were incubated in a serial dilution starting from 10 µg/ml in assay buffer. The antibodies were detected with anti-human IgG-Peroxidase (Sigma, A0170). After addition and blockade of the chemoluminescent substrate, absorption was read ($A_{450}$-$A_{570}$ at plate reader, Spectramax iD3). $EC_{50}$ values were obtained by plotting Absorbance vs. log(Concentration).

Results

The $EC_{50}$ values of antibodies A, B and C to IL-2 of the present invention are reported in Table 5. Only antibody A displayed binding to IL-2 in ELISA and could be detected on the Fc-portion by an anti-human IgG antibody coupled to HRP.

$K_D$ measurement by Octet

Antibody A, B or C were immobilized on amine reactive (2$^{nd}$ Generation) sensors (ForteBio, 18-5092). Association (600s) and dissociation (900s) of a dilution series of recombinant IL-2 (Acro Biosystems, IL2-H4113) were measured on the antibody-coated biosensors on an Octet-System (Octet RED, ForteBio). $K_D$ values were obtained by fitting the kinetics data with the ForteBio Data Analysis Software (8.2).

Results

Binding affinities to recombinant human IL-2 of Antibodies A, B and C of the present invention measured by Octet are reported in Table 5. Antibody C did not show binding to IL-2 up to concentrations >1000 nM.

TABLE 5

Binding affinities to recombinant hIL-2

| Antibodies | Yield (mg/ml) | Purity by SEC-HPLC (%) | $EC_{50}$ to IL-2 by ELISA (nM) | $K_D$ to IL-2 (nM) |
|---|---|---|---|---|
| A | 193.9 | 95.8% | 0.37 | 2.1 |
| B | 282.4 | 98.9% | — | 269.8 |
| C | 453.5 | 98.5% | — | — |

Example 2. IL-2 fusion proteins production and characterization

Expression and characterization of IL-2 fusion proteins

The genes encoding for VL-(IL-2)-CL and VH-CH1-CH2-CH3 were cloned into the mammalian expression vector pcDNA3.4 into separate plasmids. Signal peptide of human kappa light chain was fused at the N-terminal of the antibody or protein for secretory expression. The antibody IL-2 fusion proteins were produced using transient gene expression in Expi293 cells (Gibco, A14527) following standard protocols provided by the vendor. Plasmid DNA (HC/LC ratio 1:2 w/w) was transfected using Expi-Fectamine™ 293 Reagent. The cells were maintained at 37° C., 8% CO2 in an orbital shaker (150 rpm) for six days. The antibody-IL-2 fusion proteins were purified to homogeneity from the supernatant by Protein A Chromatography (Mab-Select™ SuRe™, GE17-5438-01).

Quality control of the proteins was performed by SDS-PAGE (NuPAGE™ 4-12% Bis-Tris Protein Gels, ThermoFisher) and analytic size exclusion chromatography (SEC) (GE lifesciences, Superdex 200 increase 10/300).

Results

The antibody IL-2 fusion proteins cloned and expressed with different linker lengths connecting the hIL-2 to the CDR1 of VL were expressed in Expi293 cells. The purity of all constructs was high (>95%), eluting as single peak in SEC-HPLC analysis (Table 6).

5344 ELISA

The antibody-IL-2 fusion proteins were tested on a sandwich ELISA, to assess the correct folding of the IL-2 portion. The monoclonal anti-human IL-2 antibody 5344 (BD, 555051), binding on the "free" domains of IL-2 on the fusion proteins was coated. The constructs were incubated at different dilutions on the coated 5344 and detected with anti-human IgG-Peroxidase (Sigma, A0170). The obtained signals (Absorbance 450-570 nm) were plotted as function of antibody-IL-2 fusion protein concentration (as log value). The $EC_{50}$ values were interpolated fitting the data with GraphPad Prism 8 (Table 6).

Results

The $EC_{50}$ values of the IL-2 fusion proteins or IL-2 fusion proteins of the present invention are reported in Table 6. The IL-2 moiety of all the constructs was successfully binding to the anti-IL-2 antibody (clone 5344) in ELISA and could be detected on the Fc-portion by an anti-human IgG antibody coupled to HRP.

at 37° C. in 5% $CO_2$. The HEK-Blue™ IL-2 cells supernatant was diluted 1:10 in QUANTI-Blue™ solution, for colorimetric determination of secreted embryonic alkaline phosphatase activity (SEAP), and incubated at 37° C. for 3 hours. The colorimetric analysis was performed reading the absorbances at 620 nm and plotting those against protein concentration. $E_{50}$ values were interpolated using GraphPad Prism.

Results

The functionality of the IL-2 fusion proteins was assessed using HEK-Blue™ IL-2 reporter cells, engineered to express the trimeric IL-2 receptor and to secrete SEAP upon STAT5 activation triggered by IL-2. The $EC_{50}$ values determined by colorimetric determination of SEAP for each concentration of the IL-2 antibody fusion proteins are reported in Table 7.

TABLE 7

| EC50 values on IL-2 fusion proteins | |
|---|---|
| Compound name | $EC_{50}$ (M) |
| Proleukin | 4.28E−12 |
| EAD406 | 3.59E−12 |
| XFO227 | 3.03E−12 |
| QTY065 | 3.22E−12 |
| FJC828 | 3.16E−12 |
| PGO345 | 3.20E−12 |
| DRV470 | 3.61E−12 |
| XUB802 | 3.32E−12 |
| EPK959 | 3.66E−12 |
| GYG794 | 3.90E−12 |
| DRO069 | 3.45E−12 |
| ECV200 | 3.42E−12 |
| BFC885 | 5.09E−12 |
| LPT269 | 7.35E−12 |
| DXM339 | 5.47E−12 |
| FUE433 | 4.84E−12 |
| LQM346 | 4.92E−12 |
| GLK754 | 5.58E−12 |

TABLE 6

Assessment of functionality of the IL-2 fusion proteins

| Compound name | IL-2 fusion to | Linker 1 | | Linker 2 | | Purity SEC-HPLC (%) | $EC_{50}$ to 5344 (nM) | KD to CD25 (nM) |
|---|---|---|---|---|---|---|---|---|
| EAD406 | A | 0 | AA | 1 | AA | 97.61 | 0.11 | — |
| XFO227 | A | 2 | AA | 3 | AA | 97.12 | 0.14 | — |
| QTY065 | A | 3 | AA | 4 | AA | 99.10 | 0.14 | — |
| FJC828 | A | 4 | AA | 5 | AA | 97.77 | 0.28 | — |
| PGO345 | A | 6 | AA | 7 | AA | 95.75 | 0.16 | — |
| DRV470 | A | 13 | | 14 | AA | 96.85 | 0.10 | — |
| XUB802 | A | 19 | | 20 | | 94.58 | 0.15 | — |
| EPK959 | B | 0 | AA | 1 | AA | 99.20 | 0.15 | — |
| GYG794 | B | 2 | AA | 3 | AA | 97.80 | 0.20 | — |
| DRO069 | B | 3 | AA | 4 | AA | 97.52 | 0.11 | — |
| ECV200 | B | 6 | AA | 7 | AA | 96.80 | 0.13 | — |
| BFC885 | B | 13 | | 14 | | 97.74 | 0.25 | 54.1 |
| LPT269 | C | 0 | AA | 1 | AA | 97.47 | 0.24 | 0.12 |
| DXM339 | C | 2 | AA | 3 | AA | 97.93 | 0.28 | 0.18 |
| FUE433 | C | 3 | AA | 4 | AA | 98.61 | 0.54 | 0.16 |
| LQM346 | C | 6 | AA | 7 | AA | 99.09 | 0.28 | 0.15 |
| GLK754 | C | 13 | | 14 | | 98.61 | 0.28 | 0.20 |

Example 3. IL-2 fusion protein in vitro potency

HEK Blue IL-2 reporter assay

HEK-Blue™ IL-2 reporter cells (Invivogen) were incubated with a dilution series (1:3 dilutions from 0.56 nM) of antibody-IL-2 fusion protein in growth medium for 20 hours Example 4. IL-2 fusion protein in vitro selectivity Binding affinities to CD25 measured by SPR Binding affinities of the IL-2 fusion protein to the IL-2 receptor CD25 were measured by SPR (BIAcore 3000, GE Healthcare, 33-1140587-3682). His-tagged recombinant CD25 was captured via TrisNTA Biotin on SA chips and Kinetic titration of IL-2 fusion proteins of the present invention was performed reaching concentrations up to 500 nM.

Results

Table 6 reports $K_D$ values for the IL-2 fusion proteins of the present invention to CD25. IL-2 fusion proteins to antibody A did not display binding to CD25 up to concentrations ≥500 nM. Antibody A binds IL-2 with high affinity on the CD25 binding site, thereby blocking IL-2 binding to the receptor CD25. Antibody B binds IL-2 with low affinity and allows IL-2 binding to CD25 only when fused to IL-2 with long linkers (≥13 and 14 amino acids). Antibody C has no affinity for IL-2 and allows CD25 binding of its fused IL-2 with any linker length.

Competition with mouse anti-IL2 antibody specific for CD25 binding site

The antibody-IL-2 fusion proteins were tested on a competition ELISA assay with the antibody Nara1 (Arenas-Ramirez N., Sci Transl Med 2016), which has the same binding site to IL-2 as the IL-2Rα(CD25). The monoclonal anti-human IL-2 antibody Nara1 was coated on a plate. The constructs of this invention were incubated at different dilutions on the coated Nara1 and detected with anti-human IgG-Peroxidase (Sigma, A0170). The obtained signals (Absorbance 450-570 nm, OD) were plotted as function of antibody-IL-2 fusion protein concentration (as log value). The Cut Point (CP) for each 96-well plate was calculated as:

Mean Background OD +2.33×Standard deviation (SD)

Results

We evaluated binding to Nara1 by ELISA as estimate of how exposed the IL-2 portion of the fusion proteins is to CD25 binding. Table 8 shows the lowest concentration of IL-2 fusion protein construct at which a signal ≥Cut-off was detected.

TABLE 8

Binding ability of the fusion protein to IL-2

| Compound name | Lowest concentration (nM) $OD_{450-570}$ ≥ CP |
|---|---|
| EAD406 | 7.5 |
| XFO227 | 2.5 |
| QTY065 | 22.5 |
| FJC828 | 2.5 |
| PGO345 | 0.83 |
| DRV470 | 0.83 |
| XUB802 | 0.28 |
| EPK959 | 7.5 |
| GYG794 | 0.83 |
| DRO069 | 0.83 |
| ECV200 | 0.28 |
| BFC885 | <0.09 |
| LPT269 | <0.09 |
| DXM339 | <0.09 |
| FUE433 | <0.09 |
| LQM346 | <0.09 |
| GLK754 | <0.09 | pSTAT5 in mouse splenocytes (EC50 of Tregs, CD8, NK)

STAT5 phosphorylation was analyzed in murine splenocytes as downstream signaling of the IL-2R activation. In order to assess the in vitro selectivity of the antibody-IL-2 fusion proteins pSTAT5 was measured in different cell populations after stimulation with Proleukin or with one of the compounds of the present invention. Freshly isolated murine splenocytes from C57BL/6 mice were incubated with a dilution series of Proleukin or IL-2-antibody fusion protein, starting from 100 nM. The cells were immediately fixed and stained with surface markers (i.e., CD25, CD3, NK1.1, CD4, CD8). After permeabilization (Perm III buffer, BD Biosciences) intracellular staining was performed (FoxP3, pSTAT5) before acquisition through Flow Cytometry. pSTAT5 mean fluorescence intensities of $CD8^+$T cells, NK cells and $CD4^+CD25^+FoxP3^+$ Tregs were plotted for each compound against molar concentration of IL-2 antibody fusion protein. EC50 values were calculated with Graph Pad Prism.

Results

Mean fluorescence intensities of pSTAT5 were plotted for each cell population and each tested compound against the log concentration (M). The obtained $EC_{50}$ values are shown in Table 9.

TABLE 9

EC50 data of IL-2 fusion proteins

| Compound name | $EC_{50}$ NK cells (nM) | $EC_{50}$ CD8 cells (nM) | $EC_{50}$ Treg cells (nM) |
|---|---|---|---|
| Proleukin | 1.4 | 4.1 | <0.016 |
| EAD406 | 5.2 | 15.7 | 22.0 |
| XFO227 | 2.7 | 8.0 | 10.6 |
| QTY065 | 2.0 | 13.9 | 8.3 |
| FJC828 | 1.9 | 5.8 | 8.4 |
| PGO345 | 2.3 | 6.6 | 7.6 |
| DRV470 | 2.4 | 7.9 | 10.3 |
| XUB802 | 5.8 | 17.1 | 12.1 |
| EPK959 | 1.9 | 16.0 | 16.0 |
| GYG794 | 1.5 | 18.6 | 4.8 |
| DRO069 | 0.9 | 6.8 | 6.6 |
| ECV200 | 0.9 | 6.9 | 3.7 |
| BFC885 | 2.0 | 26.4 | 0.9 |
| LPT269 | 1.7 | 32.0 | <0.016 |
| DXM339 | 1.3 | 18.6 | <0.016 |
| FUE433 | 1.2 | 15.7 | <0.016 |
| LQM346 | 1.8 | 25.4 | <0.016 |
| GLK754 | 2.5 | 70.5 | <0.016 |

Example 5. In vivo selectivity of IL-2 fusion protein 10 weeks old C57BL/6 mice were injected intravenously (i.v.) with 0.2 mg/kg of compound EAD406, DRV470, LPT269 or GLK754 on day 0. Blood samples on day −2, day 3 and day 6 were processed for analysis by flow cytometry. On day 6 spleens were harvested and processed for FACS analysis. Splenocytes and mouse blood cells were stained for extracellular markers (i.e. CD25, CD3, NK1.1, CD4, CD8), permeablilized (Foxp3/Transcription Factor Staining Buffer Set, eBioscience, 00-5523) and stained for FoxP3 and Ki67 intracellular markers. Stained samples were acquired by flow cytometry and data were analyzed by Flowio (V.10) and Graphpad Prism.

Results

The % of Ki67+ cells was calculated for CD8 T-cells, NK cells and regulatory T-cells and is reported as fold over vehicle for each treatment group at day 3 and day 6 in blood (Tables 10 and 11) and at day 6 for splenocytes (Table 12). Blood %$Ki67^+$ NK-cells, Treg cells and CD8T-cells were also plotted over time in FIG. 4, highlighting the pharmacodynamic effect at day 3 and day 6 after compound administration.

When injected in mice, IL-2 fusion proteins to antibody A with short or long linker (EAD406 and DRV470) selectively induced the proliferation of NK-cells and CD8 T-cells, while sparing Treg cells. IL-2 fusion proteins with antibody C were not selective and also induced the proliferation of Treg cells in blood and spleen of treated mice. These results indicate that affinity to IL-2 of the antibody in the IL-2 antibody-fusion protein is necessary in order to obtain selective increase of effector cells in vivo.

TABLE 10

Ki67+ fold over vehicle at day 3 from blood.

|  | EAD406 | DRV470 | LPT269 | GLK754 |
|---|---|---|---|---|
| CD8+ | 4.4 | 4.1 | 2.9 | 2.6 |
| NK cells | 4.2 | 4.2 | 4.8 | 4.8 |
| Tregs | 2.4 | 2.0 | 5.1 | 4.9 |

TABLE 11

Ki67+ fold over vehicle at day 6 from blood.

|  | EAD406 | DRV470 | LPT269 | GLK754 |
|---|---|---|---|---|
| CD8+ | 5.3 | 5.3 | 2.3 | 1.9 |
| NK cells | 2.9 | 2.9 | 4.8 | 4.8 |
| Tregs | 1.2 | 1.3 | 1.9 | 2.4 |

TABLE 12

Ki67+ fold over vehicle at day 6 from splenocytes.

|  | EAD406 | DRV470 | LPT269 | GLK754 |
|---|---|---|---|---|
| CD8+ | 7.0 | 6.5 | 2.4 | 1.7 |
| NK cells | 4.0 | 3.8 | 3.2 | 2.9 |
| Tregs | 1.3 | 1.8 | 2.7 | 2.7 |

Example 6. IL-2 fusion protein in vivo anti-tumor efficacy

Figure 5:
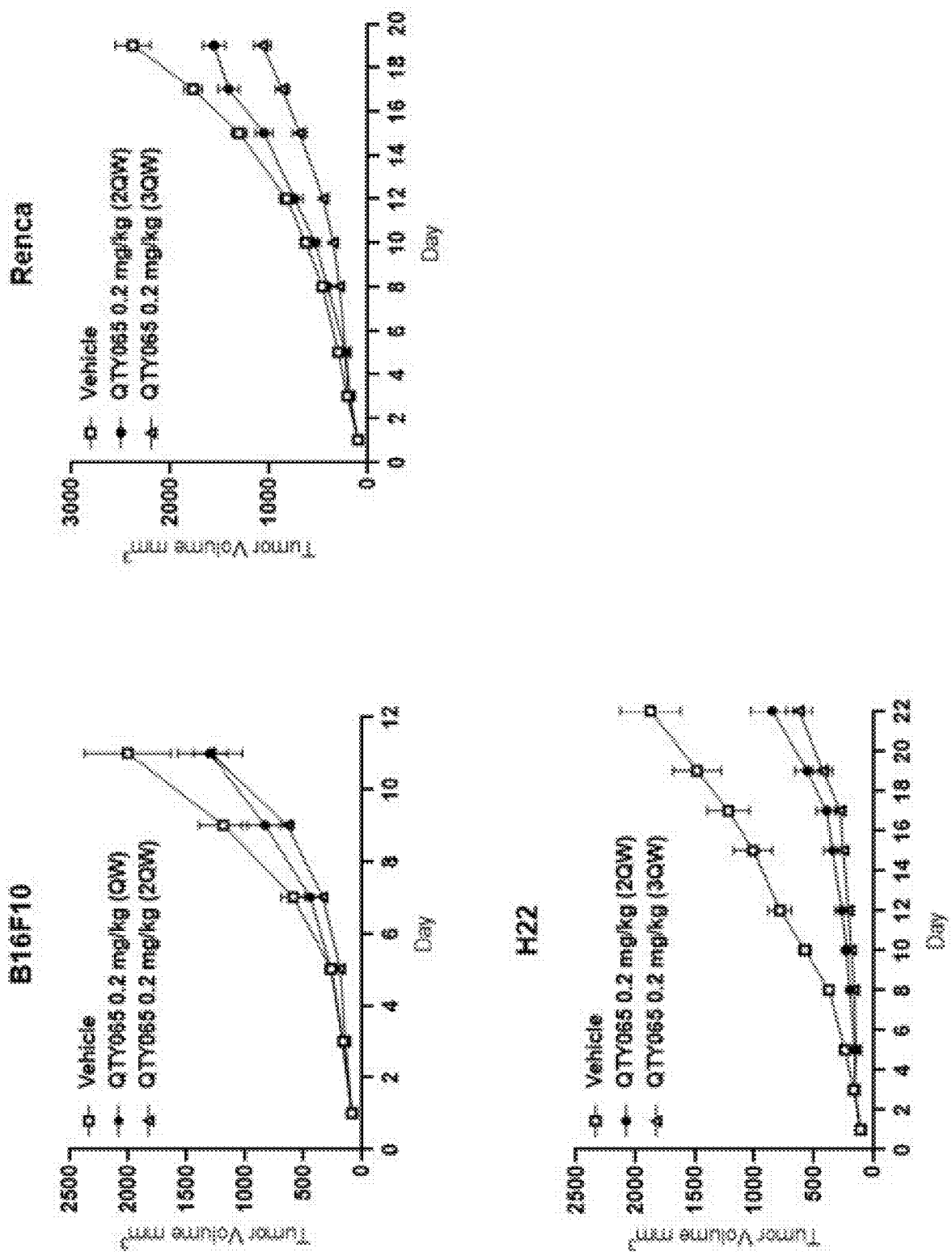
FIG. 5 represents growth curves of subcutaneous tumors in mice treated with vehicle or compounds of the invention.

For all models, the tumor cell lines were inoculated subcutaneously in the right rear flank of the mice. The mice were randomized when the mean tumor volume reached approximately 80 to 100 mm³. One day after randomization, treatment with 0.2 mg/kg IL-2 antibody-fusion protein by intravenous injection was initiated. Treatment schedules of once or twice per week (B16F10), or twice or three times per week (Renca, H22) were assessed. Tumor volumes were measured and plotted over time for each treatment group. For tumor growth inhibition (TGI) statistical analysis: homogeneity of variance across groups was checked with a Bartlett's test, if variance was equal multiple comparisons to the vehicle control group were performed by One-way ANOVA followed by Dunnett's test, otherwise a Kruskal-Wallis test followed by a Conover's test was applied. Results FIG. 5 illustrates volumes (+/. SEM, n=10 per group) of B16F10 (5A), Renca (5B) or H22 (5C) tumors in mice treated with 0.2 mg/kg antibody-IL-2 fusion protein once (QW), two times (2 QW) or three times (3 QW) per week. The greatest effect on tumor growth inhibition compared to vehicle was observed with twice (B16F10) or three times weekly (Renca, H22) treatment. Significant inhibition of tumor growth was observed in both immune-checkpoint inhibitor sensitive (H22) as well as resistant (Renca) syngeneic tumor models (Table 13), without impact on overall body weight of the animals.

TABLE 13

Tumor growth inhibition (TGI) in mice treated with IL-2 fusion protein compared to mice treated with vehicle (n = 10 per treatment group).

| Tumor Model | Tumor Type | Mouse strain | Maximum TGI | P-value |
|---|---|---|---|---|
| B16F10 | Melanoma | C57BL/6 | 46% | 0.144 |
| Renca | Renal Cell Carcinoma | BALB/c | 55% | <0.0001 |
| H22 | Hepatocellular Carcinoma | BALB/c | 67% | <0.0001 |

Sequence Table

Useful amino acids and nucleotide sequences for practicing the invention are found in Table 14.

Wild type human IL-2 and proleukin differ in the C/S bold underlined residues. Circularly permutated hIL-2 was used to create the fusion proteins of the disclosure exemplified in the previous examples and described herein.

TABLE 14

Sequence list

>IL-2

| SEQ ID NO: 1 | Human IL-2 | MYRMQLLSCIALSLALVTNSAPTSSSTKKT QLQLEHLLLDLQMILNGINNYKNPKLTRML TFKFYMPKKATELKHLQCLEEELKPLEEVLN LAQSKNFHLRPRDLISNINVIVLELKGSETTF MCEYADETATIVEFLNRWITFCQSIISTLT |
| SEQ ID NO: 2 | Proleukin ® (aldesleukin) | MAPTSSSTKKTQLQLEHLLLDLQMILNGIN NYKNPKLTRMLTFKFYMPKKATELKHLQCL EEELKPLEEVLNLAQSKNFHLRPRDLISNIN VIVLELKGSETTFMCEYADETATIVEFLNR WITFSQSIISTLT |
| SEQ ID NO: 3 | Circularly permuted hIL-2 | NFHLRPRDLISNINVIVLELKGSETTFMCEY ADETATIVEFLNRWITFCQSIISTLTPTSSST KKTQLQLEHLLLDLQMILNGINNYKNPKLT RMLTFKFYMPKKATELKHLQCLEEELKPLE EVLNLAQSK |
| SEQ ID NO: 4 | Circularly permuted Proleukin ® | NFHLRPRDLISNINVIVLELKGSETTFMCEY ADETATIVEFLNRWITFSQSIISTLTPTSSTK KTQLQLEHLLLDLQMILNGINNYKNPKLTR MLTFKFYMPKKATELKHLQCLEEELKPLEE VLNLAQSK |

TABLE 14-continued

Sequence list

>Antibody A

| SEQ ID NO: 5 | Heavy Chain (VH-CH₁,₂,₃) | EVQLVQSGAEVKKPGESLKISCKGSYAFT NYLIEWVRQMPGKGLEWMGVINPGSGG TNYNEKFKGQVTISADKSISTAYLQWSSLK ASDTAMYYCARWRGEGYYAYFDVWGQG TTVTVSSASTKGPSVFPLAPSSKSTSGGTAA LGCLVKDYFPEPVTVSWNSGALTSGVHTF PAVLQSSGLYSLSSVVTVPSSSLGTQTYICN VNHKPSNTKVDKRVEPKSCDKTHTCPPCP APELLGGPSVFLFPPKPKDTLMISRTPEVTC VVVDVSHEDPEVKFNWYVDGVEVHNAKT KPREEQYASTYRVVSVLTVLHQDWLNGKE YKCKVSNKALPAPIEKTISKAKGQPREPQVY TLPPSREEMTKNQVSLTCLVKGFYPSDIAV EWESNGQPENNYKTTPPVLDSDGSFFLYS KLTVDKSRWQQGNVFSCSVMHEALHNHY TQKSLSLSPGK |
| --- | --- | --- |
| SEQ ID NO: 6 | Light Chain (VL-CL) | AIRLTQSPSSFSASTGDRVTITCKASQSVDY QGDSYMNWYQQKPGKAPKLLIYAASNLE SGVPSRFSGSGSGTDFTLTISSLQSEDFATY YCQQSNEDPYTFGGGTKVEIKRTVAAPSVF IFPPSDEQLKSGTASVVCLLNNFYPREAKV QWKVDNALQSGNSQESVTEQDSKDSTYS LSSTLTLSKADYEKHKVYACEVTHQGLSSPV TKSFNRGEC |
| SEQ ID NO: 7 | VH | EVQLVQSGAEVKKPGESLKISCKGSYAFT NYLIEWVRQMPGKGLEWMGVINPGSGG TNYNEKFKGQVTISADKSISTAYLQWSSLK ASDTAMYYCARWRGEGYYAYFDVWGQG TTVTVSS |
| SEQ ID NO: 8 | DNA VH | GAAGTGCAGCTGGTGCAGTCTGGCGCTG AAGTGAAGAAGCCCGGCGAGTCCCTGA AGATCTCCTGCAAGGGCTCCGGCTACGC CTTCACCAACTACCTGATCGAGTGGGTCC GACAGATGCCCGGCAAGGGCCTGGAGT GGATGGGCGTGATCAACCCCGGCTCCGG CGGCACCAACTACAACGAGAAGTTCAAG GGCCAAGTCACAATCTCCGCCGACAAGT CCATCTCCACCGCCTACCTGCAGTGGTCC TCCCTGAAGGCCTCCGACACCGCCATGT ACTACTGCGCCAGATGGCGGGGAGAAG GCTACTACGCCTACTTCGACGTGTGGGG CCAGGGCACCACCGTGACCGTGTCCTCT |
| SEQ ID NO: 9 | VL | AIRLTQSPSSFSASTGDRVTITCKASQSVDY QGDSYMNWYQQKPGKAPKLLIYAASNLE SGVPSRFSGSGSGTDFTLTISSLQSEDFATY YCQQSNEDPYTFGGGTKVEIK |
| SEQ ID NO: 10 | DNA VL | GCCATCAGACTGACCCAGAGCCCCTCCA GCTTCTCCGCCTCCACCGGCGACAGAGT GACCATCACATGCAAGGCCTCCCAGTCC GTGGACTACCAGGGCGACTCCTACATGA ACTGGTATCAGCAGAAGCCCGGCAAGGC CCCTAAGCTGCTGATCTACGCCGCCTCCA ACCTGGAATCCGGCGTGCCCTCCCGGTT CTCCGGCTCTGGCTCTGGCACCGACTTCA CCCTGACCATCTCCAGCCTGCAGTCCGAG GACTTCGCCACCTACTACTGCCAGCAGTC CAACGAGGACCCCTACACCTTCGGCGGA GGCACCAAAGTGGAAATCAAG |
| SEQ ID NO: 11 (Kabat) | HCDR1 | GYAFTNYLIE |
| SEQ ID NO: 12 (Kabat) | HCDR2 | VINPGSGGTNYNEKFKG |
| SEQ ID NO: 13 (Kabat) | HCDR3 | WRGEGYYAYFDV |
| SEQ ID NO: 14 (Kabat) | LCDR1 | KASQSVDYQGDSYMN |
| SEQ ID NO: 22 | LCDR1 | KASQSVDYXXDSYMN |
| SEQ ID NO: 15 (Kabat) | LCDR2 | AASNLES |

TABLE 14-continued

| Sequence list | | |
|---|---|---|
| SEQ ID NO: 16 (Kabat) | LCDR3 | QQSNEDPYT |
| SEQ ID NO: 17 consensus | HCDR1 | GYX1FX2X3YLIE |
| Consensus sequences are based on differences between antibodies A and B. | HCDR1 variable amino acids | X1 = A or T; X2 = S or T; X3 = N or S |
| SEQ ID NO: 18 | HCDR2 consensus | VINPGSGGTNYX1X2X3X4KG |
| | HCDR2 variable amino acids | X1 = N or A; X2 = E or D; X3 = K or S; X4 = F or V |
| SEQ ID NO: 19 | HCDR3 consensus | WRGX1GYYAYFDV |
| | HCDR3 variable amino acids | X1 = E or D |
| SEQ ID NO: 20 | LCDR1 consensus | X1ASQSVX2YX3GDSYMN |
| | LCDR1 variable amino acids | X1 = R or K; X2 = S or D; X3 = D or Q |
| SEQ ID NO: 21 | LCDR2 consensus | AASNLX1S |
| | LCDR2 variable amino acids | X1 = E or A |
| SEQ ID NO: 16 (Kabat) | LCDR3 variable amino acids | QQSNEDPYT |
| SEQ ID NO: 22 | LCDR1 in fusion protein | KASQSVDYXXDSYMN |
| >Antibody B | | |
| SEQ ID NO: 23 | Heavy Chain (VH-CH$_{1,2,3}$) | QVQLVESGGGVVQPGRSLRLSCAASGYTF SSYLIEWVRQAPGKGLEWVAVINPGSGGT NYADSVKGRFTISADKSKNTAYLQMNSLR AEDTAVYYCARWRGDGYYAYFDVWGQG TTVTVSSASTKGPSVFPLAPSSKSTSGGTAA LGCLVKDYFPEPVTVSWNSGALTSGVHTF PAVLQSSGLYSLSSVVTVPSSSLGTQTYICN VNHKPSNTKVDKRVEPKSCDKTHTCPPCP APELLGGPSVFLFPPKPKDTLMISRTPEVTC VVVDVSHEDPEVKFNWYVDGVEVHNAKT KPREEQYNSTYRVVSVLTVLHQDWLNGKE YKCKVSNKALPAPIEKTISKAKGQPREPQVY TLPPSREEMTKNQVSLTCLVKGFYPSDIAV EWESNGQPENNYKTTPPVLDSDGSFFLYS KLTVDKSRWQQGNVFSCSVMHEALHNHY TQKSLSLSPGK |
| SEQ ID NO: 24 | Light Chain (VL-CL) | EIVLTQSPATLSVSPGERATLSCRASQSVSY DGDSYMNWYQQKPGQAPRLLIYAASNLA SGIPARFSGSGSGTEFTLTISSLQSEDAAVYY CQQSNEDPYTFGGGTKVEIKRTVAAPSVFI FPPSDEQLKSGTASVVCLLNNFYPREAKVQ WKVDNALQSGNSQESVTEQDSKDSTYSLS STLTLSKADYEKHKVYACEVTHQGLSSPVT KSFNRGEC |
| SEQ ID NO: 25 | VH | QVQLVESGGGVVQPGRSLRLSCAASGYTF SSYLIEWVRQAPGKGLEWVAVINPGSGGT NYADSVKGRFTISADKSKNTAYLQMNSLR AEDTAVYYCARWRGDGYYAYFDVWGQG TTVTVSS |
| SEQ ID NO: 26 | VL | EIVLTQSPATLSVSPGERATLSCRASQSVSY DGDSYMNWYQQKPGQAPRLLIYAASNLA SGIPARFSGSGSGTEFTLTISSLQSEDAAVYY CQQSNEDPYTFGGGTKVEIK |
| SEQ ID NO: 27 (Kabat) | HCDR1 | GYTFSSYLIE |

TABLE 14-continued

| Sequence list | | |
|---|---|---|
| SEQ ID NO: 28 (Kabat) | HCDR2 | VINPGSGGTNYADSVKG |
| SEQ ID NO: 29 (Kabat) | HCDR3 | WRGDGYYAYFDV |
| SEQ ID NO: 30 (Kabat) | LCDR1 | RASQSVSYDGDSYMN |
| SEQ ID NO: 33 | LCDR1 | RASQSVSYXXDSYMN |
| SEQ ID NO: 31 (Kabat) | LCDR2 | AASNLAS |
| SEQ ID NO: 32 (Kabat) | LCDR3 | QQSNEDPYT |
| SEQ ID NO: 33 (Kabat) | LCDR1 in fusion protein | RASQSVSYXXDSYMN |
| >Antibody C | | |
| SEQ ID NO: 34 | Heavy Chain (VH-CH$_{1,2,3}$) | EVQLVQSGAEVKKPGESLKISCKGSGYSFT NFYIHWVRQAPGQRLEWMGSIYPNYGDT AYNQKFKDRFVFSLDTSVSTAYLQISSLKAE DTAVYYCARGYSYAMDYWGQGTTVTVSS ASTKGPSVFPLAPSSKSTSGGTAALGCLVK DYFPEPVTVSWNSGALTSGVHTFPAVLQS SGLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQ YNSTYRVVSVLTVLHQDWLNGKEYKCKVS NKALPAPIEKTISKAKGQPREPQVYTLPPSR DELTKNQVSLTCLVKGFYPSDIAVEWESNG QPENNYKTTPPVLDSDGSFFLYSKLTVDKS RWQQGNVFSCSVMHEALHNHYTQKSLSL SPGK |
| SEQ ID NO: 35 | Light Chain (VL-CL) | DIQMTQSPSSVSASVGDRVTITCSASQGIS GDLNWYQQKPGKAPKLLIYHTSSLHSGVP SRFSGSGSGTDFTLTISSLQPEDFATYYCQY YSKDLLTFGGGTKLEIKRTVAAPSVFIFPPSD EQLKSGTASVVCLLNNFYPREAKVQWKVD NALQSGNSQESVTEQDSKDSTYSLSSTLTLS KADYEKHKVYACEVTHQGLSSPVTKSFNR GEC |
| SEQ ID NO: 36 | VH | EVQLVQSGAEVKKPGESLKISCKGSGYSFT NFYIHWVRQAPGQRLEWMGSIYPNYGDT AYNQKFKDRFVFSLDTSVSTAYLQISSLKAE DTAVYYCARGYSYAMDYWGQGTTVTVSS |
| SEQ ID NO: 37 | VL | DIQMTQSPSSVSASVGDRVTITCSASQGIS GDLNWYQQKPGKAPKLLIYHTSSLHSGVP SRFSGSGSGTDFTLTISSLQPEDFATYYCQY YSKDLLTFGGGTKLEIK |
| SEQ ID NO: 38 (Kabat) | HCDR1 | GYSFTNFYIH |
| SEQ ID NO: 39 (Kabat) | HCDR2 | SIYPNYGDTAYNQKFKD |
| SEQ ID NO: 40 (Kabat) | HCDR3 | GYSYAMDY |
| SEQ ID NO: 41 (Kabat) | LCDR1 | VTITCSASQGISGDL |
| SEQ ID NO: 42 (Kabat) | LCDR2 | HTSSLHS |
| SEQ ID NO: 43 (Kabat) | LCDR3 | QYYSKDLLT |
| SEQ ID NO: 44 (Kabat) | LCDR1 in fusion protein | VTITCSASXXISGDL |
| >Linkers | | |
| | G | G |
| | G2 | GG |
| | G3 | GGG |
| SEQ ID NO: 48 | G4 | GGGG |

TABLE 14-continued

Sequence list

| SEQ ID NO: 49 | (G4S) | GGGGS |
|---|---|---|
| SEQ ID NO: 50 | (G4S)G | GGGGSG |
| SEQ ID NO: 51 | (G4S)GG | GGGGSGG |
| SEQ ID NO: 52 | (G4S)2GGG | GGGGSGGGGSGGG |
| SEQ ID NO: 53 | (G4S)2GGGG | GGGGSGGGGSGGGG |
| SEQ ID NO: 54 | (G4S)3GGGG | GGGGSGGGGSGGGGSGGGG |
| SEQ ID NO: 55 | (G4S)4 | GGGGSGGGGSGGGGSGGGGS |

Fusion proteins
>EAD406

| SEQ ID NO: 56 | VL-linker 1(0) - IL2-linker 2(1) - VL-CL | AIRLTQSPSSFSASTGDRVTITCKASQSVDY NFHLRPRDLISNINVIVLELKGSETTFMCEY ADETATIVEFLNRWITFSQSIISTLTPTSSSTK KTQLQLEHLLLDLQMILNGINNYKNPKLTR MLTFKFYMPKKATELKHLQCLEEELKPLEE VLNLAQSKGDSYMNWYQQKPGKAPKLLI YAASNLESGVPSRFSGSGSGTDFTLTISSLQ SEDFATYYCQQSNEDPYTFGGGTKVEIKRT VAAPSVFIFPPSDEQLKSGTASVVCLLNNFY PREAKVQWKVDNALQSGNSQESVTEQDS KDSTYSLSSTLTLSKADYEKHKVYACEVTHQ GLSSPVTKSFNRGEC |

>XFO227

| SEQ ID NO: 57 | VL-linker 1(2) - IL2-linker 2 (3) - VL-CL | AIRLTQSPSSFSASTGDRVTITCKASQSVDY GGNFHLRPRDLISNINVIVLELKGSETTFMC EYADETATIVEFLNRWITFSQSIISTLTPTSSS TKKTQLQLEHLLLDLQMILNGINNYKNPKL TRMLTFKFYMPKKATELKHLQCLEEELKPL EEVLNLAQSKGGGDSYMNWYQQKPGKA PKLLIYAASNLESGVPSRFSGSGSGTDFTLTI SSLQSEDFATYYCQQSNEDPYTFGGGTKV EIKRTVAAPSVFIFPPSDEQLKSGTASVVCLL NNFYPREAKVQWKVDNALQSGNSQESVT EQDSKDSTYSLSSTLTLSKADYEKHKVYACE VTHQGLSSPVTKSFNRGEC |

>QTY065

| SEQ ID NO: 58 | VL-linker 1(3) - IL2-linker 2(4) - VL-CL | AIRLTQSPSSFSASTGDRVTITCKASQSVDY GGGNFHLRPRDLISNINVIVLELKGSETTFM CEYADETATIVEFLNRWITFSQSIISTLTPTS SSTKKTQLQLEHLLLDLQMILNGINNYKN PKLTRMLTFKFYMPKKATELKHLQCLEEELK PLEEVLNLAQSKGGGGDSYMNWYQQKP GKAPKLLIYAASNLESGVPSRFSGSGSGTDF TLTISSLQSEDFATYYCQQSNEDPYTFGGG TKVEIKRTVAAPSVFIFPPSDEQLKSGTASV VCLLNNFYPREAKVQWKVDNALQSGNSQ ESVTEQDSKDSTYSLSSTLTLSKADYEKHKV YACEVTHQGLSSPVTKSFNRGEC |

>FJC828

| SEQ ID NO: 59 | VL-linker 1(4) - IL2-linker 2(5) - VL-CL | AIRLTQSPSSFSASTGDRVTITCKASQSVDY GGGGNFHLRPRDLISNINVIVLELKGSETTF MCEYADETATIVEFLNRWITFSQSIISTLTPT SSSTKKTQLQLEHLLLDLQMILNGINNYKN PKLTRMLTFKFYMPKKATELKHLQCLEEEL KPLEEVLNLAQSKGGGGSDSYMNWYQQK PGKAPKLLIYAASNLESGVPSRFSGSGSGTD FTLTISSLQSEDFATYYCQQSNEDPYTFGG GTKVEIKRTVAAPSVFIFPPSDEQLKSGTAS VVCLLNNFYPREAKVQWKVDNALQSGNS QESVTEQDSKDSTYSLSSTLTLSKADYEKHK VYACEVTHQGLSSPVTKSFNRGEC |

TABLE 14-continued

| Sequence list | | |
|---|---|---|
| >PGO345 | | |
| SEQ ID NO: 60 | VL-linker 1(6) - IL2-linker 2(7) - VL-CL | AIRLTQSPSSFSASTGDRVTITCKASQSVDYGGGGSG<u>NFHLRPRDLISNINVIVLELKGSETTFMCEYADETATIVEFLNRWITFSQSIISTLTPTSSSTKKTQLQLEHLLLDLQMILNGINNYKNPKLTRMLTFKFYMPKKATELKHLQCLEEELKPLEEVLNLAQSK</u>GGGGSGGGDSYMNWYQQKPGKAPKLLIYAASNLESGVPSRFSGSGSGTDFTLTISSLQSEDFATYYCQQSNEDPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| >DRV470 | | |
| SEQ ID NO: 61 | VL-linker 1(13) - IL2-linker 2(14) - VL - CL | AIRLTQSPSSFSASTGDRVTITCKASQSVDYGGGGSGGGGSGGGG<u>NFHLRPRDLISNINVIVLELKGSETTFMCEYADETATIVEFLNRWITFSQSIISTLTPTSSSTKKTQLQLEHLLLDLQMILNGINNYKNPKLTRMLTFKFYMPKKATELKHLQCLEEELKPLEEVLNLAQSK</u>GGGGSGGGGSGGGGDSYMNWYQQKPGKAPKLLIYAASNLESGVPSRFSGSGSGTDFTLTISSLQSEDFATYYCQQSNEDPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| >XUB802 | | |
| SEQ ID NO: 62 | VL-linker 1(19) - IL2-linker 2(20) - VL-CL | AIRLTQSPSSFSASTGDRVTITCKASQSVDYGGGGSGGGGSGGGGSGGGG<u>NFHLRPRDLISNINVIVLELKGSETTFMCEYADETATIVEFLNRWITFSQSIISTLTPTSSSTKKTQLQLEHLLLDLQMILNGINNYKNPKLTRMLTFKFYMPKKATELKHLQCLEEELKPLEEVLNLAQSK</u>GGGGSGGGGSGGGGSGGGGSDSYMNWYQQKPGKAPKLLIYAASNLESGVPSRFSGSGSGTDFTLTISSLQSEDFATYYCQQSNEDPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| >EPK959 | | |
| SEQ ID NO: 63 | VL-linker 1(0) - IL2-linker 2(1) - VL-CL | EIVLTQSPATLSVSPGERATLSCRASQSVSY<u>NFHLRPRDLISNINVIVLELKGSETTFMCEYADETATIVEFLNRWITFSQSIISTLTPTSSSTKKTQLQLEHLLLDLQMILNGINNYKNPKLTRMLTFKFYMPKKATELKHLQCLEEELKPLEEVLNLAQSK</u>GDSYMNWYQQKPGQAPRLLIYAASNLASGIPARFSGSGSGTEFTLTISSLQSEDAAVYYCQQSNEDPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| >GYG794 | | |
| SEQ ID NO: 64 | VL-linker 1(2) - IL2-linker 2(3) - VL-CL | EIVLTQSPATLSVSPGERATLSCRASQSVSYGG<u>NFHLRPRDLISNINVIVLELKGSETTFMCEYADETATIVEFLNRWITFSQSIISTLTPTSSSTKKTQLQLEHLLLDLQMILNGINNYKNPKLTRMLTFKFYMPKKATELKHLQCLEEELKPLEEVLNLAQSK</u>GGGDSYMNWYQQKPGQAPRLLIYAASNLASGIPARFSGSGSGTEFTLTISSLQSEDAAVYYCQQSNEDPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 14-continued

Sequence list

>DRO069

SEQ ID NO: 65 | VL-linker 1(3) - IL2-linker 2(4) - VL-CL | EIVLTQSPATLSVSPGERATLSCRASQSVSYGGGNFHLRPRDLISNINVIVLELKGSETTFMCEYADETATIVEFLNRWITFSQSIISTLTPTSSSTKKTQLQLEHLLLDLQMILNGINNYKNPKLTRMLTFKFYMPKKATELKHLQCLEEELKPLEEVLNLAQSKGGGGDSYMNWYQQKPGQAPRLLIYAASNLASGIPARFSGSGSGTEFTLTISSLQSEDAAVYYCQQSNEDPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

>ECV200

SEQ ID NO: 66 | VL-linker 1(6) - IL2-linker 2(7) - VL-CL | EIVLTQSPATLSVSPGERATLSCRASQSVSYGGGGSGNFHLRPRDLISNINVIVLELKGSETTFMCEYADETATIVEFLNRWITFSQSIISTLTPTSSSTKKTQLQLEHLLLDLQMILNGINNYKNPKLTRMLTFKFYMPKKATELKHLQCLEEELKPLEEVLNLAQSKGGGGSGGDSYMNWYQQKPGQAPRLLIYAASNLASGIPARFSGSGSGTEFTLTISSLQSEDAAVYYCQQSNEDPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

>BFC885

SEQ ID NO: 67 | VL-linker 1(13) - IL2-linker 2(14) - VL-CL | EIVLTQSPATLSVSPGERATLSCRASQSVSYGGGGSGGGGSGGGNFHLRPRDLISNINVIVLELKGSETTFMCEYADETATIVEFLNRWITFSQSIISTLTPTSSSTKKTQLQLEHLLLDLQMILNGINNYKNPKLTRMLTFKFYMPKKATELKHLQCLEEELKPLEEVLNLAQSKGGGGSGGGSGGGGDSYMNWYQQKPGQAPRLLIYAASNLASGIPARFSGSGSGTEFTLTISSLQSEDAAVYYCQQSNEDPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

>LPT269

SEQ ID NO: 68 | VL-linker 1(0) - IL2-linker 2(1) - VL-CL | DIQMTQSPSSVSASVGDRVTITCSASQGISGNFHLRPRDLISNINVIVLELKGSETTFMCEYADETATIVEFLNRWITFSQSIISTLTPTSSSTKKTQLQLEHLLLDLQMILNGINNYKNPKLTRMLTFKFYMPKKATELKHLQCLEEELKPLEEVLNLAQSKGDLNWYQQKPGKAPKLLIYHTSSLHSGVPSRFSGSGSGTDFTLTISSLQPEDFATYYCQYYSKDLLTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

>DXM339

SEQ ID NO: 69 | VL-linker 1(2) - IL2-linker 2(3) - VL-CL | DIQMTQSPSSVSASVGDRVTITCSASQGISGGGNFHLRPRDLISNINVIVLELKGSETTFMCEYADETATIVEFLNRWITFSQSIISTLTPTSSSTKKTQLQLEHLLLDLQMILNGINNYKNPKLTRMLTFKFYMPKKATELKHLQCLEEELKPLEEVLNLAQSKGGGDLNWYQQKPGKAPKLLIYHTSSLHSGVPSRFSGSGSGTDFTLTISSLQPEDFATYYCQYYSKDLLTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

TABLE 14-continued

Sequence list

>FEU443

| SEQ ID NO: 70 | VL-linker 1(3) - IL2-linker 2(4) - VL-CL | DIQMTQSPSSVSASVGDRVTITCSASQGIS GGGGGGGNFHLRPRDLISNINVIVLELKGSETTF MCEYADETATIVEFLNRWITFSQSIISTLTPT SSSTKKTQLQLEHLLLDLQMILNGINNYKN PKLTRMLTFKFYMPKKATELKHLQCLEEEL KPLEEVLNLAQSKGGGGDLNWYQQKPGK APKLLIYHTSSLHSGVPSRFSGSGSGTDFTL TISSLQPEDFATYYCQYYSKDLLTFGGGTKL EIKRTVAAPSVFIFPPSDEQLKSGTASVVCLL NNFYPREAKVQWKVDNALQSGNSQESVT EQDSKDSTYSLSSTLTLSKADYEKHKVYACE VTHQGLSSPVTKSFNRGEC |

>LQM346

| SEQ ID NO: 71 | VL-linker 1(6) - IL2-linker 2(7) - VL-CL | DIQMTQSPSSVSASVGDRVTITCSASQGIS GGGGGGSGNFHLRPRDLISNINVIVLELKGS ETTFMCEYADETATIVEFLNRWITFSQSIIST LTPTSSSTKKTQLQLEHLLLDLQMILNGINN YKNPKLTRMLTFKFYMPKKATELKHLQCLE EELKPLEEVLNLAQSKGGGGSGGDLNWY QQKPGKAPKLLIYHTSSLHSGVPSRFSGSG SGTDFTLTISSLQPEDFATYYCQYYSKDLLTF GGGTKLEIKRTVAAPSVFIFPPSDEQLKSGT ASVVCLLNNFYPREAKVQWKVDNALQSG NSQESVTEQDSKDSTYSLSSTLTLSKADYEK HKVYACEVTHQGLSSPVTKSFNRGEC |

>GLK754

| SEQ ID NO: 72 | VL-linker 1(13) - IL2-linker 2(14) - VL-CL | DIQMTQSPSSVSASVGDRVTITCSASQGIS GGGGGGSGGGGSGGGGNFHLRPRDLISNIN VIVLELKGSETTFMCEYADETATIVEFLNR WITFSQSIISTLTPTSSSTKKTQLQLEHLLLDL QMILNGINNYKNPKLTRMLTFKFYMPKKA TELKHLQCLEEELKPLEEVLNLAQSKGGGG SGGGGSGGGGDLNWYQQKPGKAPKLLIY HTSSLHSGVPSRFSGSGSGTDFTLTISSLQP EDFATYYCQYYSKDLLTFGGGTKLEIKRTVA APSVFIFPPSDEQLKSGTASVVCLLNNFYPR EAKVQWKVDNALQSGNSQESVTEQDSKD STYSLSSTLTLSKADYEKHKVYACEVTHQGL SSPVTKSFNRGEC |

>hIgG1

| SEQ ID NO: 73 | Constant HC | ASTKGPSVFPLAPSSKSTSGGTAALGCLVK DYFPEPVTVSWNSGALTSGVHTFPAVLQS SGLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQ YNSTYRVVSVLTVLHQDWLNGKEYKCKVS NKALPAPIEKTISKAKGQPREPQVYTLPPSR EEMTKNQVSLTCLVKGFYPSDIAVEWESN GQPENNYKTTPPVLDSDGSFFLYSKLTVDK SRWQQGNVFSCSVMHEALHNHYTQKSLS LSPGK |
| SEQ ID NO: 74 | DNA Constant HC | GCGTCGACCAAGGGCCCCAGCGTGTTCC CCCTGGCCCCCAGCAGCAAGAGCACCAG CGGCGGCACAGCCGCCCTGGGCTGCCTG GTGAAGGACTACTTCCCCGAGCCCGTGA CCGTGTCCTGGAACAGCGGAGCCCTGAC CTCCGGCGTGCACACCTTCCCCGCCGTGC TGCAGAGCAGCGGCCTGTACAGCCTGTC CAGCGTGGTGACAGTGCCCAGCAGCAGC CTGGGCACCCAGACCTACATCTGCAACG TGAACCACAAGCCCAGCAACACCAAGGT GGACAAGAGAGTGGAGCCCAAGAGCTG CGACAAGACCCACACCTGCCCCCCCTGCC CAGCCCCAGAGCTGCTGGGCGGACCCTC CGTGTTCCTGTTCCCCCCCAAGCCCAAGG ACACCCTGATGATCAGCAGGACCCCCGA GGTGACCTGCGTGGTGGTGGACGTGAG CCACGAGGACCCAGAGGTGAAGTTCAAC |

TABLE 14-continued

Sequence list

|  |  |  | TGGTACGTGGACGGCGTGGAGGTGCAC<br>AACGCCAAGACCAAGCCCAGAGAGGAG<br>CAGTACAACAGCACCTACAGGGTGGTGT<br>CCGTGCTGACCGTGCTGCACCAGGACTG<br>GCTGAACGGCAAGGAATACAAGTGCAA<br>GGTCTCCAACAAGGCCCTGCCAGCCCCC<br>ATCGAAAAGACCATCAGCAAGGCCAAGG<br>GCCAGCCACGGGAGCCCCAGGTGTACAC<br>CCTGCCCCCTCCCGGGAGGAGATGACC<br>AAGAACCAGGTGTCCCTGACCTGTCTGG<br>TGAAGGGCTTCTACCCCAGCGACATCGC<br>CGTGGAGTGGGAGAGCAACGGCCAGCC<br>CGAGAACAACTACAAGACCACCCCCCCA<br>GTGCTGGACAGCGACGGCAGCTTCTTCC<br>TGTACAGCAAGCTGACCGTGGACAAGTC<br>CAGGTGGCAGCAGGGCAACGTGTTCAG<br>CTGCAGCGTGATGCACGAGGCCCTGCAC<br>AACCACTACACCCAGAAGAGCCTGAGCC<br>TGTCCCCCGGCAAG |
|---|---|---|---|
| >hIgG2 |  |  |  |
| SEQ ID NO: 75 |  | Constant HC | ASTKGPSVFPLAPCSRSTSESTAALGCLVKD<br>YFPEPVTVSWNSGALTSGVHTFPAVLQSS<br>GLYSLSSVVTVPSSNFGTQTYTCNVDHKPS<br>NTKVDKTVERKCCVECPPCPAPPVAGPSV<br>FLFPPKPKDTLMISRTPEVTCVVVDVSHED<br>PEVQFNWYVDGVEVHNAKTKPREEQFNS<br>TFRVVSVLTVVHQDWLNGKEYKCKVSNK<br>GLPAPIEKTISKTKGQPREPQVYTLPPSREE<br>MTKNQVSLTCLVKGFYPSDIAVEWESNGQ<br>PENNYKTTPPMLDSDGSFFLYSKLTVDKSR<br>WQQGNVFSCSVMHEALHNHYTQKSLSLS<br>PGK |
| SEQ ID NO: 76 |  | DNA Constant HC | GCCAGCACCAAGGGCCCCAGCGTGTTCC<br>CCCTGGCCCCCTGCAGCAGAAGCACCAG<br>CGAGAGCACAGCCGCCCTGGGCTGCCTG<br>GTGAAGGACTACTTCCCCGAGCCAGTGA<br>CCGTGTCCTGGAACAGCGGAGCCCTGAC<br>CAGCGGCGTGCACACCTTCCCCGCCGTG<br>CTGCAGAGCAGCGGCCTGTACAGCCTGT<br>CCAGCGTGGTGACCGTGCCCAGCAGCAA<br>CTTCGGCACCCAGACCTACACCTGCAAC<br>GTGGACCACAAGCCCAGCAACACCAAGG<br>TGGACAAGACCGTGGAGAGGAAGTGCT<br>GCGTGGAGTGCCCCCCCTGCCCAGCCCC<br>CCCAGTGGCCGGACCCTCCGTGTTCCTGT<br>TCCCCCCCAAGCCCAAGGACACCCTGAT<br>GATCAGCAGGACCCCCGAGGTGACCTGC<br>GTGGTGGTGGACGTGAGCCACGAGGAC<br>CCAGAGGTGCAGTTCAACTGGTACGTGG<br>ACGGCGTGGAGGTGCACAACGCCAAGA<br>CCAAGCCCAGAGAGGAACAGTTTAACAG<br>CACCTTCAGGGTGGTGTCCGTGCTGACC<br>GTGGTGCACCAGGACTGGCTGAACGGC<br>AAAGAGTACAAGTGCAAGGTCTCCAACA<br>AGGGCCTGCCAGCCCCCATCGAGAAAAC<br>CATCAGCAAGACCAAGGGCCAGCCACG<br>GGAGCCCCAGGTGTACACCCTGCCCCCC<br>AGCCGGGAGGAAATGACCAAGAACCAG<br>GTGTCCCTGACCTGTCTGGTGAAGGGCT<br>TCTACCCCAGCGACATCGCCGTGGAGTG<br>GGAGAGCAACGGCCAGCCCGAGAACAA<br>CTACAAGACCACCCCCCCCATGCTGGAC<br>AGCGACGGCAGCTTCTTCCTGTACAGCA<br>AGCTGACAGTGGACAAGAGCAGGTGGC<br>AGCAGGGCAACGTGTTCAGCTGCAGCGT<br>GATGCACGAGGCCCTGCACAACCACTAC<br>ACCCAGAAGAGCCTGAGCCTGTCCCCCG<br>GCAAG |
| >hIgG3 |  |  |  |
| SEQ ID NO: 77 |  | Constant HC | ASTKGPSVFPLAPCSRSTSGGTAALGCLVK<br>DYFPEPVTVSWNSGALTSGVHTFPAVLQS<br>SGLYSLSSVVTVPSSSLGTQTYTCNVNHKPS<br>NTKVDKRVELKTPLGDTTHTCPRCPEPKSC |

TABLE 14-continued

Sequence list

| | | |
|---|---|---|
| | | DTPPPCPRCPEPKSCDTPPPCPRCPEPKSC<br>DTPPPCPRCPAPELLGGPSVFLFPPKPKDTL<br>MISRTPEVTCVVVDVSHEDPEVQFKWYVD<br>GVEVHNAKTKPREEQYNSTFRVVSVLTVL<br>HQDWLNGKEYKCKVSNKALPAPIEKTISKT<br>KGQPREPQVYTLPPSREEMTKNQVSLTCL<br>VKGFYPSDIAVEWESSGQPENNYNTTPPM<br>LDSDGSFFLYSKLTVDKSRWQQGNIFSCSV<br>MHEALHNRFTQKSLSLSPGK |
| SEQ ID NO: 78 | DNA Constant HC | GCCAGCACCAAGGGCCCCAGCGTGTTCC<br>CCCTGGCCCCCTGCAGCCGGAGCACCAG<br>CGGCGGCACCGCCGCCCTGGGCTGCCTG<br>GTGAAGGACTACTTCCCCGAGCCCGTGA<br>CCGTGAGCTGGAACAGCGGCGCCCTGAC<br>CAGCGGCGTGCACACCTTCCCCGCCGTG<br>CTGCAGAGCAGCGGCCTGTACAGCCTGA<br>GCAGCGTGGTGACCGTGCCCAGCAGCA<br>GCCTGGGCACCCAGACCTACACCTGCAA<br>CGTGAACCACAAGCCCAGCAACACCAAG<br>GTGGACAAGCGGGTGGAGCTGAAGACC<br>CCCCTGGGCGACACCACCCACACCTGCC<br>CCCGGTGCCCCGAGCCCAAGAGCTGCGA<br>CACCCCCCCCCCTGCCCCGGTGCCCCG<br>AGCCCAAGAGCTGCGACACCCCCCCCCC<br>CTGCCCCGGTGCCCCGAGCCCAAGAGC<br>TGCGACACCCCCCCCCCTGCCCCGGTG<br>CCCCGCCCCGAGCTGCTGGGCGGCCCC<br>AGCGTGTTCCTGTTCCCCCCCAAGCCCAA<br>GGACACCCTGATGATCAGCCGGACCCCC<br>GAGGTGACCTGCGTGGTGGTGGACGTG<br>AGCCACGAGGACCCCGAGGTGCAGTTCA<br>AGTGGTACGTGGACGGCGTGGAGGTGC<br>ACAACGCCAAGACCAAGCCCCGGGAGG<br>AGCAGTACAACAGCACCTTCCGGGTGGT<br>GAGCGTGCTGACCGTGCTGCACCAGGAC<br>TGGCTGAACGGCAAGGAGTACAAGTGC<br>AAGGTGAGCAACAAGGCCCTGCCCGCCC<br>CCATCGAGAAGACCATCAGCAAGACCAA<br>GGGCCAGCCCCGGGAGCCCCAGGTGTA<br>CACCCTGCCCCCCAGCCGGGAGGAGATG<br>ACCAAGAACCAGGTGAGCCTGACCTGCC<br>TGGTGAAGGGCTTCTACCCCAGCGACAT<br>CGCCGTGGAGTGGGAGAGCAGCGGCCA<br>GCCCGAGAACAACTACAACACCACCCCC<br>CCCATGCTGGACAGCGACGGCAGCTTCT<br>TCCTGTACAGCAAGCTGACCGTGGACAA<br>GAGCCGGTGGCAGCAGGGCAACATCTTC<br>AGCTGCAGCGTGATGCACGAGGCCCTGC<br>ACAACCGGTTCACCCAGAAGAGCCTGAG<br>CCTGAGCCCCGGCAAG |
| >hIgG4 | | |
| SEQ ID NO: 79 | Constant HC | ASTKGPSVFPLAPCSRSTSESTAALGCLVKD<br>YFPEPVTVSWNSGALTSGVHTFPAVLQSS<br>GLYSLSSVVTVPSSSLGTKTYTCNVDHKPSN<br>TKVDKRVESKYGPPCPSCPAPEFLGGPSVF<br>LFPPKPKDTLMISRTPEVTCVVVDVSQEDP<br>EVQFNWYVDGVEVHNAKTKPREEQFNST<br>YRVVSVLTVLHQDWLNGKEYKCKVSNKGL<br>PSSIEKTISKAKGQPREPQVYTLPPSQEEMT<br>KNQVSLTCLVKGFYPSDIAVEWESNGQPE<br>NNYKTTPPVLDSDGSFFLYSRLTVDKSRW<br>QEGNVFSCSVMHEALHNHYTQKSLSLSLGK |
| SEQ ID NO: 80 | DNA Constant HC | GCCTCTACCAAGGGCCCCAGCGTGTTCC<br>CCCTGGCCCCCTGCAGCAGAAGCACCAG<br>CGAGAGCACAGCCGCCCTGGGCTGCCTG<br>GTGAAGGACTACTTCCCCGAGCCAGTGA<br>CCGTGTCCTGGAACAGCGGAGCCCTGAC<br>CAGCGGCGTGCACACCTTCCCCGCCGTG<br>CTGCAGAGCAGCGGCCTGTACAGCCTGT<br>CCAGCGTGGTGACCGTGCCCAGCAGCAG<br>CCTGGGCACCAAGACCTACACCTGCAAC<br>GTGGACCACAAGCCCAGCAACACCAAGG<br>TGGACAAGAGGGTGGAGAGCAAGTACG<br>GCCCACCCTGCCCCTCTTGCCCAGCCCC<br>GAGTTCCTGGGCGGACCCTCCGTGTTCCT |

TABLE 14-continued

Sequence list

GTTCCCCCCCAAGCCCAAGGACACCCTG
ATGATCAGCAGGACCCCCGAGGTGACCT
GCGTGGTGGTGGACGTGAGCCAGGAAG
ATCCAGAGGTCCAGTTCAACTGGTACGT
GGACGGCGTGGAGGTGCACAACGCCAA
GACCAAGCCCAGAGAGGAACAGTTTAAC
AGCACCTACAGGGTGGTGTCCGTGCTGA
CCGTGCTGCACCAGGACTGGCTGAACGG
CAAAGAGTACAAGTGCAAGGTCTCCAAC
AAGGGCCTGCCCAGCTCCATCGAGAAAA
CCATCAGCAAGGCCAAGGGCCAGCCACG
GGAGCCCCAGGTGTACACCCTGCCACCC
TCCCAGGAAGAGATGACCAAGAACCAG
GTGTCCCTGACCTGTCTGGTGAAGGGCT
TCTACCCCAGCGACATCGCCGTGGAGTG
GGAGAGCAACGGCCAGCCCGAGAACAA
CTACAAGACCACCCCCCCAGTGCTGGAC
AGCGACGGCAGCTTCTTCCTGTACAGCA
GGCTGACCGTGGACAAGTCCAGGTGGC
AGGAAGGCAACGTCTTTAGCTGCAGCGT
GATGCACGAGGCCCTGCACAACCACTAC
ACCCAGAAGAGCCTGAGCCTGTCCCTGG
GCAAG

>hIgG1 LALA

| SEQ ID NO: 81 | Constant HC | ASTKGPSVFPLAPSSKSTSGGTAALGCLVK<br>DYFPEPVTVSWNSGALTSGVHTFPAVLQS<br>SGLYSLSSVVTVPSSSLGTQTYICNVNHKPS<br>NTKVDKKVEPKSCDKTHTCPPCPAPEAAG<br>GPSVFLFPPKPKDTLMISRTPEVTCVVVDV<br>SHEDPEVKFNWYVDGVEVHNAKTKPREE<br>QYNSTYRVVSVLTVLHQDWLNGKEYKCKV<br>SNKALPAPIEKTISKAKGQPREPQVYTLPPS<br>REEMTKNQVSLTCLVKGFYPSDIAVEWES<br>NGQPENNYKTTPPVLDSDGSFFLYSKLTVD<br>KSRWQQGNVFSCSVMHEALHNHYTQKSL<br>SLSPGK |
|---|---|---|
| SEQ ID NO: 82 | DNA Constant HC | GCCTCCACCAAGGGTCCATCGGTCTTCCC<br>CCTGGCACCCTCCTCCAAGAGCACCTCTG<br>GGGGCACAGCGGCCCTGGGCTGCCTGG<br>TCAAGGACTACTTCCCCGAACCGGTGAC<br>GGTGTCGTGGAACTCAGGCGCCCTGACC<br>AGCGGCGTGCACACCTTCCCGGCTGTCC<br>TACAGTCCTCAGGACTCTACTCCCTCAGC<br>AGCGTGGTGACCGTGCCCTCCAGCAGCT<br>TGGGCACCCAGACCTACATCTGCAACGT<br>GAATCACAAGCCCAGCAACACCAAGGTG<br>GACAAGAGAGTTGAGCCCAAATCTTGTG<br>ACAAAACTCACACATGCCCACCGTGCCC<br>AGCACCTGAAGCAGCGGGGGGACCGTC<br>AGTCTTCCTCTTCCCCCCAAAACCCAAGG<br>ACACCCTCATGATCTCCCGGACCCCTGAG<br>GTCACATGCGTGGTGGTGGACGTGAGCC<br>ACGAAGACCCTGAGGTCAAGTTCAACTG<br>GTACGTGGACGGCGTGGAGGTGCATAA<br>TGCCAAGACAAAGCCGCGGGAGGAGCA<br>GTACAACAGCACGTACCGGGTGGTCAGC<br>GTCCTCACCGTCCTGCACCAGGACTGGCT<br>GAATGGCAAGGAGTACAAGTGCAAGGT<br>CTCCAACAAAGCCCTCCCAGCCCCCATCG<br>AGAAAACCATCTCCAAAGCCAAAGGGCA<br>GCCCCGAGAACCACAGGTGTACACCCTG<br>CCCCCATCCCGGGAGGAGATGACCAAGA<br>ACCAGGTCAGCCTGACCTGCCTGGTCAA<br>AGGCTTCTATCCCAGCGACATCGCCGTG<br>GAGTGGGAGAGCAATGGGCAGCCGGAG<br>AACAACTACAAGACCACGCCTCCCGTGC<br>TGGACTCCGACGGCTCCTTCTTCCTCTAC<br>AGCAAGCTCACCGTGGACAAGAGCAGG<br>TGGCAGCAGGGGAACGTCTTCTCATGCT<br>CCGTGATGCATGAGGCTCTGCACAACCA<br>CTACACGCAGAAGAGCCTCTCCCTGTCTC<br>CGGGTAAA |

TABLE 14-continued

| | Sequence list | |
|---|---|---|
| >hIgG1 N297A | | |
| SEQ ID NO: 83 | Constant HC | ASTKGPSVFPLAPSSKSTSGGTAALGCLVK
DYFPEPVTVSWNSGALTSGVHTFPAVLQS
SGLYSLSSVVTVPSSSLGTQTYICNVNHKPS
NTKVDKKVEPKSCDKTHTCPPCPAPELLGG
PSVFLFPPKPKDTLMISRTPEVTCVVVDVS
HEDPEVKFNWYVDGVEVHNAKTKPREEQ
YASTYRVVSVLTVLHQDWLNGKEYKCKVS
NKALPAPIEKTISKAKGQPREPQVYTLPPSR
EEMTKNQVSLTCLVKGFYPSDIAVEWESN
GQPENNYKTTPPVLDSDGSFFLYSKLTVDK
SRWQQGNVFSCSVMHEALHNHYTQKSLS
LSPGK |
| SEQ ID NO: 84 | DNA Constant HC | GCTAGCACCAAGGGCCCCTCCGTGTTCC
CTCTGGCCCCCTCCAGCAAGTCCACCTCT
GGCGGCACCGCCGCTCTGGGCTGCCTGG
TGAAAGACTACTTCCCCGAGCCCGTGAC
CGTGTCCTGGAACTCTGGCGCCCTGACCT
CCGGCGTGCACACCTTTCCAGCCGTGCT
GCAGTCCTCCGGCCTGTACTCCCTGTCCT
CCGTGGTGACCGTGCCCTCTAGCTCTCTG
GGCACCCAGACCTACATCTGCAACGTGA
ACCACAAGCCCTCCAACACCAAGGTGGA
CAAGCGGGTGGAACCCAAGTCCTGCGAC
AAGACCCACACCTGTCCCCCCTGCCCTGC
CCCTGAACTGCTGGGCGGACCTTCCGTG
TTCCTGTTCCCCCCAAAGCCCAAGGACAC
CCTGATGATCTCCCGGACCCCCGAAGTG
ACCTGCGTGGTGGTGGACGTGTCCCACG
AGGACCCTGAAGTGAAGTTCAATTGGTA
CGTGGACGGCGTGGAAGTGCACAACGC
CAAGACCAAGCCCAGAGAGGAACAGTA
CGCCTCCACCTACCGGGTGGTGTCTGTG
CTGACCGTGCTGCACCAGGACTGGCTGA
ACGGCAAAGAGTACAAGTGCAAGGTCTC
CAACAAGGCCCTGCCTGCCCCCATCGAA
AAGACCATCTCCAAGGCCAAGGGCCAGC
CCCGCGAGCCACAGGTGTACACACTGCC
CCCCAGCCGGGAAGAGATGACCAAGAA
CCAGGTGTCCCTGACCTGTCTGGTCAAA
GGCTTCTACCCCTCCGATATCGCCGTGGA
GTGGGAGTCCAACGGACAGCCCGAGAA
CAACTACAAGACCACCCCCCCTGTGCTG
GACTCCGACGGCTCATTCTTCCTGTACTC
CAAGCTGACCGTGGACAAGTCCCGGTGG
CAGCAGGGCAACGTGTTCTCCTGCTCCG
TGATGCACGAGGCCCTGCACAACCACTA
CACCCAGAAGTCCCTGTCCCTGAGCCCC
GGCAAG |
| >hIgG1 DAPA | | |
| SEQ ID NO: 85 | Constant HC | ASTKGPSVFPLAPSSKSTSGGTAALGCLVK
DYFPEPVTVSWNSGALTSGVHTFPAVLQS
SGLYSLSSVVTVPSSSLGTQTYICNVNHKPS
NTKVDKKVEPKSCDKTHTCPPCPAPELLGG
PSVFLFPPKPKDTLMISRTPEVTCVVVAVS
HEDPEVKFNWYVDGVEVHNAKTKPREEQ
YNSTYRVVSVLTVLHQDWLNGKEYKCKVS
NKALAAPIEKTISKAKGQPREPQVYTLPPSR
EEMTKNQVSLTCLVKGFYPSDIAVEWESN
GQPENNYKTTPPVLDSDGSFFLYSKLTVDK
SRWQQGNVFSCSVMHEALHNHYTQKSLS
LSPGK |
| SEQ ID NO: 86 | DNA Constant HC | GCTAGCACCAAGGGCCCCAGCGTGTTCC
CCCTGGCCCCCAGCAGCAAGAGCACCAG
CGGCGGCACAGCCGCCCTGGGCTGCCTG
GTGAAGGACTACTTCCCCGAGCCCGTGA
CCGTGTCCTGGAACAGCGGAGCCCTGAC
CTCCGGCGTGCACACCTTCCCCGCCGTGC
TGCAGAGCAGCGGCCTGTACAGCCTGTC
CAGCGTGGTGACAGTGCCCAGCAGCAGC
CTGGGCACCCAGACCTACATCTGCAACG
TGAACCACAAGCCCAGCAACACCAAGGT
GGACAAGAGAGTGGAGCCCAAGAGCTG |

TABLE 14-continued

Sequence list

```
CGACAAGACCCACACCTGCCCCCCCTGCC
CAGCCCCAGAGCTGCTGGGCGGACCCTC
CGTGTTCCTGTTCCCCCCCAAGCCCAAGG
ACACCCTGATGATCAGCAGGACCCCCGA
GGTGACCTGCGTGGTGGTGGCCGTGAG
CCACGAGGACCCAGAGGTGAAGTTCAAC
TGGTACGTGGACGGCGTGGAGGTGCAC
AACGCCAAGACCAAGCCCAGAGAGGAG
CAGTACAACAGCACCTACAGGGTGGTGT
CCGTGCTGACCGTGCTGCACCAGGACTG
GCTGAACGGCAAGGAATACAAGTGCAA
GGTCTCCAACAAGGCCCTGGCAGCCCCC
ATCGAAAAGACCATCAGCAAGGCCAAGG
GCCAGCCACGGGAGCCCCAGGTGTACAC
CCTGCCCCCCTCCCGGGAGGAGATGACC
AAGAACCAGGTGTCCCTGACCTGTCTGG
TGAAGGGCTTCTACCCCAGCGACATCGC
CGTGGAGTGGGAGAGCAACGGCCAGCC
CGAGAACAACTACAAGACCACCCCCCCA
GTGCTGGACAGCGACGGCAGCTTCTTCC
TGTACAGCAAGCTGACCGTGGACAAGTC
CAGGTGGCAGCAGGGCAACGTGTTCAG
CTGCAGCGTGATGCACGAGGCCCTGCAC
AACCACTACACCCAGAAGAGCCTGAGCC
TGTCCCCCGGCAAG
```

| | | |
|---|---|---|
| SEQ ID NO: 87 | Linker | A(EAAAK)$_n$ALE |
| SEQ ID NO: 88 | Linker | (D)-G-S-A-K |
| SEQ ID NO: 89 | Linker | GSADGGSSAG |
| SEQ ID NO: 90 | Linker | GGGAKGGGGKGGGS |
| SEQ ID NO: 91 | Linker | (Gly-Gly-Gly-Gly-Ser)$_n$ |
| SEQ ID NO: 92 | Linker | (Ser-Ser-Ser-Ser-Gly)$_n$ |
| SEQ ID NO: 93 | Linker | (Gly-Ser-Ser-Gly-Gly)$_n$ |
| SEQ ID NO: 94 | Linker | (Gly-Gly-Ser-Gly-Gly)$_n$ |
| SEQ ID NO: 95 | Linker | TVAAPS |
| SEQ ID NO: 96 | Linker | ASTSGPS |
| SEQ ID NO: 97 | Linker | KESGSVSSEQLAQFRSLD |
| SEQ ID NO: 98 | Linker | EGKSSGSGSESKST |
| SEQ ID NO: 99 | Linker | (Gly)$_6$ |
| SEQ ID NO: 100 | Linker | (Gly)$_8$ |
| SEQ ID NO: 101 | Linker | GSAGSAAGSGEF |

The invention claimed is:

1. A fusion protein comprising an antibody portion and an IL-2 portion joined directly or by one or more linkers, wherein:
   (a) The antibody portion comprises an anti-IL-2 isolated humanized antibody, or an IL-2-binding fragment thereof, comprising a light chain variable region (VL) comprising a light chain complementarity determining region 1 (LCDR1), a LCDR2 and a LCDR3 and a heavy chain variable region (VH) comprising a heavy chain CDR1 (HCDR1), a HCDR2 and a HCDR3; wherein the LCDR1 comprises SEQ ID NO: 22 or SEQ ID NO: 33 wherein the LCDR2 comprises SEQ ID NO: 15 or SEQ ID NO: 31; wherein the LCDR3 comprises SEQ ID NO: 16 or SEQ ID NO: 32; wherein the HCDR1 comprises SEQ ID NO: 11 or SEQ ID NO: 27; wherein the HCDR2 comprises SEQ ID NO: 12 or SEQ ID NO: 28; and wherein the HCDR3 comprises SEQ ID NO: 13 or SEQ ID NO: 29;
   (b) The IL-2 portion consists of a circularly permuted human interleukin 2 (hIL-2) polypeptide or variant thereof; and
   wherein the hIL-2 polypeptide or variant thereof is joined to the LCDR1 directly or by a N-terminal linker at residue Y8 of the LCDR1 and directly or by a C-terminal linker at residue D11 of the LCDR1.

2. The fusion protein according to claim 1, wherein the light chain variable (VL) and heavy chain variable (VH) regions of the antibody or fragment thereof used to prepare the fusion protein have at least 95% identity to the following amino acid sequences:
   VL of SEQ ID NO: 9; VH of SEQ ID NO: 7, respectively; or
   VL of SEQ ID NO: 26; VH of SEQ ID NO: 25, respectively.

3. The fusion protein according to claim 1, wherein the light chain variable (VL) and heavy chain variable (VH) regions of the antibody or fragment thereof when joined to the hIL-2 polypeptide or variant thereof each have at least 95% identity to any of the following amino acid sequence combinations, respectively:
   VL of SEQ ID NO: 56; SEQ ID NO: 57; SEQ ID NO: 58; SEQ ID NO: 59; SEQ ID NO: 60; SEQ ID NO: 61; or SEQ ID NO: 62; and VH of SEQ ID NO: 7, respectively; or
   VL of SEQ ID NO: 63; SEQ ID NO: 64; SEQ ID NO: 65; SEQ ID NO: 66; or SEQ ID NO: 67; and VH of SEQ ID NO: 25, respectively.

4. The fusion protein of claim 2, wherein the hIL-2 polypeptide or variant thereof is joined to the LCDR1 of the antibody or fragment thereof by a N-terminal linker at residue Y31 of the light chain variable region (VL) and a C-terminal linker at residue D34 of the light chain variable region (VL), thereby replacing the residues between Y31 and D34.

5. The fusion protein of claim 1, wherein the N-terminal and C-terminal linkers are both selected from the group consisting of no linker, a G linker, a GG linker, a GGG linker, a linker according to SEQ ID NO: 48, a linker according to SEQ ID NO: 49, a linker according to SEQ ID NO: 50, a linker according to SEQ ID NO: 51, a linker according to SEQ ID NO: 52, a linker according to SEQ ID NO: 53, a linker according to SEQ ID NO: 54, and a linker according to SEQ ID NO: 55.

6. The fusion protein of claim 4, wherein the residue Y31 is joined to residue N1 of the circularly permuted hIL-2 polypeptide or variant thereof with a GGG linker, and wherein residue D34 is joined to residue K132 of the circularly permuted hIL-2 polypeptide according to SEQ ID NO: 4 with a GGGG linker according to SEQ ID NO: 48.

7. The fusion protein according to claim 1, wherein the fusion protein has a heavy chain and a light chain comprising or consisting of amino acid sequences each having at least 95% identity, or being identical, to any of the following amino acid sequence combinations, respectively:
   SEQ ID NO:5 and SEQ ID NO:56, respectively,
   SEQ ID NO:5 and SEQ ID NO:57, respectively,
   SEQ ID NO:5 and SEQ ID NO:58, respectively,
   SEQ ID NO:5 and SEQ ID NO:59, respectively,
   SEQ ID NO:5 and SEQ ID NO:60, respectively,
   SEQ ID NO:5 and SEQ ID NO:61, respectively,
   SEQ ID NO:5 and SEQ ID NO:62, respectively,
   SEQ ID NO:23 and SEQ ID NO:63, respectively,
   SEQ ID NO:23 and SEQ ID NO:64, respectively,
   SEQ ID NO:23 and SEQ ID NO:65, respectively,
   SEQ ID NO:23 and SEQ ID NO:66, respectively, or
   SEQ ID NO:23 and SEQ ID NO:67, respectively.

8. The fusion protein according to claim 1, comprising a human IgG1 Fc portion.

9. A pharmaceutical composition comprising the fusion protein of claim 1 and a pharmaceutically acceptable carrier.

10. An isolated nucleic acid molecule encoding the fusion protein of claim 1.

11. An expression vector comprising the isolated nucleic acid molecule of claim 10.

12. An antibody-IL-2 fusion protein comprising a heavy chain and a light chain comprising amino acid sequences each being identical to any one of the following amino acid sequence combinations, respectively:

SEQ ID NO:5 and SEQ ID NO:56, respectively,
SEQ ID NO:5 and SEQ ID NO:57, respectively,
SEQ ID NO:5 and SEQ ID NO:58, respectively,
SEQ ID NO:5 and SEQ ID NO:59, respectively,
SEQ ID NO:5 and SEQ ID NO:60, respectively,
SEQ ID NO:5 and SEQ ID NO:61, respectively,
SEQ ID NO:5 and SEQ ID NO:62, respectively,
SEQ ID NO:23 and SEQ ID NO:63, respectively,
SEQ ID NO:23 and SEQ ID NO:64, respectively,
SEQ ID NO:23 and SEQ ID NO:65, respectively,
SEQ ID NO:23 and SEQ ID NO:66, respectively, and
SEQ ID NO:23 and SEQ ID NO:67, respectively.

13. A method of treating a cell proliferative disorder or cancer by (1) selecting a patient having a cell proliferative disorder or cancer and (2) administering a therapeutically effective amount of the fusion protein of claim 1.

14. The method of claim 13, wherein the therapeutically effective amount of the fusion protein is administered in a dosage amount of from about 0.01 to about 1 mg/kg.

15. A method of stimulating the immune system of an individual having cancer to prevent or destroy cancer cell growth, comprising administering to said individual an effective amount of a composition comprising the fusion protein of claim 1 and a pharmaceutically acceptable carrier, whereby the immune system of the individual is stimulated, thereby preventing or destroying cancer cell growth.

16. The method of claim 15, wherein the composition comprises the fusion protein of claim 6.

17. The method of claim 15, wherein the composition comprises the fusion protein of claim 7.

18. The pharmaceutical composition of claim 9, wherein the fusion protein comprises the fusion protein of claim 7.

19. The method of claim 13, wherein the fusion protein comprises the fusion protein of claim 7.

20. A method of treating a cell proliferative disorder or cancer by (1) selecting a patient having a cell proliferative disorder or cancer and (2) administering a therapeutically effective amount of the antibody-IL-2 fusion protein of claim 12.

* * * * *